US012611089B2

(12) United States Patent
Tearney et al.

(10) Patent No.: US 12,611,089 B2
(45) Date of Patent: Apr. 28, 2026

(54) IMAGING APPARATUS AND METHOD WHICH UTILIZES MULTIDIRECTIONAL FIELD OF VIEW ENDOSCOPY

(71) Applicant: The General Hospital Corporation, Boston, MA (US)

(72) Inventors: Guillermo J. Tearney, Cambridge, MA (US); Tao Wu, Cambridge, MA (US); Kevin E. Woods, Atlanta, GA (US); Timothy Nehiley Ford, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/902,153

(22) Filed: Sep. 2, 2022

(65) Prior Publication Data

US 2022/0409012 A1      Dec. 29, 2022

Related U.S. Application Data

(63) Continuation of application No. 14/906,090, filed as application No. PCT/US2014/047034 on Jul. 17, 2014, now Pat. No. 11,452,433.

(Continued)

(51) Int. Cl.
*A61B 1/00*          (2006.01)
*A61B 1/05*          (2006.01)
(Continued)

(52) U.S. Cl.
CPC ........ *A61B 1/0014* (2013.01); *A61B 1/00016* (2013.01); *A61B 1/00177* (2013.01);
(Continued)

(58) Field of Classification Search
CPC ............ A61B 1/00135; A61B 1/00137; A61B 1/0014

See application file for complete search history.

(56) References Cited

U.S. PATENT DOCUMENTS

| | | | |
|---|---|---|---|
| 2,339,754 | A | 1/1944 | Brace |
| 3,090,753 | A | 5/1963 | Matuszak et al. |
| | | (Continued) | |

FOREIGN PATENT DOCUMENTS

| | | |
|---|---|---|
| CN | 1550203 | 12/2004 |
| DE | 000004105221 | 9/1991 |
| | (Continued) | |

OTHER PUBLICATIONS

Trutna, W.R., et al., "Continuously Tuned External-Cavity Semi-conductor-Laser," Journal of Lightwave Technology, vol. 11, pp. 1279-1286, Aug. 1993.

(Continued)

*Primary Examiner* — Alexandra L Newton
(74) *Attorney, Agent, or Firm* — QUARLES & BRADY LLP

(57) ABSTRACT

Exemplary apparatus for coupling to a probe and providing information regarding at least one structure can be provided. For example, the apparatus can include an electronics arrangement which is configured to obtain the information and transmit the information wirelessly, and a structural connection configuration which is structured and configured to be attached to the probe. The electronics arrangement can include a detector arrangement which is configured to detect at least one return radiation from at least one portion of at least one sample based on the predetermined patterns, and provide the data for the portion(s) based on the return radiation(s). In addition, a computer arrangement can be provided which is configured to generate the information (Continued)

with includes image data for the portion(s) as a function of the data and prior knowledge of the predetermined patterns.

14 Claims, 16 Drawing Sheets

Related U.S. Application Data

(60) Provisional application No. 61/985,824, filed on Apr. 29, 2014, provisional application No. 61/856,152, filed on Jul. 19, 2013.

(51) Int. Cl.
A61B 1/06 (2006.01)
G02B 23/24 (2006.01)

(52) U.S. Cl.
CPC ...... A61B 1/00179 (2013.01); A61B 1/00181 (2013.01); A61B 1/05 (2013.01); A61B 1/053 (2013.01); A61B 1/0607 (2013.01); A61B 1/0615 (2013.01); A61B 1/0623 (2013.01); A61B 1/0638 (2013.01); A61B 1/0676 (2013.01); G02B 23/2484 (2013.01); A61B 1/00029 (2013.01)

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Hochberg et al. |
| 4,892,406 A | 1/1990 | Waters |
| 4,905,169 A | 2/1990 | Buican et al. |
| 4,909,631 A | 3/1990 | Cross, Jr. |
| 4,925,302 A | 5/1990 | Cutler |
| 4,928,005 A | 5/1990 | Lefevre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,127,730 A | 7/1992 | Brelje et al. |
| 5,177,488 A | 1/1993 | Wang et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican |
| 5,211,983 A | 5/1993 | Bley |
| 5,212,667 A | 5/1993 | Tomlinson et al. |
| 5,214,538 A | 5/1993 | Lobb |
| 5,217,456 A | 6/1993 | Narciso |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,400,771 A | 3/1995 | Pirak et al. |
| 5,404,415 A | 4/1995 | Mori et al. |
| 5,411,016 A | 5/1995 | Kume et al. |
| 5,414,509 A | 5/1995 | Veligdan |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,479,928 A | 1/1996 | Cathignol et al. |
| 5,486,701 A | 1/1996 | Norton et al. |
| 5,491,524 A | 2/1996 | Hellmuth et al. |
| 5,491,552 A | 2/1996 | Knuttel |
| 5,522,004 A | 5/1996 | Djupsjobacka et al. |
| 5,526,338 A | 6/1996 | Haman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knuttel |
| 5,566,267 A | 10/1996 | Nueberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab et al. |
| 5,628,313 A | 5/1997 | Webster, Jr. |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,701,155 A | 12/1997 | Welch et al. |
| 5,710,630 A | 1/1998 | Essenpreis et al. |
| 5,716,324 A | 2/1998 | Toida |
| 5,719,399 A | 2/1998 | Alfano et al. |

(56) References Cited

U.S. PATENT DOCUMENTS

| | | |
|---|---|---|
| 5,730,731 A | 3/1998 | Mollenauer et al. |
| 5,735,276 A | 4/1998 | Amelson |
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory |
| 5,829,439 A | 11/1998 | Yokosawa et al. |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Haam |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,052,186 A | 4/2000 | Tsai |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Lauer |
| 6,249,630 B1 | 6/2001 | Stock et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,293,909 B1 | 9/2001 | Chu et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang |
| 6,564,087 B1 | 5/2003 | Pitris et al. |
| 6,564,089 B2 | 5/2003 | Izatt et al. |
| 6,567,585 B2 | 5/2003 | Harris |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |

(56)  References Cited

U.S. PATENT DOCUMENTS

| | | | |
|---|---|---|---|
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,741,884 B1 | 5/2004 | Freeman et al. |
| 6,757,467 B1 | 6/2004 | Rogers |
| 6,790,175 B1 | 9/2004 | Furusawa et al. |
| 6,806,963 B1 | 10/2004 | Walti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | De Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,145,661 B2 | 12/2006 | Hitzenberger |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Apotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,310,150 B2 | 12/2007 | Tearney et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,365,858 B2 | 4/2008 | Fang-Yen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | De Boer et al. |
| 7,643,152 B2 | 1/2010 | De Boer et al. |
| 7,643,153 B2 | 1/2010 | De Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,799,558 B1 | 9/2010 | Dultz |
| 7,805,034 B2 | 9/2010 | Kato et al. |
| 7,911,621 B2 | 3/2011 | Motaghiannezam |
| 7,969,578 B2 | 6/2011 | Yun et al. |
| 7,973,936 B2 | 7/2011 | Dantus |

| | | | |
|---|---|---|---|
| 8,315,282 B2 | 11/2012 | Huber et al. |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2001/0055462 A1 | 12/2001 | Seibel |
| 2002/0016533 A1 | 2/2002 | Marchitto et al. |
| 2002/0024015 A1 | 2/2002 | Hoffmann et al. |
| 2002/0037252 A1 | 3/2002 | Toida |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Yun |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0166946 A1 | 11/2002 | Iizuka et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0025917 A1 | 2/2003 | Suhami |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0103212 A1 | 6/2003 | Westphal et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0191392 A1 | 10/2003 | Haldeman |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039252 A1 | 2/2004 | Koch, III |
| 2004/0039298 A1 | 2/2004 | Abreu |
| 2004/0054268 A1 | 3/2004 | Esenaliev et al. |
| 2004/0066824 A1 | 4/2004 | Magno et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |

(56) References Cited

U.S. PATENT DOCUMENTS

| | | |
|---|---|---|
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0188148 A1 | 9/2004 | Chen et al. |
| 2004/0189999 A1 | 9/2004 | De Groot et al. |
| 2004/0204651 A1 | 10/2004 | Freeman et al. |
| 2004/0212808 A1 | 10/2004 | Okawa et al. |
| 2004/0239938 A1 | 12/2004 | Izatt |
| 2004/0246490 A1 | 12/2004 | Wang et al. |
| 2004/0246583 A1 | 12/2004 | Mueller et al. |
| 2004/0247268 A1 | 12/2004 | Ishihara et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0000115 A1 | 1/2005 | Kimura et al. |
| 2005/0004453 A1 | 1/2005 | Tearney et al. |
| 2005/0018133 A1 | 1/2005 | Huang et al. |
| 2005/0018200 A1 | 1/2005 | Guillermo et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0049488 A1 | 3/2005 | Homan |
| 2005/0057680 A1 | 3/2005 | Agan |
| 2005/0057756 A1 | 3/2005 | Fen-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Wallace et al. |
| 2005/0221270 A1 | 10/2005 | Connelly et al. |
| 2005/0254059 A1 | 11/2005 | Alphonse |
| 2005/0254061 A1 | 11/2005 | Alphonse et al. |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Osypka et al. |
| 2006/0171503 A1 | 8/2006 | O'Hara et al. |
| 2006/0184048 A1 | 8/2006 | Saadat et al. |
| 2006/0189928 A1 | 8/2006 | Camus et al. |
| 2006/0193352 A1 | 8/2006 | Chong et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0024860 A1 | 2/2007 | Tobiason et al. |
| 2007/0035743 A1 | 2/2007 | Vakoc et al. |
| 2007/0038040 A1 | 2/2007 | Cense et al. |
| 2007/0048818 A1 | 3/2007 | Rosen et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0203404 A1 | 8/2007 | Zysk et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0238955 A1 | 10/2007 | Tearney et al. |
| 2007/0253901 A1 | 11/2007 | Deng et al. |
| 2007/0258094 A1 | 11/2007 | Izatt et al. |
| 2007/0260120 A1 | 11/2007 | Otawara |
| 2007/0263226 A1 | 11/2007 | Kurtz et al. |
| 2007/0270717 A1 | 11/2007 | Tang et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0013960 A1 | 1/2008 | Tearney et al. |
| 2008/0021275 A1 | 1/2008 | Tearney et al. |
| 2008/0049220 A1 | 2/2008 | Izzia et al. |
| 2008/0064925 A1 | 3/2008 | Gill et al. |
| 2008/0070323 A1 | 3/2008 | Hess et al. |
| 2008/0094613 A1 | 4/2008 | De Boer et al. |
| 2008/0094637 A1 | 4/2008 | De Boer et al. |
| 2008/0097225 A1 | 4/2008 | Tearney et al. |
| 2008/0097709 A1 | 4/2008 | De Boer et al. |
| 2008/0100837 A1 | 5/2008 | De Boer et al. |
| 2008/0139906 A1 | 6/2008 | Bussek |
| 2008/0152353 A1 | 6/2008 | De Boer et al. |
| 2008/0154090 A1 | 6/2008 | Hashimshony |
| 2008/0192236 A1 | 8/2008 | Smith et al. |
| 2008/0201081 A1 | 8/2008 | Reid |
| 2008/0204762 A1 | 8/2008 | Izatt et al. |
| 2008/0218696 A1 | 9/2008 | Mir |
| 2008/0226029 A1 | 9/2008 | Weir et al. |
| 2008/0228086 A1 | 9/2008 | Ilegbusi et al. |
| 2008/0234560 A1 | 9/2008 | Nomoto et al. |
| 2008/0252901 A1 | 10/2008 | Shimizu et al. |
| 2008/0265130 A1 | 10/2008 | Colomb et al. |
| 2008/0297806 A1 | 12/2008 | Motaghiannezam et al. |
| 2008/0308730 A1 | 12/2008 | Vizi et al. |
| 2009/0004453 A1 | 1/2009 | Murai et al. |
| 2009/0005691 A1 | 1/2009 | Huang |
| 2009/0011948 A1 | 1/2009 | Uniu et al. |
| 2009/0012368 A1 | 1/2009 | Banik |
| 2009/0023992 A1 | 1/2009 | Gilad et al. |
| 2009/0044799 A1 | 2/2009 | Qiu |
| 2009/0051923 A1 | 2/2009 | Zuluaga |
| 2009/0131801 A1 | 5/2009 | Suter et al. |
| 2009/0192358 A1 | 7/2009 | Yun |
| 2009/0196477 A1 | 8/2009 | Cense et al. |
| 2009/0209834 A1 | 8/2009 | Fine |
| 2009/0231419 A1 | 9/2009 | Bayer |
| 2009/0273777 A1 | 11/2009 | Yun et al. |
| 2009/0281390 A1 | 11/2009 | Quinjun et al. |
| 2009/0290156 A1 | 11/2009 | Popescu et al. |
| 2009/0305309 A1 | 12/2009 | Chien et al. |
| 2009/0306520 A1 | 12/2009 | Schmitt et al. |
| 2009/0323056 A1 | 12/2009 | Yun et al. |
| 2010/0002241 A1 | 1/2010 | Hirose |
| 2010/0086251 A1 | 4/2010 | Xu et al. |
| 2010/0094576 A1 | 4/2010 | De Boer et al. |
| 2010/0145145 A1 | 6/2010 | Shi et al. |
| 2010/0150467 A1 | 6/2010 | Zhao et al. |
| 2010/0198009 A1 | 8/2010 | Farr et al. |
| 2010/0261995 A1 | 10/2010 | McKenna et al. |
| 2010/0309477 A1 | 12/2010 | Yun et al. |
| 2011/0028790 A1 | 2/2011 | Farr et al. |
| 2011/0028967 A1 | 2/2011 | Rollins et al. |
| 2011/0160681 A1 | 6/2011 | Dacey, Jr. et al. |
| 2011/0218403 A1 | 9/2011 | Tearney et al. |
| 2011/0286089 A1 | 11/2011 | Jacobosen et al. |
| 2012/0209071 A1 | 8/2012 | Bayer et al. |
| 2012/0232345 A1 | 9/2012 | Levy et al. |
| 2014/0200406 A1* | 7/2014 | Bennett ............... A61B 1/0646 |
| | | 600/109 |
| 2014/0235948 A1* | 8/2014 | Mahalati ................ A61B 1/04 |
| | | 600/160 |
| 2014/0272764 A1* | 9/2014 | Miller ................... A61B 1/051 |
| | | 433/29 |
| 2014/0343358 A1 | 11/2014 | Hameed et al. |

FOREIGN PATENT DOCUMENTS

| | | |
|---|---|---|
| DE | 000004309056 | 9/1994 |
| DE | 000019542955 | 5/1997 |
| DE | 000010351319 | 6/2005 |

(56)          References Cited

FOREIGN PATENT DOCUMENTS

| | | |
|---|---|---|
| DE | 102005034443 | 2/2007 |
| EP | 0110201 | 6/1984 |
| EP | 0251062 | 1/1988 |
| EP | 590268 | 4/1994 |
| EP | 617286 | 9/1994 |
| EP | 0697611 | 2/1996 |
| EP | 728440 | 8/1996 |
| EP | 933096 | 8/1999 |
| EP | 1324051 | 7/2003 |
| EP | 1426799 | 6/2004 |
| EP | 2149776 | 2/2010 |
| FR | 2738343 | 8/1995 |
| GB | 1257778 | 12/1971 |
| GB | 2030313 | 4/1980 |
| GB | 2209221 | 9/1988 |
| GB | 2298054 | 3/1996 |
| JP | 6073405 | 4/1985 |
| JP | 361040633 | 3/1986 |
| JP | 62188001 | 6/1989 |
| JP | 1992056907 | 2/1992 |
| JP | 1992135550 | 5/1992 |
| JP | 1992135551 | 5/1992 |
| JP | 05509417 | 12/1993 |
| JP | H8136345 | 5/1996 |
| JP | H08160129 | 6/1996 |
| JP | 1997010213 | 1/1997 |
| JP | 9230248 | 9/1997 |
| JP | 1998213485 | 8/1998 |
| JP | 1998267631 | 10/1998 |
| JP | 1998267830 | 10/1998 |
| JP | 1990259617 | 10/1999 |
| JP | 2000023978 | 1/2000 |
| JP | 2000046729 | 2/2000 |
| JP | 2000121961 | 4/2000 |
| JP | 2000504234 | 4/2000 |
| JP | 2000126116 | 5/2000 |
| JP | 2000131222 | 5/2000 |
| JP | 2001004447 | 1/2001 |
| JP | 2001500026 | 1/2001 |
| JP | 2001104315 | 4/2001 |
| JP | 2001174404 | 6/2001 |
| JP | 2001174744 | 6/2001 |
| JP | 2001507251 | 6/2001 |
| JP | 2001508340 | 6/2001 |
| JP | 2007539336 | 6/2001 |
| JP | 2001212086 | 8/2001 |
| JP | 2001264246 | 9/2001 |
| JP | 2001515382 | 9/2001 |
| JP | 2001525580 | 12/2001 |
| JP | 2002503134 | 1/2002 |
| JP | 2002035005 | 2/2002 |
| JP | 2002095663 | 4/2002 |
| JP | 2002113017 | 4/2002 |
| JP | 2002148185 | 5/2002 |
| JP | 2002516586 | 6/2002 |
| JP | 2002205434 | 7/2002 |
| JP | 2002214127 | 7/2002 |
| JP | 2002214128 | 7/2002 |
| JP | 2003014585 | 1/2003 |
| JP | 2003035659 | 2/2003 |
| JP | 2003504627 | 2/2003 |
| JP | 2003512085 | 4/2003 |
| JP | 2003513278 | 4/2003 |
| JP | 2003516531 | 5/2003 |
| JP | 2004028970 | 1/2004 |
| JP | 2004037165 | 2/2004 |
| JP | 2004057652 | 2/2004 |
| JP | 2004089552 | 3/2004 |
| JP | 2004113780 | 4/2004 |
| JP | 2004514920 | 5/2004 |
| JP | 2004258144 | 9/2004 |
| JP | 2004317437 | 11/2004 |
| JP | 2005062850 | 3/2005 |
| JP | 2005110208 | 4/2005 |
| JP | 2005510323 | 4/2005 |
| JP | 2005156540 | 6/2005 |
| JP | 2005516187 | 6/2005 |
| JP | 2005195485 | 7/2005 |
| JP | 2005241872 | 9/2005 |
| JP | 2006237359 | 9/2006 |
| JP | 2007500059 | 1/2007 |
| JP | 2007083053 | 4/2007 |
| JP | 2007524455 | 8/2007 |
| JP | 2007271761 | 10/2007 |
| JP | 2008533712 | 8/2008 |
| JP | 2003102672 | 4/2012 |
| RU | 02108122 | 10/1998 |
| RU | 2149464 | 5/2000 |
| RU | 2209094 | 7/2003 |
| RU | 02213421 | 9/2003 |
| RU | 02242710 | 12/2004 |
| RU | 2255426 | 6/2005 |
| WO | 1979000841 | 10/1979 |
| WO | 1992001966 | 2/1992 |
| WO | 1992016865 | 10/1992 |
| WO | 1992019930 | 11/1992 |
| WO | 1993003672 | 3/1993 |
| WO | 1995033971 | 12/1995 |
| WO | 199602184 | 2/1996 |
| WO | 199604839 | 2/1996 |
| WO | 1996028212 | 9/1996 |
| WO | 1997032182 | 9/1997 |
| WO | 1998/001074 | 1/1998 |
| WO | 1998000057 | 1/1998 |
| WO | 1998014132 | 4/1998 |
| WO | 1998035203 | 8/1998 |
| WO | 1998038907 | 9/1998 |
| WO | 1998046123 | 10/1998 |
| WO | 1998048838 | 11/1998 |
| WO | 1998048846 | 11/1998 |
| WO | 1999005487 | 2/1999 |
| WO | 1999028856 | 6/1999 |
| WO | 199945838 | 9/1999 |
| WO | 1999044089 | 9/1999 |
| WO | 199945338 | 10/1999 |
| WO | 1999057507 | 11/1999 |
| WO | 200042906 | 7/2000 |
| WO | 2000043730 | 7/2000 |
| WO | 2000058766 | 10/2000 |
| WO | 2001001111 | 1/2001 |
| WO | 2001004828 | 1/2001 |
| WO | 2001008579 | 2/2001 |
| WO | 2001027679 | 4/2001 |
| WO | 2001033215 | 5/2001 |
| WO | 2001038820 | 5/2001 |
| WO | 2001042735 | 6/2001 |
| WO | 200182876 | 11/2001 |
| WO | 2002036015 | 5/2002 |
| WO | 2002038040 | 5/2002 |
| WO | 2002045572 | 6/2002 |
| WO | 2002068853 | 6/2002 |
| WO | 2002053050 | 7/2002 |
| WO | 2002054027 | 7/2002 |
| WO | 200283003 | 10/2002 |
| WO | 2002037075 | 10/2002 |
| WO | 2002084263 | 10/2002 |
| WO | 2003003903 | 1/2003 |
| WO | 2003012405 | 2/2003 |
| WO | 2003013624 | 2/2003 |
| WO | 2003020119 | 3/2003 |
| WO | WO/2003/046495 | 6/2003 |
| WO | WO/2003/046636 | 6/2003 |
| WO | WO/2003/052478 | 6/2003 |
| WO | WO/2003/053226 | 7/2003 |
| WO | WO/2003/062802 | 7/2003 |
| WO | WO/2003088826 | 10/2003 |
| WO | WO/2003/105678 | 12/2003 |
| WO | WO/2004/034869 | 4/2004 |
| WO | WO/2004037068 | 5/2004 |
| WO | WO/2004043251 | 5/2004 |
| WO | WO/2004/057266 | 7/2004 |
| WO | WO/2004073501 | 9/2004 |
| WO | WO/2004/088361 | 10/2004 |
| WO | WO/2004100789 | 11/2004 |

(56)                References Cited

FOREIGN PATENT DOCUMENTS

| WO | WO/2004/105598 | 12/2004 |
|----|----|----|
| WO | WO/2005045362 | 5/2005 |
| WO | WO/2005047813 | 5/2005 |
| WO | WO/2005/054780 | 6/2005 |
| WO | WO/2005/082225 | 9/2005 |
| WO | 2006004743 | 1/2006 |
| WO | 2006014392 | 2/2006 |
| WO | 2006020605 | 2/2006 |
| WO | 2006038876 | 4/2006 |
| WO | 2006039091 | 4/2006 |
| WO | 2006050320 | 5/2006 |
| WO | 2006058187 | 6/2006 |
| WO | 2006059109 | 6/2006 |
| WO | 2006124860 | 11/2006 |
| WO | 2006130797 | 12/2006 |
| WO | 2006131859 | 12/2006 |
| WO | 2007028531 | 3/2007 |
| WO | 2007030835 | 3/2007 |
| WO | 2007038787 | 4/2007 |
| WO | 2007070644 | 6/2007 |
| WO | 2007083138 | 7/2007 |
| WO | 2007084995 | 7/2007 |
| WO | 2009033064 | 3/2009 |
| WO | 2009153929 | 12/2009 |
| WO | 2011055376 | 5/2011 |
| WO | 2011080713 | 7/2011 |

OTHER PUBLICATIONS

Tuchin, V. et al., "Speckle interferometry in the measurements of biotissues vibrations," SPIE, 1647: 125 (1992).

Tuchin, Valery V., "Coherent Optical Techniques for the Analysis of Tissue Structure and Dynamics," Journal of Biomedical Optics, 1999, 4(1):106-124.

Turner, J.R. et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.

US National Library of Medicine (NLM}, Bethesda, MD, US; Oct. 2007 (Oct. 2007), "Abstracts of the 19 th Annual Symposium of Transcatheter Cardiovascular Therapeutics, Oct. 20-25, 2007, Washington, DC, USA."

Uttam, Deepak et al., "Precision Time Domain Reflectometry in Optical Fiber Systems Using a Frequency Modulated Continuous Wave Ranging Technique," Journal of Lightwave Technology, vol. 3, pp. 971-977, Oct. 1985.

Vabre, L., A. Dubois, et al. (2002). "Thermal-light full-field optical coherence tomography." Optics Letters 27(7): 530-532.

Vakhtin, A. B., D. J. Kane, et al. (2003). "Common-path interferometer for frequency-domain optical coherence tomography." Applied Optics 42(34): 6953-6958.

Vakhtin, A. B., K. A. Peterson, et al. (2003). "Differential spectral interferometry: an imaging technique for biomedical applications." Optics Letters 28(15): 1332-1334.

Vakoc, B. J., S. H. Yun, et al. (2005). "Phase-resolved optical frequency domain imaging." Optics Express 13(14): 5483-5493.

Van Leeuwen, T. G., M. D. Kulkarni, et al. (1999). "High-flow-velocity and shear-rate imaging by use of color Doppler optical coherence tomography." Optics Letters 24(22): 1584-1586.

Vansteenkiste, N., P. Vignola, et al. (1993). "Optical Reversibility Theorems for Polarization—Application to Remote-Control of Polarization." Journal of the Optical Society of America a-Optics Image Science and Vision 10(10): 2240-2245.

Vargas, O., E. K. Chan, et al. (1999). "Use of an agent to reduce scattering in skin." Lasers in Surgery and Medicine 24(2): 133-141.

Vaughan, J.M. et al., "Brillouin Scattering, Density and Elastic Properties of the Lens and Cornea of the Eye," Nature, vol. 284, Apr. 3, 1980, pp. 489-491.

Verschueren, Hendrik, "Interference Reflection Microscopy in Cell Biology," J. Cell Sci. 75, 1985, pp. 289-301.

Victor, S.Y. Lin et al., "A Porous Silicon-Based Optical Interferometric Biosensor," Science Magazine, vol. 278, pp. 840-843, Oct. 31, 1997.

Virmani et al., "Lesions from sudden coronary death: A comprehensive morphological classification scheme for atherosclerotic lesions," Arterioscler. Thromb. Vase. Bio., 20:1262-75 (2000).

Vogel, Alfred et al. (2003) "Mechanisms of Pulsed Laser Ablation of Biological Tissues" American Chemical Society vol. 103, pp. 577-644.

Von Der Weid, J.P. et al., "On the Characterization of Optical Fiber Network Componets with Optical Frequency Domain Reflectometry," Journal of Lightwave Technology, vol. 15, pp. 1131-1141, Jul. 1997.

Wang, R. K. (1999). "Resolution improved optical coherence-gated tomography for imaging through biological tissues." Journal of Modern Optics 46(13): 1905-1912.

Wang, X. J., T. E. Milner, et al. (1995). "Characterization of Fluid-Flow Velocity by Optical Doppler Tomography." Optics Letters 20(11): 1337-1339.

Wang, X. J., T. E. Milner, et al. (1997). "Measurement of fluid-flow-velocity profile in turbid media by the use of optical Doppler tomography." Applied Optics 36(1): 144-149.

Wang, Xiao-Jun et al., "Characterization of Dentin and Enamel by Use of Optical Coherence Tomography," Applied Optics, vol. 38, No. 10, pp. 2092-2096, Apr. 1, 1999.

Wang, Xuedong et al., (2001). "Propagation of Polarized Light in Birefringent Turbidd Media: Time-Resolved Simulations," Optical Imaging Laboratory, Biomedical Engineering Program, Texas A&M University, pp. 254-259, Aug. 27, 2001.

Wang, Y. M., J. S. Nelson, et al. (2003). "Optimal wavelength for ultrahigh-resolution optical coherence tomography." Optics Express 11(12): 1411-1417.

Wang, Y. M., Y. H. Zhao, et al. (2003). "Ultrahigh-resolution optical coherence tomography by broadband continuum generation from a photonic crystal fiber." Optics Letters 28(3): 182-184.

Watkins, L. R., S. M. Tan, et al. (1999). "Determination of interferometer phase distributions by use of wavelets." Optics Letters 24(13): 905-907.

Webb RH et al. "Confocal Scanning Laser Ophthalmoscope", Applied Optics 1987, 26 (8): 1492-1499.

Wentworth, R.H. (1989). "Theoretical Noise Performance of Coherence-Multiplexed Interferometric Sensors." Journal of Lightwave Technology 7(6): 941-956.

Westphal et al., "Correlation of Endoscopic Optical Coherence Tomography with Histology in the Lower-GI Tract," Gastrointestinal Endoscopy, Elsevier, NL, vol. 61, No. 4, Apr. 1, 2005.

Westphal, V., A. M. Rollins, et al. (2002). "Correction of geometric and refractive image distortions in optical coherence tomography applying Fermat's principle." Optics Express 10(9): 397-404.

Westphal, V., S. Yazdanfar, et al. (2002). "Real-time, high velocity-resolution color Doppler optical coherence tomography." Optics Letters 27(1): 34-36.

Wetzel, J. (2001). "Optical coherence tomography in dermatology: a review." Skin Research and Technology 7(1): 1-9.

Whelan, W.M et al. (2005) "A novel Strategy for Monitoring Laser Thermal Therapy Based on Changes in Optothermal Properties of Heated Tissues" International Journal of Thermophysics vol. 26., No. 1, pp. 233-241.

White, Brian R. et al., "In Vivo Dynamic Human Retinal Blood Flow Imaging Using Ultra-High-Speed Spectral Domain Optical Doppler Tomography," Optics Express, vol. 11, No. 25, pp. 3490-3497, Dec. 15, 2003.

Wieser, Wolfgang et al., "Multi-Megahertz OCT: High Quality 3D Imaging at 20 million A-Scans and 4.5 Gvoxels Per Second" Jul. 5, 2010, vol. 18, No. 14, Optics Express.

Williams, P. A. (1999). "Rotating-wave-plate Stokes polarimeter for differential group delay measurements of polarization-mode dispersion." Applied Optics 38(31): 6508-6515.

Wojtkowski, M., A. Kowalczyk, et al. (2002). "Full range complex spectral optical coherence tomography technique in eye imaging." Optics Letters 27(16): 1415-1417.

Wojtkowski, M., R. Leitgeb, et al. (2002). "Fourier domain OCT imaging of the human eye in vivo." Proc. SPIE 4619: 230-236.

(56)                    References Cited

OTHER PUBLICATIONS

Wojtkowski, M., R. Leitgeb, et al. (2002). "In vivo human retinal imaging by Fourier domain optical coherence tomography." Journal of Biomedical Optics 7(3): 457-463.
Wojtkowski, M., T. Bajraszewski, et al. (2003). "Real-time in vivo imaging by high-speed spectral optical coherence tomography." Optics Letters 28(19): 1745-1747.
Wojtkowski, M., V. J. Srinivasan, et al. (2004). "Ultrahigh-resolution, high-speed, Fourier domain optical coherence tomography and methods for dispersion compensation." Optics Express 12(11): 2404-2422.
Wojtkwski, Maciej, Ph.D., "Three-Dimensional Retinal Imaging with High-Speed Ultrahigh-Resolution Optical Coherence Tomography," Opthalmology, Oct. 2005, 112(10): 1734-1746.
Wong, B. J. F., Y. H. Zhao, et al. (2004). "Imaging the internal structure of the rat cochlea using optical coherence tomography at 0.827 mum and 1.3 mum." Otolaryngology-Head and Neck Surgery 130(3): 334-338.
Wong, Brian J.F. et al., "Optical Coherence Tomography of the Rat Cochlea," Journal of Biomedical Optics, vol. 5, No. 4, pp. 367-370, Oct. 2000.
Wussling, M. et al., "Laser diffraction and speckling studies in skeletal and heart muscle", Biomed, Biochim, Acta, 1986, 45(1/2):S 23-S 27.
Wysocki, P.F., et al., "Broad-Spectrum, Wavelength-Swept, Erbium-Doped Fiber Laser at 1.55-Mu-M," Optical Letters, vol. 15, pp. 879-881, Aug. 1990.
Yabushita, H.B., et al. (2002) "Measurement of Thin Fibrous Caps in Atherosclerotic Plaques by Optical Coherence Tomography." American Heart Association, Inc, Circulation 2002;106;1640.
Yamanari M. et al., "Polarization sensitive Fourier domain optical coherence tomography with continuous polarization modulation", Proc. of SPIE, vol. 6079, 2006.
Yang, C., A. Wax, et al. (2001). "Phase-dispersion optical tomography." Optics Letters 26(10): 686-688.
Nakamura, Koichiro et al., "A New Technique of Optical Ranging by a Frequency-Shifted Feedback Laser," IEEE Phontonics Technology Letters, vol. 10, No. 12, pp. 1041-1135, Dec. 1998.
Nassif, N.A. et al., "In Vivo High-Resolution Video-Rate Spectral-Domain Optical Coherence Tomography of the Human Retina and Optic Nerve," Optics Express, vol. 12, No. 3, Feb. 9, 2004, pp. 367-376.
Nassif, Nader et al., "In Vivo Human Retinal Imaging by Ultrahigh-Speed Spectral Domain Optical Coherence Tomography," Optics Letters, vol. 29, No. 5, Mar. 1, 2004, pp. 480-482.
Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." Journal of Biomedical Optics 9(2): 274-281.
Nelson, J. S., K. M. Kelly, et al. (2001). "Imaging blood flow in human port-wine stain in situ and in real time using optical Doppler tomography." Archives of Dermatology 137(6): 741-744.
Neumann, RA. et al. (1991) "Enzyme Histochemical Analysis of Cell Viability After Argon Laser-Induced Coagulation Necrosis of the Skin" Journal of the American Academy of Dermatology vol. 25, No. 6, pp. 991-998.
Newson, T. P., F. Farahi, et al. (1988). "Combined Interferometric and Polarimetric Fiber Optic Temperature Sensor with a Short Coherence Length Source." Optics Communications 68(3): 161-165.
Nikles, Marc et al., "Brillouin gain spectrum characterization in single-mode optical fibers", Journal of Lightwave Technology 1997, 15 (10): 1842-1851.
Notice of Reasons for Rejection and English translation for Japanese Patent Application No. 2002-538830 dated May 12, 2008.
November, L. J. (1993). "Recovery of the Matrix Operators in the Similarity and Congruency Transformations—Applications in Polarimetry." Journal of the Optical Society of America a-Optics Image Science and Vision 10(4): 719-739.

Oh, Jung-Taek et al., "Polarization-Sensitive Optical Coherence Tomography for Photoelasticity Testing of Glass/Epoxy Composites," Optics Express, vol. 11, No. 14, Jul. 14, 2003, pp. 1669-1676.
Oh, W. Y., S. H. Yun, et al. (2005). "Wide tuning range wavelength-swept laser with two semiconductor optical amplifiers." Ieee Photonics Technology Letters 17(3): 678-680.
Oh, W.Y. et al., "High-Speed Polarization Sensitive Optical Frequency Domain Imaging with Frequency Multiplexing," Optics Express, vol. 16, No. 2, Jan. 1, 2008.
Oh, W.Y. et al.(2006) "Ultrahigh Speed Optical Frequency Domain Imaging and Application to laser Ablation Monitoring" Applied Physics Letters, vol. 88.
Oka, K. and T. Kato (1999). "Spectroscopic polarimetry with a channeled spectrum." Optics Letters 24(21): 1475-1477.
Okoshi, Takanori, "Polarization-State Control Schemes for Heterodyne or Homodyne Optical Fiber Communications," Journal of Lightwave Technology, vol. LT-3, pp. 1232-1237, Dec. 1995.
Okugawa, T. and K. Rotate (1996). "Real-time optical image processing by synthesis of the coherence function using real-time holography." Ieee Photonics Technology Letters 8(2): 257-259.
O'Reich et al., (2000) "Expression of Oestrogen and Progeterone Receptors in Low-Grade Endometrial Stromal Sarcomas," British Journal of Cancer, vol. 82, No. 5, pp. 1030-1034.
Oshima, M., R. Torii, et al. (2001). "Finite element simulation of blood flow in the cerebral artery." Computer Methods In Applied Mechanics and Engineering 191 (6-7): 661-671.
Overholt, Bergein F. et al. (1999) "Photodynamic Therapy for Barrett's Esophagus: Follow-Up in 100 Patients" Gastrointestinal Endoscopy vol. 49, No. 1, pp. 1-7.
Pan, Y. T., H.K. Xie, et al. (2001). "Endoscopic optical coherence tomography based on a microelectromechanical mirror." Optics Letters 26(24): 1966-1968.
Parisi, V., G. Manni, et al. (2001). "Correlation between optical coherence tomography, pattern electroretinogram, and visual evoked potentials in open-angle glaucoma patients." Ophthalmology 108(5): 905-12.
Park et al., "Diffraction Phase and Fluorescence Microscopy," Opt. Expr. 14 (18) 2006, pp. 8263-8268.
Park, B. H., M. C. Pierce, et al. (2005). "Real-time fiber-based multi-functional spectral-domain optical coherence tomography at 1.3 mum." Optics Express 13(11): 3931-3944.
Park, B. Hyle et al., "Comment on Optical-Fiber-Based Mueller Optical Coherence Tomography," Optics Letters, vol. 29, No. 24, Dec. 15, 2004, pp. 2873-2874.
Park, B. Hyle et al., "In Vivo Burn Depth Determination by High-Speed Fiber-Based Polarization Sensitive Optical Coherence Tomography," Journal of Biomedical Optics, vol. 6, No. 4, pp. 474-479, Oct. 2001.
Park, B. Hyle et al., "Jones Matrix Analysis for a Polarization-Sensitive Optical Coherence Tomography System Using Fiber-Optic Components," Optics Letters, vol. 29, No. 21, Nov. 1, 2004, pp. 2512-2514.
Park, B. Hyle et al., "Real-Time Multi-Functional Optical Coherence Tomography," Optics Express, vol. 11, No. 7, Apr. 7, 2003, pp. 782-793.
Park, D. H., J. W. Hwang, et al. (1998). "Use of laser Doppler flowmetry for estimation of the depth of burns." Plastic and Reconstructive Surgery 101(6): 1516-1523.
Parker, K. J. et al., "Techniques for Elastic Imaging: A Review", IEEE Engineering in Medicine and Biology, Nov./Dec. 1996, pp. 52-59.
Passy, R., et al., "Experimental and Theoretical Investigations of Coherent OFDR with Semiconductor-Laser Sources," Journal of Lightwave Technology, vol. 12, pp. 1622-1630, Sep. 1994.
PCT International Preliminary Report on Patentability for International Application No. PCT/US2004/038404 dated Jun. 2, 2006.
PCT International Search Report and Written Opinion for Application No. PCT/US2004/023585 filed Jul. 23, 2004.
PCT International Search Report and Written Opinion for Application No. PCT/US2006/031905 dated May 3, 2007.
PCT International Search Report and Written Opinion for Application No. PCT/US2007/060319 dated Jun. 6, 2007.

(56) References Cited

OTHER PUBLICATIONS

PCT International Search Report and Written Opinion for Application No. PCT/US2007/060481 dated May 23, 2007.
PCT International Search Report and Written Opinion for Application No. PCT/US2007/060657 dated Aug. 13, 2007.
PCT International Search Report and Written Opinion for Application No. PCT/US2007/060670 dated Sep. 21, 2007.
PCT International Search Report and Written Opinion for Application No. PCT/US2007/060717 dated May 24, 2007.
PCT International Search Report and Written Opinion for Application No. PCT/US2007/061815 dated Aug. 2, 2007.
PCT International Search Report and Written Opinion for Application No. PCT/US2007/062465 dated Aug. 8, 2007.
PCT International Search Report and Written Opinion for Application No. PCT/US2007/066017 dated Aug. 30, 2007.
PCT International Search Report for Application No. PCT/US2006/016677 filed Apr. 28, 2006.
PCT International Search Report for Application No. PCT/US2006/018865 filed May 5, 2006.
Pendry, J.B., A. J. Holden, et al. (1999). "Magnetism from conductors and enhanced nonlinear phenomena." Ieee Transactions on Microwave Theory and Techniques 47(11): 2075-2084.
Penninckx, D. and V. Morenas (1999). "Jones matrix of polarization mode dispersion." Optics Letters 24(13): 875-877.
Pfau, P. et al., (2003) "Criteria for the Diagnosis of Dysphasia by Endoscopic Optical Coherence Tomography," Gastrointestinal Endoscopy, vol. 58, No. 2, pp. 196-2002.
Pfefer, Jorje at al. (2006) "Performance of the Aer-O-Scope, A Pneumatic, Self Propelling, Self Navigating Colonoscope in Animal Experiments" Gastrointestinal Endoscopy vol. 63, No. 5, pp. AB223.
Pierce, M. C., M. Shishkov, et al. (2005). "Effects of sample arm motion in endoscopic polarization-sensitive optical coherence tomography." Optics Express 13(15): 5739-5749.
Pierce, Mark C. et al., "Advances in Optical Coherence Tomography Imaging for Dermatology," The Society for Investigative Dermatology, Inc. 2004, pp. 458-463.
De Boer, Johannes F. et al., "Review of Polarization Sensitive Optical Coherence Tomography and Stokes Vector Determination," Journal of Biomedical Optics, Jul. 2002, vol. 7, No. 3, pp. 359-371.
De Boer, Johannes F., et al., "Two-Dimensional Birefringence Imaging in Biological Tissue by Polarization-Sensitive Optical Coherence Tomography," Optics Letters, vol. 22, No. 12, pp. 934-936, Jun. 15, 1997.
De Boer, Johannes F., et al., "Determination of the Depth-Resolved Stokes Parameters of Light Backscattered from Turbid Media by use of Polarization-Sensitive Optical Coherence Tomography," Optics Letters, vol. 24, No. 5, pp. 300-302, Mar. 1, 1999.
De Boer, Johannes F., et al., "Review of Polarization Sensitive Optical Coherence Tomography and Stockes Vector Determination," Journal of Biomedical Optics, vol. 7, No. 3, pp. 359-371, Jul. 2002.
Deckelbaum, Lawrence I. (1994) "Coronary Laser Angioplasty" Lasers in Surgery and Medicine vol. 14, pp. 101-110.
Degroot, P. and L. Deck (1993). "3-Dimensional Imaging by Sub-Nyquist Sampling of White-Light Interferograms." Optics Letters 18(17): 1462-1464.
Denk, W., J. H. Strickler, et al. (1990). "2-Photon Laser Scanning Fluorescence Microscopy." Science 248(4951): 73-76.
Descour, M. R., A. H. 0. Karkkainen, et al. (2002). "Toward the development of miniaturized Imaging systems for detection of pre-cancer." IEEE Journal of Quantum Electronics 38(2): 122-130.
Desjardins, A.E., et al., "Speckle reduction in OCT using massively-parallel detection and frequency-domain ranging", Optics Express, May 15, 2006, vol. 14, No. 11, pp. 4736-4745.
Dettwiller, L. (1997). "Polarization state interference: A general investigation." Pure and Applied Optics 6(1): 41-53.
Devesa, Susan S. et al. (1998) "Changing Patterns in the Incidence of Esophageal and Gastric Carcinoma in the United States." American Cancer Society vol. 83, No. 10 pp. 2049-2053.

Dicarlo, C. D., W. P. Roach, et al. (1999). "Comparison of optical coherence tomography imaging of cataracts with histopathology." Journal of Biomedical Optics 4.
Ding, Z., Y. Zhao, et al. (2002). "Real-time phase-resolved optical coherence tomography and optical Doppler tomography." Optics Express 10(5): 236-245.
Dobrin, P. B. (1996). "Effect of histologic preparation on the cross-sectional area of arterial rings." Journal of Surgical Research 61(2): 413-5.
Donohue, D. J., B. J. Stoyanov, et al. (1995). "Numerical Modeling of the Corneas Lamellar Structure and Birefringence Properties." Journal of the Optical Society of America a-Optics Image Science and Vision 12(7): 1425-1438.
Doornbos, R. M. P., R. Lang, et al. (1999). "The determination of in vivo human tissue optical properties and absolute chromophore concentrations using spatially resolved steady-state diffuse reflectance spectroscopy." Physics in Medicine and Biology 44(4): 967-981.
Dorrer, C., et al., "Spectral Resolution and Sampling Issues in Fourier-Transform Spectral Interferometry," Journal of the Optical Society of America B-Optical Physics, vol. 17, pp. 1795-1802, Oct. 2000.
Drabe, K. et al., "Localization of Spontaneous Emission in front of a mirror," Optics Communications 73:91 (1989).
Drexler, W., A. Baumgartner, et al. (1997). "Biometric investigation of changes in the anterior eye segment during accommodation." Vision Research 37(19): 2789-2800.
Drexler, W., A. Baumgartner, et al. (1997). "Submicrometer precision biometry of the anterior segment of the human eye." Investigative Ophthalmology & Visual Science 38(7): 1304-1313.
Drexler, W., A. Baumgartner, et al. (1998). "Dual beam optical coherence tomography: signal identification for ophthalmologic diagnosis." Journal of Biomedical Optics 3 (1): 55-65.
Drexler, W., C. K. Hitzenberger, et al. (1995). "Measurement of the Thickness of Fundus Layers by Partial Coherence Tomography." Optical Engineering 34(3): 701-710.
Drexler, W., C. K. Hitzenberger, et al. (1996). "(Sub)micrometer precision biometry of the human eye by optical coherence tomography and topography." Investigative Ophthalmology & Visual Science 37(3): 4374-4374.
Drexler, W., C. K. Hitzenberger, et al. (1998). "Investigation of dispersion effects in ocular media by multiple wavelength partial coherence interferometry." Experimental Eye Research 66(1): 25-33.
Drexler, W., D. Stamper, et al. (2001). "Correlation of collagen organization with polarization sensitive imaging of in vitro cartilage: implications for osteoarthritis." Journal of Rheumatology 28(6): 1311-8.
Drexler, W., et al., "In Vivo Ultrahigh-Resolution Optical Coherence Tomography," Optics Letters, vol. 24, pp. 1221-1223, Sep. 1999.
Drexler, W., H. Sattmann, et al. (2003). "Enhanced visualization of macular pathology with the use of ultrahigh-resolution optical coherence tomography." Archives of Ophthalmology 121(5): 695-706.
Drexler, W., O. Findl, et al. (1997). "Clinical feasibility of dual beam optical coherence topography and tomography for ophthalmologic diagnosis." Investigative Ophthalmology & Visual Science 38(4): 1038-1038.
Drexler, W., O. Findl, et al. (1998). "Partial coherence interferometry: A novel approach to biometry in cataract surgery." American Journal of Ophthalmology 126(4): 524-534.
Drexler, W., U. Morgner, et al. (2001). "Ultrahigh-resolution ophthalmic optical coherence tomography. [erratum appears in Nat Med May 2001;7(5):636.]." Nature Medicine 7(4): 502-7.
Drexler, Wolfgang et al., "Ultrahigh-resolution optical coherence tomography", Journal of Biomedical Optics Spie USA, 2004, pp. 47-74.
Droog, E. J., W. Steenbergen, et al. (2001). "Measurement of depth of burns by laser Doppler perfusion imaging." Burns 27(6): 561-8.
Dubois, Arnaud et al., "Ultrahigh-resolution OCT using white-light interference microscopy", Proceedings of SPIE, 2003, vol. 4956, pp. 14-21.

(56) References Cited

OTHER PUBLICATIONS

Dubois, A., K. Grieve, et al. (2004). "Ultrahigh-resolution full-field optical coherence tomography.". Applied Optics 43 (14): 2874-2883.

Dubios, A., L. Vabre, et al. (2002). "High-resolution full-field optical coherence tomography with a Linnik microscope." Applied Optics 41(4): 805-812.

Ducros, M. G., J. D. Marsack, et al. (2001). "Primate retina imaging with polarization-sensitive optical coherence tomography." Journal of the Optical Society of America a-Optics Image Science and Vision 18(12): 2945-2956.

Ducros, M., M. Laubscher, et al. (2002). "Parallel optical coherence tomography.in scattering samples using a two-dimensional smart-pixel detector array." Optics Communications 202(1-3): 29-35.

Ducros, Mathieu G. et al., "Polarization Sensitive Optical Coherence Tomography of the Rabbit Eye," IEEE Journal of Selected Topics in Quantum Electronics, vol. 5, No. 4, pp. 1159-1167, Jul./Aug. 1999.

Dudley, J.M., et al., "Cross-Correlation Frequency Resolved Optical Gating Analysis of Broadband Continuum Generation in Photonic Crystal Fiber: Simulations and Experiments," Optics Express, vol. 10, p. 1215, Oct. 2002.

Duncan, A., J. H. Meek, et al. (1995). "Optical Pathlength Measurements on Adult Head, Calf and Forearm and the Head of the Newborn-Infant Using Phase-Resolved Optical Spectroscopy." Physics in Medicine and Biology 40(2): 295-304.

Eickhoff, W., et al., "Optical Frequency-Domain Reflectometry in Single-Mode Fiber," Applied Physics Letters, vol. 39, pp. 693-695, 1981.

Eigensee, A, G. Haeusler, et al. (1996). "New method of short-coherence interferometry in human skin (in vivo) and in solid volume scatterers," Proceedings of SPIE—The International Society for Optical Engineering 2925: 169-178.

Eisenbeiss, W., J. Marotz, et al. (1999). "Reflection-optical multispectral imaging method for objective determination of burn depth." Burns 25(8): 697-704.

Elbaum, M., M. King, et al. (1972). "Wavelength-Diversity Technique for Reduction of Speckle Size." Journal of the Optical Society of America 62(5): 732-&.

Elliott, K. H. "The use of commercial CCD cameras as linear detectors in the physics undergraduate teaching laboratory", European Journal of Physics, 1998, pp. 107-117.

Enock, Jonathan, (2005) "Dual Reference Arm Low-Coherence Interferometer-Based Reflectometer For Optical Coherence Tomography (OCT) Application" Optics Communications, vol. 252.

Erdelyi et al. "Generation of diffraction-free beams for applications in optical microlithography", J. Vac. Sci. Technol. B 15 (12), Mar./Apr. 1997, pp. 287-292.

Ervin, J.C., H. G. Lemij, et al. (2002). "Clinician change detection viewing longitudinal stereophotographs compared to confocal scanning laser tomography in the LSU Experimental Glaucoma (LEG) Study." Ophthalmology 109(3): 467-81.

Escobar, P.F. et al., "Diagnostic efficacy of optical coherence tomography in the management of preinvasive and invasive cancer of uterine cervix and vulva",-Int. Journal of Gynecological Cancer 2004, 14, pp. 470-474.

Essenpreis, M., C. E. Elwell, et al. (1993). "Spectral Dependence of Temporal Point Spread Functions in Human Tissues." Applied Optics 32(4): 418-425.

Kobayashi, M., H. Hanafusa, et al. (1991). "Polarization-Independent Interferometric Optical-Time—Domain Reflectometer." Journal of Lightwave Technology: 9(5): 623-628.

Kohlhaas, Andreas et al., "High Resolution OCDR for Testing Integrated-Optical Waveguides: Dispersion-Corrupted Experimental Data Corrected by a Numerical Algorithm," Journal of Lightwave Technology, vol. 9, pp. 1493-1502, Nov. 1991.

Kolias, M. C., M. D. Sherar, et al. (1995). "Large Blood-Vessel Cooling in Heated Tissues—a Numerical Study." Physics in Medicine and Biology: 40(4): 477-494.

Koozekanani, D., K. Boyer, et al. (2001). "Retinal thickness measurements from optical coherence tomography using a Markov boundary model." Ieee Transactions on Medical Imaging 20(9): 900-916.

Kop, R. H.J. and R. Sprik (1995). "Phase-sensitive interferometry with ultrashort optical pulses." Review of Scientific Instruments 66(12): 5459-5463.

Koski, K.J. et al., "Brillouin imaging" Applied Physics Letters 87, 2005.

Kourogi, M. et al., "Programmable High Speed (1MHZ) Vernier-mode-locked Frequency-Swept Laser for OCT Imaging," Proceedings of SPIE, vol. 6847, Feb. 7, 2008.

Kramer, R. Z., J. Bella, et al. (1999). "Sequence dependent conformational variations of collagen triple-helical structure." Nature Structural Biology: 6(5): 454-7.

Kubba, A.K. et al. (1999) "Role of p53 Assessment in Management of Barrett's Esophagus" Digestive Disease and Sciences vol. 44, No. 4. pp. 659-667.

Kuipers, E.J et al. (2005) "Diagnostic and Therapeutic Endoscopy" Journal of Surgical Oncology vol. 92, pp. 203-209.

Kulkarni, et al., "Image Enhancment in Optical Coherene Tomography Using Deconvolution," Electronics Letters, vol. 33, pp. 1365-1367, Jul. 1997.

Kulkarni, M. D., T. G. van Leeuwen, et al. (1998). "Velocity-estimation accuracy and frame-rate limitations in color Doppler optical coherence tomography." Optics Letters 23(13): 1057-1059.

Kuranov, R.V. et al., "Complementary Use of Cross-Polarization and Standard OCT for Differential Diagnosis of Pathological Tissues," vol. 10, No. 15, pp. 707-713, Jul. 29, 2002.

Kwon, Y. H., C. S. Kim, et al. (2001). "Rate of visual field loss and long-term visual outcome in primary open-angle glaucoma." American Journal of Ophthalmology: 132(1): 47-56.

Kwong, K. F., D. Yankelevich, et al. (1993). "400-Hz Mechanical Scanning Optical Delay-Line." Optics Letters 18(7): 558-560.

Landers, J., I. Goldberg, et al. (2002). "Analysis of risk factors that may be associated with progression from ocular hypertension to primary open angle glaucoma." Clin Experiment Ophthalmology 30(4): 242-7.

Larkin, Kieran G., "Efficient Nonlinear Algorithm for Envelope Detection in White Light Interferometry," Journal of the Optical Society of America A-Optics Image Science and Vision, vol. 13, pp. 832-843, Apr. 1996.

Laszlo, A. and A. Venetianer (1998). "Heat resistance in mammalian cells: lessons and challenges. [Review] [52 refs]." Annals of the New York Academy of Sciences 851: 169-78.

Laszlo, A. and A. Venetianer (1998). Heat resistance in mammalian cells: Lessons and challenges. Stress of Life. 851: 169-178.

Lauer, V. "New approach to optical diffraction tomography yielding a vector equation of diffraction tomography and a novel tomographic microscope", Journal of Microscopy vol. 205, Issue 2, 2002, pp. 165-176.

Laufer, J., R. Simpson, et al. (1998). "Effect of temperature on the optical properties of ex vivo human dermis and subdermis." Physics in Medicine and Biology 43(9): 2479-2489.

Lederer, D. E., J. S. Schuman, et al. (2003). "Analysis of macular vol. in normal and glaucomatous eyes using optical coherence tomography." American Journal of Ophthalmology—135(6): 838-843.

Lee et al., "The Unstable Atheroma," Arteriosclerosis, Thrombosis & Vascular Biology, 17: 1859-67 (1997).

Lee, P. P., Z. W. Feldman, et al. (2003). "Longitudinal prevalence of major eye diseases." Archives Of Ophthalmology 121(9): 1303-1310.

Lee, Seok-Jeong et al., "Ultrahigh Scanning Speed Optical Coherence Tomography Using Optical Frequency Comb Generators," The Japan Society of Applied Physics, vol. 40 (2001).

Lees, S. et al., "Studies of Compact Hard Tissues and Collagen by Means of Brillouin Light Scattering", Connective Tissue Research, 1990, vol. 24, pp. 187-205.

Lehrer, M. S., T. T. Sun, et al. (1998). "Strategies of epithelial repair: modulation of stem cell and transit amplifying cell proliferation." Journal of Cell Science 111(Pt 19): 2867-75.

(56)                    References Cited

OTHER PUBLICATIONS

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." Survey of Ophthalmology 24(Suppl): 335-610.

Leitgeb, R. A., C. K. Hitzenberger, et al. (2003). "Phase-shifting algorithm to achieve high-speed long-depth-range probing by frequency-domain optical coherence tomography." Optics Letters 28(22): 2201-2203.

Leitgeb, R. A., L. Schmetterer, et al. (2003). "R al-time assessment of retinal blood flow with ultrafast acquisition by color Doppler Fourier domain optical coherence tomography." Optics Express 11(23): 3116-3121.

Leitgeb, R. A., L. Schmetterer, et al. (2004). "Real-time measurement of in vitro flow by Fourier-domain color Doppler optical coherence tomography." Optics Letters 29 (2): 171-173.

Leitgeb, R. A., W. Drexler, et al. (2004). "Ultrahigh resolution Fourier domain optical coherence tomography." Optics Express 12(10): 2156-2165.

Leitgeb, R. et al., "Spectral measurement of Absorption by Spectroscopic Frequency-Domain Optical Coherence Tomography," Optics Letters, vol. 25, pp. 820-822, Jun. 2000.

Leitgeb, R., C. K. Hitzenberger, et al. (2003). "Performance of fourier domain vs. time domain optical coherence tomography." Optics Express 11(8): 889-894.

Leitgeb, R., L. F. Schmetterer, et al. (2002). "Flow velocity measurements by frequency domain short coherence interferometry." Proc. SPIE 4619: 16-21.

LeRoybrehonnet, F. and B. LeJeune (1997). "Utilization of Mueller matrix formalism to obtain optical targets depolarization and polarization properties." Progress in Quantum Electronics 21(2): 109-151.

Leske, M. C., A. Heijl, et al. (1999). "Early Manifest Glaucoma Trial. Design and Baseline Data." Ophthalmology 106 (11): 2144-2153.

Leske, M. C., A. M. Connell, et al. (1995). "Risk factors for open-angle glaucoma. The Barbados Eye Study. [see comments]." Archives of Ophthalmology 113(7): 918-24.

Leske, M. C., A. M. Connell, et al. (2001). "Incidence of open-angle glaucoma: the Barbados Eye Studies. The Barbados Eye Studies Group. [see comments]." Archives of Ophthalmology 119(1): 89-95.

Lewis, Neil E. et al., (2006) "Applications of Fourier Transform Infrared Imaging Microscopy in Neurotoxicity", Annals New York Academy of Sciences, Dec. 17, 2006, vol. 820, pp. 234-246.

Lewis, S. E., J. R. DeBoer, et al. (2005). "Sensitive, selective, and analytical improvements to a porous silicon gas sensor." Sensors and Actuators B: Chemical 110(1): 54-65.

Lexer, F., C. K. Hitzenberger, et al. (1999). "Dynamic coherent focus OCT with depth-independent transversal resolution." Journal of Modern Optics 46(3): 541-553.

Lexer, F., et al., "Wavelength-Tuning Interferometry of Intraocular Distances," Applied Optics, vol. 36, pp. 6548-6553, Sep. 1997.

Li, X., C. Chudoba, et al. (2000). "Imaging needle for optical coherence tomography." Optics Letters 25: 1520-1522.

Li, X., T. H. Ko, et al. (2001). "Intraluminal fiber-optic Doppler imaging catheter for structural and functional optical coherence tomography." Optics Letters 26: 1906-1908.

Liddington, M. I. and P. G. Shakespeare (1996). "Timing of the thermographic assessment of burns." Burns 22(1): 26-8.

Lin, Stollen et al., (1977) A CW Tunable Near-infrared (1.085-1.175-um) Raman Oscillator, Optics Letters, vol. 1, 96.

Lindmo, T., D. J. Smithies, et al. (1998). "Accuracy and noise in optical Doppler tomography studied by Monte Carlo simulation." Physics in Medicine and Biology 43(10): 3045-3064.

Liptak, David C et al., (2007) "On the Development of a Confocal Rayleigh-Brillouin Microscope" American Institute of Physics, vol. 78, 016106.

Lisauskas, B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.

Beaud, P., et al., "Optical Reflectometry with Micrometer Resolution for the Investigation of Integrated Optical-Devices," Leee Journal of Quantum Electronics, vol. 25, pp. 755-759, Apr. 1989.

Beaurepaire, E., L. Moreaux, et al. (1999). "Combined scanning optical coherence and two-photon-excited fluorescence microscopy." Optics Letters 24(14): 969-971.

Beaurepaire, E., P. Gleyzes, et at. (1998). Optical coherence microscopy for the in-depth study of biological structures: System based on a parallel detection scheme, Proceedings of SPIE—The International Society for Optical Engineering.

Bechara, F. G., T. Gambichler, et al. (2004). "Histomorphologic correlation with routine histology and optical coherence tomography." Skin Research and Technology 10 (3): 169-173.

Bechmann, M., M. J. Thiel, et al. (2000). "Central corneal thickness determined with optical coherence tomography in various types of glaucoma. [see comments]." British Journal of Ophthalmology 84(11): 1233-7.

Beddow et al. (May 2002) "Improved Performance Interferometer Designs for Optical Coherence Tomography," IEEE Optical Fiber Sensors Conference, pp. 527-530.

Bednov, A.A. et al., "Investigation of Statistical Properties of Lymph Flow Dynamics Using Speckle-Microscopy," SPIE, 2981: 181-90 (1997).

Bek, T. and M. Kandi (2000). "Quantitative anomaloscopy and optical coherence tomography scanning in central serous chorioretinopathy." Acta Ophthalmological Scandinavica 78(6): 632-7.

Benoit, A. M., K. Naoun, et al. (2001). "Linear dichroism of the retinal nerve fiber layer expressed with Mueller matrices." Applied Optics 40(4): 565-569.

Bernet, S et al., "Quantitative Imaging of Complex Samples by Spiral Phase Contrast Microscopy," Optics Express, May 9, 2006.

Berovic, N. "Observation of Brillion scattering from single muscle fibers", European Biophysics Journal, 1989, vol. 17, pp. 69-74.

Betzig, E. et al., "Imaging intracellular fluorescent proteins at nanometer resolution," Science 313: 1642 (2006), stochastic optical reconstruction microscopy (STORM).

Bickel, William S., et al., "Stokes Vectors, Mueller Matrices, and Polarized Scattered Light," Am. J. Phys., vol. 53, No. 5, pp. 766-773, Feb. 1994.

Bicout, D., C. Brosseau, et al. (1994). "Depolarization of Multiply Scattered Waves by Spherical Diffusers—Influence of the Size Parameter." Physical Review E 49(2): 1767-1770.

Bilenca, A. et al., "The Role of Amplitude and Phase in Fluorescence Coherence Imaging: From Wide Filed to Nanometer Depth Profiling," Optics IEEE, May 5, 2007.

Bingid, U et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.

Blanchot, L., M. Lebec, et al. (1997). Low-coherence in depth microscopy for biological tissues imaging: Design of a real time control system. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." Survey of Ophthalmology 45(Suppl 3): S305-12; discussion S332-4.

Blumenthal, E. Z., J.M. Williams, et al. (2000). "Reproducibility of nerve fiber layer thickness measurements by use of optical coherence tomography." Ophthalmology 107(12): 2278-82.

Boas et al., "Diffusing temporal light correlation for burn diagnosis", SPIE, 1999, 2979:468-477.

Boogert, Jolanda Van Den et al. (1999) "Endoscopic Ablation Therapy for Barrett's Esophagua with High-Grade Dysplasia: A Review" The American Journal of Gastroenterology vol. 94, No. 5, pp. 1153-1160.

Boppart, S. A., B. E. Bouma, et al. (1996). "Imaging developing neural morphology using optical coherence tomography." Journal of Neuroscience Methods 70.

Boppart, S. A., B. E. Bouma, et al. (1997). "Forward-imaging instruments for optical coherence tomography." Optics Letters 22.

(56)                 References Cited

OTHER PUBLICATIONS

Boppart, S. A., B. E. Bouma, et al. (1998). "Intraoperative assessment of microsurgery with three-dimensional optical coherence tomography." Radiology 208: 81-86.

Boppart, S. A., J. Herrmann, et al. (1999). "High-resolution optical coherence tomography-guided laser ablation of surgical tissue." Journal of Surgical Research 82(2): 275-84.

Bouma, B. E. and G. J. Tearney (2002). "Clinical imaging with optical coherence tomography." Academic Radiology 9 (8): 942-953.

Bouma, B. E. and J. G. Fujimoto (1996). "Compact Kerr-lens mode-locked resonators." Optics Letters 21. 134-136.

Bouma, B. E., G. J. Tearney, et al. (1996). "Self-phase-modulated Kerr-lens mode-locked Cr.forsterite laser source for optical coherence tomography." Optics Letters 21(22): 1839.

Bouma, B. E., G. J. Tearney, et al. (2000). "High-resolution imaging of the human esophagus and stomach in vivo using optical coherence tomography." Gastrointestinal Endoscopy 51(4): 467-474.

Bouma, B. E., G. J. Tearney, et al. (2003). "Evaluation of intracoronary stenting by intravascular optical coherence tomography." Heart 89(3): 317-320.

Bouma, B. E., L. E. Nelson, et al. (1998). "Optical coherence tomographic imaging of human tissue at 1.55 mu m and 1.81 mu m using Er and Tm-doped fiber sources." Journal of Biomedical Optics 3. 76-79.

Bouma, B. E., M. Ramaswamy-Paye, et al. (1997). "Compact resonator designs for mode-locked solid-state lasers." Applied Physics B (Lasers and Optics) B65. 213-220.

Bouma, B.E. et al., "Diagnosis of Specialized Intestinal Metaplasia of the Esophagus with Optical Coherence Tomography," Conference on Lasers and Electro-Optics. Technical Digest. OSA, US, vol. 56, May 6, 2001.

Bouma, Bet al. (1994) "Hybrid Mode Locking of a Flash-Lamp-Pumped Ti: A}iO3 Laser" Optics Letters vol. 19, No. 22, pp. 1858-1860.

Bouma, Bet al. (1995) "High Resolution Optical Coherence Tomography Imaging Using a Mode-Locked Ti: AlzO3 aser Source" Optics Letters vol. 20, No. 13, pp. 1486-1488.

Bouma, Brett et al., "Power-Efficient Nonreciprocal Interferometer and Linear-Scanning Fiber-Optic Catheter for Optial Coherence Tomography." Optics Letters, vol. 24, pp. 531-533, Apr. 1999.

Bourquin, S., P. Seitz, et al. (2001). "Optical coherence topography based on a two-dimensional smart detector array." Optics Letters 26(8): 512-514.

Bourquin, S., V. Monterosso, et al. (2000). "Video-rate optical low-coherence reflectometry based on a linear smart detector array." Optics Letters 25(2): 102-104.

Bouzid, A., M.A. G. Abushagur, et al. (1995). "Fiber-optic four-detector polarimeter." Optics Communications 118 (3-4): 329-334.

Bowd, C., L. M. Zangwill, et al. (2001). "Detecting early glaucoma by assessment of retinal nerve fiber layer thickness and visual function." Investigative Ophthalmology & Visual Science 42(9):1993-2003.

Bowd, C., L. M. Zangwill, et al. (2002). "Imaging of the optic disc and retinal nerve fiber layer: the effects of age, optic disc area, refractive error, and gender." Journal of the Optical Society of America, A, Optics, Image Science, & Vision 19(1): 197-207.

Bowd, C., R. N. Weinreb, et al. (2000). "The retinal nerve fiber layer thickness in ocular hypertensive, normal, and glaucomatous eyes with optical coherence tomography." Archives of Ophthalmology 118(1): 22-6.

Bowery, D.J. et al., (1999) "Patterns of Gastritis in Patients with Gastro-Oesophageal Reflux Disease," Gut, vol. 45, pp. 798-803.

Brand, S., J.M. Poneros, et al. (2000). "Optical coherence tomography in the gastrointestinal tract." Endoscopy 32(10): 796-803.

Brehonnet, Le. Roy F., et al., "Optical Media and Target Characterization by Mueller Matrix Decomposition," J. Phys. D: Appl. Phys. 29, pp. 34-38, 1996.

Brezinski, M. E. and J. G. Fujimoto (1999). "Optical coherence tomography: high-resolution imaging in nontransparent tissue." IEEE Journal of Selected Togics in Quantum Electronics 5(4):1185-1192.

Brezinski, M. E., G. J. Tearney, et al. (1996). "Imaging of coronary artery microstructure (in vitro) with optical coherence tomography." American Journal of Cardiology 77 (1): 92-93.

Brezinski, M. E., G. J. Tearney, et al. (1996). "Optical coherence tomography for optical biopsy—Properties and demonstration of vascular pathology." Circulation 93(6): 1206-1213.

Brezinski, M. E., G. J. Tearney, et al. (1997). "Assessing atherosclerotic plaque morphology: Comparison of optical coherence tomography and high frequency intravascular ultrasound." Heart 77(5): 397-403.

Briers, David J. , "Speckle fluctuations and biomedical optics: implications and applications", Optical Engineering, 1993, 32(2):277-283.

Huang, F., W. Yang, et al. (2001). "Quadrature spectral interferometric detection and pulse shaping." Optics Letters 26(6): 382-384.

Huang, X. R. and R. W. Knighton (2002). "Linear birefringence of the retinal nerve fiber layer measured in vitro with a multispectral imaging micropolarimeter." Journal of Biomedical Optics 7(2): 199-204.

Huang, Xiang-Run et al., "Variation of Peripapillary Retinal Nerve Fiber Layer-Birefringence in Normal Human Subjects," Investigative Ophthalmology & Visual Science, vol. 45, No. 9, Sep. 2004, pp. 3073-3080.

Huber, R. et al., "Fourier Domain Mode Locked Lasers for OCT Imaging at up to 290 kHz Sweep Rates," Proceedings of SPIE, SPIE—International Society for Optical Engineering, US, vol. 5861, No. 1, Jan. 1, 2005.

Huber, R., M. Wojtkowski, et al. (2005). "Amplified, frequency swept lasers for frequency domain reflectometry and OCT imaging: design and scaling principles." Optics Express 13(9): 3513-3528.

Hunter, D. G., J.C. Sandruck, et al. (1999). "Mathematical modeling of retinal birefringence scanning." Journal of the Optical Society of America a-Optics Image Science and Vision 16(9):2103-2111.

Hurwitz, H. H. and R. C. Jones (1941). "A new calculus for the treatment of optical systems II. Proof of three general equivalence theorems." Journal of the Optical Society of America 31(7): 493-499.

Huttner, B., B. Gisin, et al. (1999). "Distributed PMD measurement with a polarization-OTDR in optical fibers." Journal of Lightwave Technology 17(10): 1843-1848.

Huttner, B., C. De Barros, et al. (1999). "Polarization-induced pulse spreading in birefringent optical fibers with zero differential group delay." Optics Letters 24(6): 370-372.

Huttner, B., J. Reecht, et al. (1998). "Local birefringence measurements in single-mode fibers with coherent optical frequency-domain reflectometry." Ieee Photonics Technology Letters 10(10): 1458-1460.

Hyde, S. C. W., N. P. Barry, et al. (1995). "Depth-Resolved Holographic Imaging through Scattering Media by Photorefraction." Optics Letters 20(11): 1331-1333.

Hyde, S. C. W., N. P. Barry, et al. (1995). "Sub-100-Mu-M Depth-Resolved Holographic Imaging through Scattering Media in the near-Infrared." Optics Letters 20(22): 2330-2332.

Iftimia, N. V., B. E. Bouma, et al. (2004). "Adaptive ranging for optical coherence tomography." Optics Express 12(17): 4025-4034.

Iftimia, Nicusor V., et al., (2005) "A Portable, Low Coherence Interferometry Based Instrument for Fine Needle Aspiration Biopsy Guidance," Accepted to Review of Scientific Instruments, published May 23, 2005.

Iida, T., N. Hagimura, et al. (2000). "Evaluation of central serous chorioretinopathy with optical coherence tomography." American Journal of Ophthalmology 129(1): 16-20.

Imai, M., H. Iijima, et al. (2001). "Optical coherence tomography of fractional macular elevations in eyes with proliferative diabetic retinopathy. [republished in Am J Ophthalmol. Sep. 2001;132(3):458-61 ; 11530091.]." American Journal of Ophthalmology 132(1): 81-4.

(56) References Cited

OTHER PUBLICATIONS

Indebetouw, G. and P. Klysubun (2000). "Imaging through scattering media with depth resolution by use of low-coherence gating in spatiotemporal digital holography." Optics Letters 25(4): 212-214.

Inoue, Kyo et al., "Nearly Degenerate 4-Wave-Mixing in a Traveling-Wave Semiconductor-Laser Amplifier," Applied Physics Letters, vol. 51, pp. 1051-1053, 1987.

Inoue, Yusuke et al., "Varible Phase-Contrast Fluorescence Spectrometry for Fluorescently Strained Cells," Applied Physics Letter, Sep. 18, 2006.

International Search Report for International Patent application No. PCT/US2004/039454 published May 11, 2005.

International Search Report for International Patent application No. PCT/US2001/049704 published Dec. 10, 2002.

International Search Report for International Patent application No. PCT/US2005/023664 published Oct. 12, 2005.

International Search Report for International Patent application No. PCT/US2005/030294 published Aug. 22, 2006.

International Search Report for International Patent application No. PCT/US2005/039740 published Feb. 21, 2006.

International Search Report for International Patent application No. PCT/US2005/043951 published Apr. 6, 2006.

International Written Opinion for International Patent application No. PCT/US2004/039454 published May 11, 2005.

International Written Opinion for International Patent application No. PCT/US2005/023664 published Oct. 12, 2005.

International Written Opinion for International Patent application No. PCT/US2005/039740 published Feb. 21, 2006.

International Written Opinion for International Patent application No. PCT/US2005/043951 published Apr. 6, 2006.

International Written Opinion for International Patent application No. PCT/US2006/016677 filed Apr. 28, 2006.

International Written Opinion for International Patent application No. PCT/US2006/018865 filed May 5, 2006.

IP, M. S., B. J. Baker, et al. (2002). "Anatomical outcomes of surgery for idiopathic macular hole as determined by optical coherence tomography." Archives of Ophthalmology 120(1): 29-35.

Ishikawa, Hiroshi et al. "Macular Segmentation with optical coherence tomography", Investigative Ophthalmology & Visual Science, vol. 46, No. 6, Jun. 2005, pp. 2012-2017.

Ismail, R., V. Tanner, et al. (2002). "Optical coherence tomography imaging of severe commotio retinae and associated-macular hole." British Journal of Ophthalmology 86(4): 473-4.

Ivanon, A.P., et al., "Interferometric Study of the Spatial Structure of a Light-Scattering Medium," Journal of Applied Spectroscopy, vol. 28, pp. 518-525, 1978.

Ivanov, A.P., et al., "New Method for High-Range Resolution Measurements of Light Scattering in Optically Dense Inhomogeneous Media," Optics Letters, vol. 1, pp. 226-228, Dec. 1977. IX, 2005, pp. 159-162.

Izatt, J. A., M. D. Kulkarni, et al. (1996). "Optical coherence tomography and microscopy in gastrointestinal tissues." IEEE Journal of Selected Topics in Quantum Electronics 2(4): 1017.

Izatt, J. A., M. D. Kulkarni, et al. (1997). "In vivo bidirectional color Doppler flow imaging of picoliter blood volumes using optical coherence tomography." Optics Letters 22(18): 1439-1441.

Izatt, J. A., M. R. Hee, et al. (1994). "Micrometer-scale resolution imaging of the anterior eye in vivo with optical coherence tomography." Archives of Ophthalmology 112 (12): 1584-9.

Zatt, J. A., M. R. Hee, et al. (1994). "Optical Coherence Microscopy in Scattering Media." Optics Letters 19(8): 590-592.

Jackle, S. et al., (2000) "In Vivo Endoscopic Optical Coherence Tomography of the Human Gastrointestinal Tract—Toward Optical Biopsy," Endoscopy, vol. 32, No. 10, pp. 743-749.

Jacques, S. L., J. R. Roman, et al. (2000). "Imaging superficial tissues with polarized light." Lasers in Surgery and Medicine 26(2): 119-129.

Jacques, S. L., J. S. Nelson, et al. (1993). "Pulsed Photothermal Radiometry of Port-Wine-Stain Lesions." Applied Optics 32(13): 2439-2446.

Jacques, Steven L. (1993) "Role of Tissue Optics and Pulse Duration on Tissue Effects During High-Power Laser Irradiation" Applied Optics vol. 32, No. 13, pp. 2447-2454.

Jang, I. K., B. D. MacNeill, et al. (2002). "In-vivo characterization of coronary plaques in patients with ST elevation acute myocardial infarction using optical coherence tomography (OCT)." Circulation 106(19): 698-698 3440 Suppl. S.

Jang, I. K., B. E. Bouma, et al. (2002). "Visualization of coronary atherosclerotic plaques in patients using optical coherence tomography: Comparison with intravascular ultrasound." Journal of the American College of Cardiology 39(4): 604-609.

Jang, I. K., G. J. Teamey, et al. (2000). "Comparison of optical coherence tomography and intravascular ultrasound for detection of coronary plaques with large lipid-core in living patients." Circulation 102(18): 509-509.

Jeng, J.C., A. Bridgeman, et al. (2003). "Laser Doppler imaging determines need for excision and grafting in advance of clinical judgment: a prospective blinded trial." Burns 29(7): 665-67.

Jerath, Maya R. et al.(1992) "Dynamic Optical Property Changes: Implications for Reflectance Feedback Control of Photocoagulation" Journal of Photochemical, Photobiology. B: Biol vol. 16, pp. 113-126.

Office Action dated Jan. 25, 2010 for U.S. Appl. No. 11/537,048.
Office Action dated Jan. 3, 2008 for U.S. Appl. No. 10/997,789.
Office Action dated Jan. 9, 2010 for U.S. Appl. No. 11/624,455.
Office Action dated Jul. 16, 2010 for U.S. Appl. No. 11/445,990.
Office Action dated Jul. 20, 2010 for U.S. Appl. No. 11/625,135.
Office Action dated Jul. 7, 2008 for U.S. Appl. No. 10/551,735.
Office Action dated Jul. 7, 2010 for U.S. Appl. No. 11/624,277.
Office Action dated Jun. 2, 2010 for U.S. Appl. No. 12/112,205.
Office Action dated Jun. 30, 2008 for U.S. Appl. No. 11/670,058.
Office Action dated Mar. 16, 2009 for U.S. Appl. No. 11/621,694.
Office Action dated Mar. 18, 2010 of U.S. Appl. No. 11/844,454.
Office Action dated Mar. 28, 2007 for U.S. Appl. No. 11/241,907.
Office Action dated May 15, 2009 for U.S. Appl. No. 11/537,123.
Office Action dated May 23, 2007 for U.S. Appl. No. 10/406,751.
Office Action dated May 23, 2007 for U.S. Appl. No. 10/551,735.
Office Action dated May 28, 2010 for U.S. Appl. No. 12/015,642.
Office Action dated Nov. 13, 2006 for U.S. Appl. No. 10/501,268.
Office Action dated Nov. 20, 2006 for U.S. Appl. No. 09/709,162.
Office Action dated Oct. 1, 2009 for U.S. Appl. No. 11/677,278.
Office Action dated Oct. 11, 2007 for U.S. Appl. No. 11/534,095.
Office Action dated Oct. 30, 2007 for U.S. Appl. No. 11/670,069.
Office Action dated Oct. 6, 2009 for U.S. Appl. No. 12/015,642.
Office Action dated Oct. 9, 2007 for U.S. Appl. No. 09/709,162.
Office Action dated Sep. 11, 2008 for U.S. Appl. No. 11/624,334.
Office Action dated Sep. 3, 2010 for U.S. Appl. No. 12/139,314.
Office Action mailed Oct. 1, 2008 for U.S. Appl. No. 11/955,986.

PCT International Preliminary Report on Patentability for Application No. PCT/US2005/043951 dated Jun. 7, 2007.

PCT International Search Report and Written Opinion for Application No. PCT/US2007/061463 dated Jan. 23, 2008.

PCT International Search Report and Written Opinion for Application No. PCT/US2007/061481 dated Mar. 17, 2008.

PCT International Search Report and Written Opinion for Application No. PCT/US2007/078254 dated Mar. 28, 2008.

PCT International Search Report for Application No. PCT/US2007/060787 dated Mar. 18, 2008.

PCT International Search Report for Application No. PCT/US2007/068233 dated Feb. 21, 2008.

Statement under Article 19 and Reply to PCT Written Opinion for PCT International Application No. PCT/US2005/04395 I dated Jun. 6, 2006.

Written Opinion for International Application No. PCT/US2014/047034 mailed on Nov. 26, 2014.

Creagan, R. F., B. J. Mangan, et al. (1999). "Single-mode photonic band gap guidance of light in air." Science 285(5433): 1537-1539.

D. Fu et al., "Non-invasive quantitative reconstruction of tissue elasticity using an iterative forward approach", Phys. Med. Biol. 2000 (45): 1495-1509.

Dalmolin,, M., A. Galtarossa, et al. (1997). "Experimental investigation of linear polarization in high-birefringence single-mode fibers." Applied Optics 36(12): 2526-2528.

(56) References Cited

OTHER PUBLICATIONS

D'Amico, A.V. et al., "Optical Coherence Tomography as a Method for Identifying Benign and Maliganat Microscopic Structures in the Prostate Gland," Urology, vol. 55, Issue May 5, 2000, ("C2"), pp. 783-787.

Danielson, B. L. and C. D. Whittenberg (1987). "Guided-Wave Reflectometry with Micrometer Resolution." Applied Optics 26(14): 2836-2842.

Danielson, B.L., et al., "Absolute Optical Ranging Using Low Coherence Interferometry," Applied Optics, vol. 30, p. 2975, Jul. 1991.

Database Compendex Engineering Information, Inc., New York, NY, US; Mar. 5, 2007, Yelin, Dvir et al: "Spectral-Domain Spectrally-Encoded Endocscopy".

Database Biosis Biosciences Information Service, Philadelphia, PA, US; Oct. 2006, Yelin D. et al.: "Thee-Dimensional Miniature Endoscopy".

Dave, D. P. and T. E. Milner (2000). "Doppler-angle measurement in highly scattering media." Optics Letters 25(20): 1523-1525.

Dave, Digant P. et al., "Polarization-Maintaining Fiber-Based Optical Low-Coherence Reflectometer for Characterization and Ranging of Birefringence," Optics Letters, vol. 28, No. 19, Oct. 1, 2003, pp. 1775-1777.

De Boer, J. F., C. E. Saxer, et al. (2001). "Stable carrier generation and phase-resolved digital data processing in optical coherence tomography." Applied Optics 40(31): 5787-5790.

De Boer, J. F., T. E. Milner, et al. (1998). Two dimensional birefringence imaging in biological tissue using phase and polarization sensitive optical coherence tomography, Trends in Optics and Photonics (TOPS): Advances in Optical Imaging and Photon Migration, Orlando, USA, Optical Society of America, Washington, DC 1998.

De Boer, Johannes F. et al., "Imaging Thermally Damaged Tissue by Polarization Sensitive Optical Coherence Tomography," Optics Express, vol. 3, No. 6, pp. 212-218, Sep. 14, 1998.

De Boer, Johannes F. et al., "Improved Signal-to-Noise Ratio in Spectral-Domain Compared with Time-Domain Optical Coherence Tomography," Optics Letters, vol. 28, No. 21, pp. 2067-2069, Nov. 1, 2003.

De Boer, Johannes F. et al., "Polarization Effects in Optical Coherence Tomography of Various Viological Tissues," IEEE Journal of Selected Topics in Quantum Electronics, vol. 5, No. 4, pp. 1200-1204, Jul./Aug. 1999.

Jerath, Maya R. et al. (1993) "Calibrated Real-Time Control of Lesion Size Based on Reflectance Images" Applied Optics vol. 32, No. 7, pp. 1200-1209.

Jesser, C. A., S. A. Boppart, et al. (1999). "High resolution imaging of transitional cell carcinoma with optical coherence tomography: feasibility for the evaluation of bladder pathology." British Journal of Radiology 72: 1170-1176.

Jiao, Shuliang et al., "Contrast Mechanisms in Polarization-Sensitive Mueller-Matrix Optical Coherence Tomography and Application in Burn Imaging," Applied Optics, vol. 42, No. 25, pp. 5191-5197, Sep. 1, 2003.

Jiao, Shuliang et al., "Depth-Resolved Two-Dimensional Stokes Vectors of Backscattered Light and Mueller Matrices of Biological Tissue Measured with Optical Coherence Tomography," Applied Optics, vol. 39, No. 34, pp. 6318-6324, Dec. 1, 2000.

Jiao, Shuliang et al., "Jones-Matrix Imaging of Biological Tissues with Quadruple-Channel Optical Coherence Tomography," Journal of Biomedical Optics, vol. 7, No. 3, pp. 350-358, Jul. 2002.

Jiao, Shuliang et al., "Optical-Fiber-Based Mueller Optical Coherence Tomography," Optics Letters, vol. 28, No. 14, pp. 1206-1208, Jul. 15, 2003.

Jiao, Shuliang et al., "Two-Dimensional Depth-Resolved Mueller Matrix of Blological Tissue Measured with Double-Beam Polarization-Sensitive Optical Coherence Tomography," Optics Letters, vol. 27, No. 2, pp. 101-103, Jan. 15, 2002.

Johnson, C. A., J. L. Keltner, et al. (2002). "Baseline visual field characteristics in the ocular hypertension treatment study." Ophthalmology 109(3): 432 7.

Johnston, Mark H.(2005) "Technology Insight: Ablative Techniques for Barrett's Esophagus—Current and Emerging Trends" www.Nature.com/clinicalpractice/gasthep.

Jones, R. C. (1941). "A new calculus for the treatment of optical systems I. Description and discussion of the calculus." Journal of the Optical Society of America 31(7): 488-493.

Jones, R. C. (1941). "A new calculus for the treatment of optical systems III. The Sohncke theory of optical activity." Journal of the Optical Society of America 31 (7): 500-503.

Jones, R. C. (1942). "A new calculus for the treatment of optical systems. IV." Journal of the Optical Society of America 32(8): 486-493.

Jones, R. C. (1947). "A New Calculus for the Treatment of Optical Systems .5. A More General Formulation, and Description of Another Calculus." Journal of the Optical Society of America 37(2): 107-110.

Jones, R. C. (1947). "A New Calculus for the Treatment of Optical Systems .6. Experimental Determination of the Matrix." Journal of the Optical Society of America 37(2): 110-112.

Jones, R. C. (1948). "A New Calculus for the Treatment of Optical Systems .7. Properties of the N-Matrices." Journal of the Optical Society of America 38(8): 671-685.

Jones, R. C. (1956). "New Calculus for the Treatment of Optical Systems .8. Electromagnetic Theory." Journal of the Optical Society of America 46(2): 126-131.

Joo, C. et al., "Spectral Domain optical coherence phase and mutiphoton microscopy," Optics Letters 32:623 (2007).

Joo, Chulmin et al., "Spectral-domain optical coherence phase microscopy for quantative phase-contrast imaging," Optics Letters, Aug. 15, 2005, vol. 30, No. 16, pp. 2131-2133.

Jopson, R. MThe ., L. E. Nelson, et al. (1999). "Measurement of second-order polarization-mode dispersion vectors in optical fibers." IEEE Photonics Technology Letters 11 (9): 1153-1155.

Jost, B. M., A. V. Sergienko, et al. (1998). "Spatial correlations of spontaneously down-converted photon pairs detected with a single-photon-sensitive CCD camera." Optics Express 3(2): 81-88.

Jun Zhang et al. "Full Range Polarization-Sensitive Fourier Domain Optical Coherence Tomography" Optics Express, vol. 12, No. 24. Nov. 29, 2004.

Kaplan, B., E. Compain, et al. (2000). "Phase-modulated Mueller ellipsometry characterization of scattering by latex sphere suspensions." Applied Optics 39 (4): 629-636.

Kass, M.A., D. K. Heuer, et al. (2002). "The Ocular Hypertension Treatment Study: a randomized trial determines that topical ocular hypotensive medication delays or prevents the onset of primary open-angle glaucoma." Archives of Ophthalmology 120(6): 701-13; discussion 829-30.

Kasuga, Y., J. Arai, et al. (2000). "Optical coherence tomography to confirm early closure of macular holes." American Journal of Ophthalmology 130(5): 675-6.

Kaufman, T., S. N. Lusthaus, et al. (1990). "Deep Partial Skin Thickness Burns—a Reproducible Animal-Model to Study Burn Wound-Healing." Burns 16(1): 13-16.

Kazovsky, L.G., et al., "Heterodyne Detection Through Rain, Snow, and Turbid Media: Effective Receiver Size at Optical Through Millimeter Wavelengths," Applied Optics, vol. 22, pp. 706-710, Mar. 1983.

Kemp, N. J., J. Park, et al. (2005). "High-sensitivity determination of birefringence in turbid media with enhanced polarization-sensitive optical coherence tomography." Journal of the Optical Society of America a-Optics Image Science and Vision 22(3): 552-560.

Kerrigan-Baurnrind, L. A., H. A. Quigley, et al. (2000). "Number of ganglion cells in glaucoma eyes compared with threshold visual field tests in the same persons." Investigative Ophthalmology & Visual Science 41(3): 741-8.

Kersey, L.G., et al., "Adaptive Polarization Diversity Receiver Configuration for Coherent Optical Fiber Communications," Electronics Letters, vol. 25, pp. 275-277, Feb. 1989.

(56)　　　　　References Cited

OTHER PUBLICATIONS

Kesen, M. R., G. L. Spaeth, et al. (2002). "The Heidelberg Retina Tomograph vs clinical impression in the diagnosis of glaucoma." American Journal of Ophthalmology 133(5): 613-6.

Khan, Misban Huzaira et al. (2005) "Intradermally Focused Infrared Laser Pulses: Thermal Effects at Defined Tissue Depths" Lasers in Surgery and Medicine vol. 36, pp. 270-280.

Kienle, A. and R. Hibst (1995). "A New Optimal Wavelength for Treatment of Port-Wine Stains." Physics in Medicine and Biology 40(10): 1559-1576.

Kienle, A., L. Lilge, et al. (1996). "Spatially resolved absolute diffuse reflectance measurements for noninvasive determination of the optical scattering and absorption coefficients of biological tissue." Applied Optics 35(13): 2304-2314.

Kiesslich, R. et al., (2004) "Confocal Laser Endoscopy for Diagnosing Intraepithelial Neoplasias and Colorectal Cancer in Vivo," Gastroenterology, vol. 127, No. 3, pp. 706-713.

Kim, B. Y. and S.S. Choi (1981). "Analysis and Measurement of Birefringence in Single-Mode Fibers Using the Backscattering Method." Optics Letters 6(11): 578-580.

Kim, B.M. et al. (1998) "Optical Feedback Signal for Ultrashort Laser Pulse Ablation of Tissue" Applied Surface Science vol. 127-129, pp. 857-862.

Kimel, S., L. O. Svaasand, et al. (1994). "Differential Vascular-Response to Laser Photothermolysis." Journal of Investigative Dermatology 103(5): 693-700.

Kinoshita, Masaya et al., "Optical Frequency-Domain Imaging Microprofilmetry with a Frequency-Domain Imaging Microprofilmetry with a Frequency-Tunable Liquid-Crystal FbryPerot Etalon Device," Applied Optics, vol. 38, No. 34, Dec. 1, 1999.

Kirkpatrick, J. Sean et al. "Optical Assessment of Tissue Mechanical Properties", Proceedings of the SPIE—The International Society for Optical Engineering SPIE—vol. 4001, 2000, pp. 92-101.

Kirkpatrick, Sean J. et al., "Laser speckle microstrain measurements in vascular tissue", SPIE, 1999, 3598:121-129.

Kirkpatrick, Sean J. et al., "Micromechanical behavior of cortical bone as inferred from laser speckle data", Journal of Biomedical Materials Research, 1998, 39(3):373-379.

Kloppenberg, F. W. H., G. Beerthuizen, et al. (2001). "Perfusion of burn wounds assessed by Laser Doppler Imaging is related to burn depth and healing time." Burns 27(4): 359-363.

Kneipp, Katrin et al.,"Single molecule detection using surface-enhanced Raman scattering (SERS)", Physical Review Letters 1997, 78 (9): 1667-1670.

Knighton, R. W. and X. R. Huang (2002). "Analytical methods for scanning laser polarimetry." Optics Express 10(21): 1179-1189.

Knighton, R. W., X. R. Huang, et al. (2002). "Analytical model of scanning laser polarimetry for retinal nerve fiber layer assessment." Investigative Ophthalmology & Visual Science 43(2): 383-392.

Knuettel, A. R. S., Joseph M.: Shay, M.; Knutson, Jay R. (1994). "Stationary low-coherence light imaging and spectroscopy using a CCD camera." Proc. SPIE, vol. 2135: p. 239-250.

Knuttel, A. and J.M. Schmitt (1993). "Stationary Depth-Profiling Reflectometer Based on Low-Coherence Interferometry." Optics Communications 102(3-4): 193-198.

Knuttel, A. and M. Boehlau-Godau (2000). "Spatially confined and temporally resolved refractive index and scattering evaluation in human skin performed with optical coherence tomography."Journal of Biomedical Optics 5(1): 83-92.

Knuttel, A., J.M. Schmitt, et al. (1994). "Low-Coherence Reflectometry for Stationary Lateral and Depth Profiling with Acoustooptic Deflectors and a Ccd Camera." Optics Letters 19(4): 302-304.

Ko, T et al., "Ultrahigh resolution in vivo versus ex vivo OCT imaging and tissue preservation", Conference on Lasers and electro-optics, 2001, pp. 252-253.

Eun, H. C. (1995). "Evaluation of skin blood flow by laser Doppler flowmetry. [Review] (151 refs]." Clinics in Dermatology 13(4): 337-47.

European Patent Office Search report for Application No. 01991092. 6-2305 dated Jan. 12, 2006.

European Patent Office. Extended European Search Report for Application No. 20167498.3 mailed on Jun. 30, 2020.

Evans, J. A., J.M. Poneros, et al. (2004). "Application of a histopathologic scoring system to optical coherence tomography (OCT) images to identify high-grade dysplasia in Barrett's esophagus." Gastroenterology 126(4): A5 I-A51.

Evans, John A. et al. (2006) "Optical Coherence Tomography to Identify Intramucosal Carcinoma and High-Grade Dysplasia in Barrett's Esophagus" Clinical Gastroenterology and Hepatology vol. 4, pp. 38-3.

Everett, M.J. et al., "Birefringence Characterization of Biological Tissue by Use of Optical Coherence Tomography," Optics Letters, vol. 23, No. 3, pp. 228-230, Feb. 1, 1998.

Facchini et al., "An endoscopic system for DSPI", Optik, 1993, 95(1):27-30.

Falk, Gary W. et al. (1997) "Surveillance of Patients with Barrett's Esophagus for Dysplasia and Cancer with Ballon Cytology" Gastrorenterology vol. 112, pp. 1787-1797.

Feldchtein, F. I., G. V. Gelikonov, et al. (1998). "Endoscopic applications of optical coherence tomography." Optics Express 3(6): 257-270.

Feldchtein, F. I., G. V. Gelikonov, et al. (1998). "In vivo OCT imaging of hard and soft tissue of the oral cavity." Optics Express 3(6): 239-250.

Feng et al., "Mesoscopic Conductors and Correlations in Laser Speckle Patters," Science, New Series, vol. 251, No. 4994, pp. 633-639 (Feb. 8, 1991).

Fercher, A. F., C. Hitzenberger, et al. (1991). "Measurement of Intraocular Optical Distances Using Partially Coherent Laser-Light." Journal of Modern Optics 38(7): 1327-1333.

Fercher, A. F., C. K. Hitzenberger, et al. (1993). "In-Vivo Optical Coherence Tomography." American Journal of Ophthalmology 116(1): 113-115.

Fercher, A. F., C. K. Hitzenberger, et al. (1994). In-vivo dual-beam optical coherence tomography. Proceedings of SPIE—The International Society for Optical Engineering.

Fercher, A. F., C. K. Hitzenberger, et al. (1995). "Measurement of Intraocular Distances by Backscattering Spectral Interferometry." Optics Communications 117(1-2): 43-48.

Fercher, A. F., C. K. Hitzenberger, et al. (1996). Ocular partial coherence interferometry. Proceedings of SPIE—The International Society for Optical Engineering.

Fercher, A. F., C. K. Hitzenberger, et al. (2000). "A thermal light source technique for optical coherence tomography." Optics Communications 185(1-3): 57-64.

Fercher, A. F., C. K. Hitzenberger, et al. (2001). "Numerical dispersion compensation for Partial Coherence Interferometry and Optical Coherence Tomography." Optics Express 9(12): 610-615.

Fercher, A. F., C. K. Hitzenberger, et al. (2002). "Dispersion compensation for optical coherence tomography depth-scan signals by a numerical technique." Optics Communications 204(1-6): 67-74.

Fercher, A. F., H. C. Li, et al. (1993). "Slit Lamp Laser-Doppler Interferometer." Lasers in Surgery and Medicine 13(4): 447-452.

Fercher, A. F., K. Mengedoht, et at. (1988). "Eye-Length Measurement by Interferometry with Partially Coherent-Light." Optics Letters, 13(3): 186-188.

Fercher, A. F., W. Drexler, et al. (1994). Measurement of optical distances by optical spectrum modulation. Proceedings of SPIE—The International Society for Optical Engineering.

Fercher, A. F., W. Drexler, et al. (1997). "Optical ocular tomography." Neuro-Ophthalmology 18(2): 39-49.

Fercher, A. F., W. Drexler, et al. (2003). "Optical coherence tomography—principles and applications." Reports on Progress in Physics 66(2): 239-303.

Fercher, Adolf, "Optical Coherence Tomography," Journal of Biomedical Optics, vol. 1, pp. 157-173, Apr. 1996.

Fernandez, Cabrera Delia et al. "Automated detection of retinal layer structures on optical coherence tomography images", Optics Express vol. 13, No. 25, Oct. 4, 2005, pp. 10200-10216.

Fernandez-Suarez, M. et al.,"Fluorescent Probes for Super-Resolution Imaging in Living Cells" Nature Reviews Molecular Cell Biology, vol. 9, Dec. 2008.

(56)         References Cited

OTHER PUBLICATIONS

Ferreir, L.A., et al., "Polarization-Insensitive Fiberoptic White-Light Interferometry," Optics Communications, vol. 114, pp. 386-392, Feb. 1995.

Ferro, P., M. Haelterman, et al. (1991). "All-Optical Polarization Switch with Long Low-Birefringence Fiber." Electronics Letters 27(16): 1407-1408.

Fetterman, M. R., D. Goswami, et al. (1998). "Ultrafast pulse shaping: amplification and characterization." Optics Express 3(10): 366-375.

Findl, O., W. Drexler, et al. (2001). "Improved prediction of intraocular lens power using partial coherence interferometry." Journal of Cataract and Refractive Surgery 27 (6): 861-867.

Flotte, Thomas J., "Pathology Correlations with Optical Biopsy Techniques," Annals of the New York Academy of Science, Wiley-Blackwell Publishing, Inc. SU, vol. 838, No. 1, Feb. 1, 1998, pp. 143-149.

Fork, R. L., C.H. B.Cruz, et al. (1987). "Compression of Optical Pulses to 6 Femtoseconds by Using Cubic Phase Compensation." Optics Letters 12(7): 483-485.

Foschini, G. J. and C. D. Poole (1991). "Statistical-Theory of Polarization Dispersion in Single-Mode Fibers." Journal of Lightwave Technology 9(11): 1439-1456.

Fox, J.A et al., "A New Galvanometric Scanner for Rapid tuning of C02 Lasers" New York, IEEE, US vol. Apr. 7, 1991.

Fox, Joshua et al., "Measuring Primate RNFL Thickness with OCT," IEEE Journal of Selected Topics in Quantum Electronics, IEEE Service Center, Piscataway, NJ, US, vol. 7, No. 6, Nov. 1, 2001.

Francia, C., F. Bruyere, et al. (1998). "PMD second-order effects on pulse propagation in single-mode optical fibers." Ieee Photonics Technology Letters 10(12): 1739-1741.

French, P.M.W. et al. (1993) "Continuous-wave Mode-Locked Cr+4 : YAG Laser" Optics Letters vol. 18, No. 1, pp. 39-41.

Fried, D., R. E. Glena, et al. (1995). "Nature of Light-Scattering in Dental Enamel and Dentin at Visible and near-Infrared Wavelengths." Applied Optics 34(7): 1278-1285.

Fried, Daniel et al., "Imaging Caries Lesions and Lesion Progression with Polarization Sensitive Optical Coherence Tomography," Journal of Biomedical Optics, vol. 7, No. 4, pp. 618-627, Oct. 2002.

Froehly, J. et al. (2003) "Multiplexed 3D Imaging Using Wavelength Encoded Spectral Interferometry: A Proof of Principle" Optics Communications vol. 222, pp. 127-136.

Fu L et al., "Double-Clad Photonic Crystal Fiber Coupler for compact Nonlinear Optical Microscopy Imaging," Optics Letters, OSA, Optical Society of America, vol. 31, No. 10, pp. 1471-1473, May 15, 2006.

Fujii, Yohji, "High-Isolation Polarization-Independent Optical Circulator," Journal of Lightwave Technology, vol. 9, pp. 1239-1243, Oct. 1991.

Fujimoto et al., "High Resolution in Vivo Intra-Arterial Imaging with Optical Coherence Tomography," Official Journal of the British Cardiac Society, vol. 82, pp. 128-133 Heart, 1999.

Fujimoto, J. G., M. E. Brezinski, et al. (1995). "Optical Biopsy and Imaging Using Optical Coherence Tomography." Nature Medicine 1(9): 970-972.

Fukasawa, A. and H. Iijima (2002). "Optical coherence tomography of choroidal osteoma." American Journal of Ophthalmology 133(3): 419-21.

Fymat, A. L. (1981). "High-Resolution Interferometric Spectrophotopolarimetry." Optical Engineering 20(1): 25-30.

Galtarossa, A., L. Palmieri, et al. (2000). "Measurements of beat length and perturbation length in long single-mode fibers." Optics Letters 25(6): 384-386.

Galtarossa, A., L. Palmieri, et al. (2000). "Statistical characterization of fiber random birefringence." Optics Letters 25(18): 1322-1324.

Gandjbakhche, A.H., P. Mills, et al. (1994). "Light-Scattering Technique for the Study of Orientation and Deformation of Red-Blood-Cells in a Concentrated Suspension." Applied Optics 33(6): 1070-1078.

Brink, H.B. K. and G. J. Vanblokland (1988). "Birefringence of the Human Foveal Area Assessed Invivo with Mueller-Matrix Ellipsometry." Journal of the Optical Society of America a-Optics Image Science and Vision 5(1): 49-57.

Brinkman, Ralf et al. (1996) "Analysis of Cavitation Dynamics During Pulsed Laser Tissue Ablation by Optical On-Line Monitoring" IEEE Journal of Selected Topics in Quantum Electronics vol. 2, No. 4, pp. 826-835.

Brinkmeyer, E. et al., "High-Resolution OCDR in Dispersive Wave-Guides," Electronics Letters, vol. 26, pp. 413-414, Mar. 1990.

Brinkmeyer, E., et al., "Efficient Algorithm for Non-Equidistant Interpolation of Sampled Data," Electronics Letters, vol. 28, p. 693, Mar. 1992.

Brosseau, C. and D. Bicout (1994). "Entropy Production in Multiple-Scattering of Light by a Spatially Random Medium." Physical Review E 50(6): 4997-5005.

Brown, Stanley B. et al. (2004) "The Present and Future Role of Photodynamic Therapy in Cancer Treatment" The Lancet Oncology vol. 5, pp. 497-508.

Burgoyne, C. F., D. E. Mercante, et al. (2002). "Change detection in regional and volumetric disc parameters using longitudinal confocal scanning laser tomography." Ophthalmology 109(3): 455-66.

Cameron, Brent D. et al., "Measurement and Calculation of the Two-Dimensional Backscattering Mueller Matrix of a Turbid Medium," Optics Letters, vol. 23, No. 7, pp. 485-487, Apr. 1, 1998.

Candido, R. and T. J. Allen (2002). "Haemodynamics in microvascular complications in type 1 diabetes." Diabetes-Metabolism Research and Reviews 18(4): 286-304.

Canto, M.I. et al., (1999) "Vital Staining and Barrett's Esophagus," Gastrointestinal Endoscopy, vol. 49, No. 3, Part 2, pp. S12-S16.

Cense, B., N. Nassif, et al. (2004). "Ultrahigh-Resolution High-Speed Retinal Imaging Using Spectral-Domain Optical Coherence Tomography." Optics Express 12(11): 2435-2447.

Cense, B., T. C. Chen, et al. (2004). "Thickness and birefringence of healthy retinal nerve fiber layer tissue measured with polarization-sensitive optical coherence tomography." Investigative Ophthalmology & Visual Science 45(8): 2606-2612.

Cense, Barry et al., "Spectral-domain polarization-sensitive optical coherence tomography at 850nm", Coherence Domain Optical Methods and Optical Coherence Tomography in Biomedicine.

Cense, Barry et al., "In Vivo Birefringence and Thickness Measurements of the Human Retinal Nerve Fiber Layer Using Polarization-Sensitive Optical Coherence Tomography," Journal of Biomedical Optics, vol. 9, No. 1, Jan./Feb. 2004, pp. 121-125.

Cense, Barry et al., "In Vivo Depth-Resolved Birefringence Measurements of the Human Retinal Nerve Fiber Layer by Polarization-Sensitive Optical Coherence Tomography," Optics Letters, vol. 27, No. 18, pp. 1610-1612, Sep. 15, 2002.

Chance,B., J. S. Leigh, et al. (1988). "Comparison of Time-Resolved and Time-Unresolved Measurements of Deoxyhemoglobin in Brain." Proceedings of the National Academy of Sciences of the United States of America 85(14): 4971-4975.

Chang, E. P., D. A. Keedy, et al. (1974). "Ultrastructures of Rabbit Corneal Stroma—Mapping of Optical and Morphological Anisotropies." Biochimica Et Biophysica Acta 343(3): 615-626.

Chaplin, N. T. and D. C. Lundy (2001). "The sensitivity and specificity of scanning laser polarimetry in the detection of glaucoma in a clinical setting." Ophthalmology 108 (5): 899-904.

Chartier, T., A. Hideur, et al. (2001). "Measurement of the elliptical birefringence of single-mode optical fibers." Applied Optics 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." Invest Ophthalmol Vis Sci 41: 775-782.

Chen, Z. P., T. E. Milner, et al. (1997). "Noninvasive imaging of in vivo blood flow velocity using optical Doppler tomography." Optics Letters 22(14): 1119-1121.

(56)　　　　　References Cited

OTHER PUBLICATIONS

Chen, Z. P., T. E. Milner, et al. (1997). "Optical Doppler tomographic imaging of fluid flow velocity in highly scattering media." Optics Letters 22(1): 64-66.

Chen, Z. P., Y. H. Zhao, et al. (1999). "Optical Doppler tomography." IEEE Journal of Selected Topics in Quantum Electronics 5(4): 1134-1142.

Cheong, W. F., S. A. Prahl, et al. (1990). "A Review of the Optical-Properties of Biological Tissues." IEEE Journal of Quantum Electronics 26(12): 2166-2185.

Chernikov, S. V., Y. Zhu, et al. (1997). "Supercontinuum self-Q-switched ytterbium fiber laser." Optics Letters 22(5): 298-300.

Chinn, S.R. et al., "Optical Coherence Tomography Using a Frequency-Tunable Optical Source," Optics Letters, vol. 22, pp. 340-342, Mar. 1997.

Cho, S. H., B. E. Bouma, et al. (1999). "Low-repetition-rate high-peak-power Kerr lens mode-locked Ti:Al/sub 2/0/sub3/ laser with a multiple-pass cavity." Optics Letters 24(6): 417-419.

Choma, M.A., C.H. Yarig, et al. (2003). "Instantaneous quadrature low-coherence interferometry with 3×3 fiber-optic couplers." Optics Letters 28(22): 2162-2164.

Choma, M.A., M. V. Sarunic, et al. (2003). "Sensitivity advantage of swept source and Fourier domain optical coherence tomography." Optics Express 11(18): 2183-2189.

Christens, Barry, W. A., W. J. Green, et al. (1996). "Spatial mapping of polarized light transmission in the central rabbit cornea." Experimental Eye Research 62(6): 651-662.

Chvapil, M., D. P. Speer, et al. (1984). "Identification of the depth of burn injury by collagen stainability." Plastic & Reconstructive Surgery 73(3): 438-41.

Cioffi, G. A. (2001). "Three common assumptions about ocular blood flow and glaucoma." Survey of Ophthalmology 45: S325-S331.

Clark et al., "Tracking Speckle Patterns with Optical Correlation", SPIE, 1992, 1772:77-87.

Coleman, A. L. (1999). "Glaucoma." Lancet 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." Am J Ophthalmol 126: 487-97.

Collaborative Normal-Tension Glaucoma Study Group (1998). "The effectiveness of intraocular pressure reduction in the treatment of normal-tension glaucoma." Am J Ophthalmol 126: 498-505.

Collaborative Normal-Tension Glaucoma Study Group (2001). "Natural History of Normal-Tension Glaucoma." Ophthalmology 108: 247-253.

Colston, B. W., M. J. Everett, et al. (1998). "Imaging of hard- and soft-tissue structure in the oral cavity by optical coherence tomography." Applied Optics 37(16): 3582-3585.

Colston, B. W., U.S. Sathyam, et al. (1998). "Dental OCT." Optics Express 3(6): 230-238.

Congdon, N. G., D.S. Friedman, et al: (2003). "Important causes of visual impairment in the world today." Jama-Journal of the American Medical Association 290(15): 2057-2060.

Constance, R. Chu et al. "Arthroscopic Microscopy of Articular Cartilage Using Optical Coherence Tomography," American Journal of Sports Medicine, American Orthopedic Society for Sports Medicine, Waltham, MA, vol. 32, No. 9, Apr. 1, 2004.

Australian Examiner's Report mailed May 27, 2008 for Australian patent application No. 2003210669.

Canadian Office Action dated Oct. 10, 2012 for 2,514,189.

Chinese Office Action dated Aug. 4, 2010 for CN 200780005949.9.

Chinese Office Action dated Aug. 4, 2010 for CN 200780016266.3.

European communication dated May 15, 2008 for European patent application No. 05819917.5.

European Communication Pursuant to EPC Article 94(3) for EP 07845206.7 dated Aug. 30, 2012.

European Extended Search Report mailed Mar. 26, 2013 for EP 09825421.1.

European Extended Search Report mailed on Feb. 1, 2013 for EP 12171521.3.

European Official Action dated Dec. 2, 2008 for EP 07718117.0.

Haggit et al., "Barrett's Esophaagus, Dysplasia, and Adenocarcinoma," Human Pathology, Saunders, Philadelphia, PA, US, vol. 25, No. 10, Oct. 1, 1994.

Haggitt, R. et al., "Barrett's Esophagus Correlation Between Mucin Histochemistry, Flow Cytometry, and Histological Diagnosis for Predicting Increased Cancer Risk," Apr. 1998, American Journal of Pathology, vol. 131, No. 1, pp. 53-61.

Hale, G. M. and M. R. Querry (1973). "Optical-Constants of Water in 200-Nm to 200-Mum Wavelength Region." Applied Optics 12(3): 555-563.

Hammer, D. X., R. D. Ferguson, et al. (2002). "Image stabilization for scanning laser ophthalmoscopy." Optics Express 10(26): 1542.

Hammer, Daniel X., et al., "Spectrally Resolved White-Light Interferometry for Measurement of Ocular Dispersion," Journal of the Optical Society of America A-Optics Image Science and Vision, vol. 16, pp. 2092-2102, Sep. 1999.

Hara, T., Y. Ooi, et al. (1989). "Transfer Characteristics of the Microchannel Spatial Light-Modulator." Applied Optics 28(22): 4781-4786.

Hardwick, R.H. et al., (1995) "c-erB-2 Overexpresssion in the Dysplasia/Carcinoma Sequence of Barrett's Oesophagus," Journal of Clinical Pathology, vol. 48, No. 2, pp. 129-132.

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.

Harland, C. C., S. G. Kale, et al. (2000). "Differentiation of common benign pigmented skin lesions from melanoma by high-resolution ultrasound." British Journal of Dermatology 143(2): 281-289.

Hartl, I., X. D. Li, et al. (2001). "Ultrahigh-resolution optical coherence tomography using continuum generation in an air-silica microstructure optical fiber." Optics Letters 26(9): 608-610.

Harvey, K.C., et al., "External-Cavity Diode-Laser Using a Grazing-Incidence Diffraction Grating," Optics Letters, vol. 16, pp. 910-912, Jun. 1991.

Hassenstein, A., A. A. Bialasiewicz, et al. (2000). "Optical coherence tomography in uveitis patients." American Journal of Ophthalmology 130(5): 669-70.

Hattenhauer, M. G., D. H. Johnson, et al. (1998). "The probability of blindness from open-angle glaucoma. [see comments]." Ophthalmology 105(11): 2099-104.

Hausler, G., J.M. Herrmann, et al. (1996). "Observation of light propagation in vol. scatterers with 10(11)-fold slow motion." Optics Letters 21(14): 1087-1089.

Jausler, Gerd et al., "Coherence Radar and Spectral Radar New Tools for Dermatological Diagnosis," Journal of Biomedical Optics, vol. 3, pp. 21-31, Jan. 1998.

Hazebroek, H.F. and A. A. Holscher (1973). "Interferometric Ellipsometry." Journal of Physics E-Scientific Instruments 6(9): 822-826.

Hazebroek, H.F. and W. M. Visser (1983). "Automated Laser Interferometric Ellipsometry and Precision Reflectometry." Journal of Physics E-Scientific Instruments 16(7): 654-661.

He, Z. Y., N. Mukohzaka, et al. (1997). "Selective image extraction by synthesis of the coherence function using two-dimensional optical lock-in amplifier with microchannel spatial light modulator." Ieee Photonics Technology Letters 9(4): 514-516.

Hee, M. R., C. A. Puliafito, et al. (1995). "Quantitative assessment of macular edema with optical coherence tomography." Archives of Ophthalmology 113(8): 1019-29.

Hee, M. R., C. A. Puliafito, et al. (1998). "Topography of diabetic macular edema with optical coherence tomography." Ophthalmology 105(2): 360-70.

Hee, M. R., J. A. Izatt, et al. (1993). "Femtosecond Transillumination Optical Coherence Tomography." Optics Letters 18(12): 950-952.

Hee, M. R., J. A. Izatt, et al. (1995). "Optical coherence tomography of the human retina." Archives of Ophthalmology 113(3): 325-32.

US 12,611,089 B2

Page 18

(56) References Cited

OTHER PUBLICATIONS

Hee, Michael R., et al., "Polarization-Sensitive Low-Coherence Reflectometer for Birefringence Characterization and Ranging," Journal of the Optical Society of America B (Optical Physics), vol. 9, p. 903-908, Jun. 1992.

Hell, S. et al., "Breaking the diffraction resolution limit by stimulated-emmision-stimulated-emission-depletion fluorescence microscopy," Optics Letters, 19:495 (1995) and Ground State Depletion (GSD).

Hell, S. et al., "Ground-State-Depletion fluorescence microscopy—a concept for breaking the diffraction resolution limit," Applied Physics B. 60:780 (1994) fluorescence microscopy, photo-activted localization microscopy (PALM).

Hellmuth, T. and M. Welle (1998). "Simultaneous measurement of dispersion, spectrum, and distance with a fourier transform spectrometer." Journal of Biomedical Optics 3(1): 7-11.

Hemenger, R. P. (1989). "Birefringence of a medium of tenuous parallel cylinders." Applied Optics 28(18): 4030-4034.

Henry, M. (1981). "Fresnel-Arago Laws for Interference in Polarized-Light—Demonstration Experiment." American Journal of Physics 49(7): 690-691.

Herz, P. R., Y. Chen, et al. (2004). "Micromotor endoscope catheter for in vivo, ultrahigh-resolution optical coherence tomography." Optics Letters 29(19): 2261-2263.

Hess, S.T., et al., "Ultra-high Resolution Imaging by Fluorescence Photoactivation Localization Microscopy," Biophysical Journal vol. 91, Dec. 2006, 4258-4272.

Hirakawa, H., H. Iijima, et al. (1999). "Optical coherence tomography of cystoid macular edema associated with retinitis pigmentosa." American Journal of Ophthalmology 128(2): 185-91.

Hitzenberger, C. K. and A. F. Fercher (1999). "Differential phase contrast in optical coherence tomography." Optics Letters 24(9): 622-624.

Hitzenberger, C. K., A. Baumgartner, et al. (1994). "Interferometric Measurement of Corneal Thickness with Micrometer Precision." American Journal of Ophthalmology 118(4): 468-476.

Hitzenberger, C. K., A. Baumgartner, et al. (1998). "Dispersion induced multiple signal peak splitting in partial coherence interferometry." Optics Communications 154 (4): 179-185.

Hitzenberger, C. K., A. Baumgartner, et al. (1999). "Dispersion effects in partial coherence interferometry: Implications for intraocular ranging." Journal of Biomedical Optics 4(1): 144-151.

Hitzenberger, C. K., M. Danner, et al. (1999). "Measurement of the spatial coherence of superluminescent diodes." Journal of Modern Optics 46(12): 1763-1774.

Hitzenberger, C. K., M. Sticker, et al. (2001). "Differential phase measurements in low-coherence interferometry without 2 pi ambiguity." Optics Letters 26(23): 1864-1866.

Hitzenberger, Christopher K. et al., "Measurement and Imaging of Birefringence and Optic Axis Orientation by Phase Resolved Polarization Sensitive Optical Coherence Tomography," Optics Express, vol. 9, No. 13, pp. 780-790, Dec. 17, 2001.

Ho, W. Y. et al. (2005) "115 KHz Tuning Repetition Rate Ultrahigh-Speed Wavelength-Swept Semiconductor Laser" Optics Letters col. 30, No. 23, pp. 3159-3161.

Hoeling, B. M., A. D. Fernandez, et al. (2000). "An optical coherence microscope for 3-dimensional imaging in developmental biology." Optics Express 6(7): 136-146.

Hoerauf, H., C. Scholz, et al. (2002). "Transscleral optical coherence tomography: a new imaging method for the anterior segment of the eye." Archives of Ophthalmology 120(6): 816-9.

Hoffmann, K., M. Happe, et al. (1998). "Optical coherence tomography (OCT) in dermatology." Journal of Investigative Dermatology 110(4): 583-583.

Hoh, S. T., D.S. Greenfield, et al. (2000). "Optical coherence tomography and scanning laser polarimetry in normal, ocular hypertensive, and glaucomatous eyes." American Journal of Ophthalmology 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." Journal. of Investigative Dermatology 104(5): 798-802.

Holland, A. J. A., H. C. O. Martin, et al. (2002). Laser Doppler imaging prediction of burn wound outcome in children: Burns 28(1): 11-17.

Hotate, Kazuo et al., "Optical Coherence Domain Reflectometry by Synthesis of Coherence Function," Journal of Lightwave Technology, vol. 11, pp. 1701-1710, Oct. 1993.

Hourdakis, C. J. and A. Perris (1995). "A Monte-Carlo Estimation of Tissue Optical-Properties for Use in Laser Dosimetry." Physics in Medicine and Biology 40(3): 351-364.

Hrabovsky, M., "Theory of speckle dispacement and decorrelation: application in mechanics", SPIE, 1998, 3479:345-354.

Hu, Z., F. Li, et al. (2000). "Wavelength-tunable narrow-linewidth semiconductor fiber-ring laser." IEEE Photonics Technology Letters 12(8): 977-979.

Huang, D., et al., "Optical Coherence Tomography," Science, vol. 254, pp. 1178-1181, Nov. 1991.

Yang, C., A. Wax, et al. (2001). "Phase-referenced interferometer with subwavelength and subhertz sensitivity applied to the study of cell membrane dynamics." Optics Letters 26(16): 1271-1273.

Yang, C.H., A. Wax, et al. (2000). "Interferometric phase-dispersion microscopy." Optics Letters 25(20): 1526-1528.

Yang, V. X. D., B. Qi, et al. (2003). "In vivo feasibility of endoscopic catheter-based Doppler optical coherence tomography." Gastroenterology 124(4): A49-A50.

Yang, V. X. D., M. L. Gordon, et al. (2002). "Improved phase-resolved optical Doppler tomography using the Kasai velocity estimator and histogram segmentation." Optics Communications 208(4-6): 209-214.

Yang, V. X. D., M. L. Gordon, et al. (2003). "High speed, wide velocity dynamic range Doppler optical coherence tomography (Part II): Imaging in vivo cardiac dynamics of Xenopus laevis." Optics Express 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." Optics Express 11(19): 2416-2424.

Yang, V.X.D., M.L. Gordon, et al., (2003). "High speed, wide velocity dynamic range Doppler optical coherence tomography (Part 1): System design, signal processing, and performance." Optics Express, 11(7): 794-809.

Yang, Ying et al., "Observations of Birefringence in Tissues from Optic-Fibre-Based Optical Coherence Tomography," Measurement Science and Technology, Nov. 2002, pp. 41-46.

Yao, G. and L. H. V. Wang (2000). "Theoretical and experimental studies of ultrasound-modulated optical tomography in biological tissue." Applied Optics 39(4): 659-664.

Yao, Gang et al., "Propagation of Polarized Light in Turbid Media: Simulated Animation Sequences," Optics Express, vol. 7, No. 5, pp. 198-203, Aug. 28, 2000.

Yao, Gang et al., "Two-Dimensional Depth-Resolved Mueller Matrix Characterization of Biological Tissue by Optical Coherence Tomography," Optics Letters, vol. 24, No. 8, pp. 537-239, Apr. 15, 1999.

Yaqoob et al. (Jun. 2002) "High-Speed Wavelength-Mutliplexed Fiber-Optic Sensors for Biomedicine," Sensors Proceedings of the IEEE, pp. 325-330.

Yasuno, Y. et al., "Birefringence Imaging of Human Skin by Polarization-Sensitive Spectral Interferometric Optical Coherence Tomography," Optics Letters, vol. 27, No. 20, pp. 1803-1805, Oct. 15, 2002.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Yazdanfar, S. and J. A. Izatt (2002). "Self-referenced Doppler optical coherence tomography." Optics Letters 27(23): 2085-2087.

Yazdanfar, S., A. M. Rollins, et al. (2000). "Imaging and velocimetry of the human retinal circulation with color Doppler optical coherence tomography." Optics Letters 25(19): 1448-1450.

(56)         References Cited

OTHER PUBLICATIONS

Yazdanfar, S., A. M. Rollins, et al. (2000). "Noninvasive imaging and velocimetry of human retinal blood flow using color Doppler optical coherence tomography." Investigative Ophthalmology & Visual Science 41(4): S548-S548.

Yazdanfar, S., A. M. Rollins, et al. (2003). "In vivo imaging of human retinal flow dynamics by color Doppler optical coherence tomography." Archives of Ophthalmology 121(2): 235-239.

Yazdanfar, S., C.H. Yang, et al. (2005). "Frequency estimation precision in Doppler optical coherence tomography using the Cramer-Rao lower bound." Optics Express 13(2): 410-416.

Yazdanfar, S., M. D. Kulkarni, et al. (1997). "High resolution imaging of in vivo cardiac dynamics using color Doppler optical coherence tomography." Optics Express 1 (13): 424-431.

Yelin et al., "Double-clad Fiber for Endoscopy" Optical Society of America; Optical Letters vol. 29, No. 20, Oct. 16, 2005; pp. 2408-2410.

Yelin, D. et al., "Three-dimensional imaging using spectral encoding heterodyne interferometry", Optics Letters, Jul. 15, 2005, vol. 30, No. 14, pp. 1794-1796.

Ymeti, A. et al., "Integration of microfluidics with a four-channel integrated optical Young interferometer immunosensor", Biosensors and Bioelectronics, Elsevier Science Publishers, 2005, pp. 1417-1421.

Yoden, K. et al., "An Approach to Optical Reflection Tomography Along the Geometrial Thickness," Optical Review, vol. 7, No. 5, Oct. 1, 2000.

Yonghua et al., "Real-Time Phase-Resolved Functional Optical Hilbert Transformation" Optics Letters, vol. 27, No. 2, Jan. 15, 2002.

Yoshimura, T. et al., "Statistical properties of dynamic speckles", J. Opt. Soc. Am A. 1986, 3(7): 1032-1054.

Youngquist, Robert C., et al., "Optical Coherence-Domain Reflectometry—A New Optical Evaluation Technique," Optics Letters, vol. 12, pp. 158-160, Mar. 1987.

Yu, P. et al. "Imaging of tumor necroses using full-frame optical coherence imaging", Proceedings of SPIE vol. 4956, 2003, pp. 34-41.

Yun et al., (2004) "Removing the Depth-Degeneracy in Optical Frequency Domain Imaging with Frequency Shifting," Optics Express, vol. 12, No. 20.

Yun, S. H., C. Boudoux, et al. (2003). "High-speed wavelength-swept semiconductor laser with a polygon-scanner-based wavelength filter." Optics Letters 28(20): 1981-1983.

Yun, S. H., C. Boudoux, et al. (2004). "Extended-cavity semiconductor wavelength-swept laser for biomedical imaging." Ieee Photonics Technology Letters 16(1): 293-295.

Yun, S. H., G. J. Teamney, et al. (2004). "Motion artifacts in optical coherence tomography with frequency-domain ranging." Optics Express 12(13): 2977-2998.

Yun, S. H., G. J. Teamney, et al. (2004). "Pulsed-source and swept-source spectral-domain optical coherence tomography with reduced motion artifacts." Optics Express 12(23): 5614-5624.

Yun, S. H., G. J. Teamey; et al. (2004). "Removing the depth-degeneracy in optical frequency domain imaging with frequency shifting." Optics Express 12(20): 4822-4828.

Yun, S.H. et al., "High-Speed Optical Frequency-Domain Imaging," Optics Express, vol. 11, No. 22, Nov. 3, 2003, pp. 2953-2963.

Yun, S.H. et al., "High-Speed Spectral-Domain Optical Coherence Tomography at 1.3 μm Wavelength," Optics Express, vol. 11, No. 26, Dec. 29, 2003, pp. 3598-3604.

Yun, S.H. et al., "Interrogation of Fiber Grating Sensor Arrays with a Wavelength-Swept Fiber Laser," Optics Letters, vol. 23, pp. 843-845, Jun. 1998.

Yun, S.H. et al., "Wavelength-Swept Fiber Laser with Frequency Shifted Feedback and Resonantly Swept Intra-Cavity Acoustooptic Tunable Filter," IEEE Journal of Selected Topics in Quantum Electronics, vol. 3, pp. 1087-1096, Aug. 1997.

Yung et al., "Phase-Domain Processing of Optical Coherence Tomography Images," Journal of Biomedical Optics, vol. 4 pp. 125-136, Jan. 1999.

Zagaynova, Elena et al., "Optical Coherence Tomography: Potentialities in Clinical Practice," Proceedings of SPIE, Aug. 20, 2004.

Zhang et al., "Full Range Polarization-Sensitive Fourier Domain Optical Coherence Tomography," Optics Express, Nov. 29, 2004, vol. 12, No. 24.

Zhang et al., (Sep. 2004) "Fourier Domain Functional Optical Coherence Tomography," Saratov Fall Meeting 2004, pp. 8-14.

Zhang Jun et al., "Full range polarization-sensitive Fourier domain optical coherence tomography", Optics Express, Nov. 29, 2004, vol. 12, No. 24, pp. 6033-6039.

Zhang, J., J. S. Nelson, et al. (2005). "Removal of a mirror image and enhancement of the signal-to-noise ratio in Fourier-domain optical coherence tomography using an electro-optic phase modulator." Optics Letters 30(2): 147-149.

Zhang, Jun et al., "Determination of Birefringence and Absolute Optic Axis Orientation Using Polarization-Sensitive Optical Coherence Tomography with PM Fibers," Optics Express, vol. 11, No. 24, Dec. 1, 2003, pp. 3262-3270.

Zhang, Y., M. Sato, et al. (2001). "Numerical investigations of optimal synthesis of several low coherence sources for resolution improvement." Optics Communications 192(3-6): 183-192.

Zhang, Y., M. Sato, et al. (2001). "Resolution improvement in optical coherence tomography by optimal synthesis of light-emitting diodes." Optics Letters 26(4): 205-207.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Zhao, Y. H., Z. P. Chen, et al. (2000). "Doppler standard deviation imaging for clinical monitoring of in vivo human skin blood flow." Optics Letters 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." Optics Letters 25(2): 114-116.

Sticker, Markus (2002) En Face Imaging of Single Cell layers by Differential Phase-Contrast Optical Coherence Microscopy) Optics Letters, col. 27, No. 13, Jul. 1, 2002.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Stoller, P., B. M. Kim, et al. (2002). "Polarization-dependent optical second-harmonic imaging of a rat-tail tendon." Journal of Biomedical Optics 7(2): 205-214.

Strasswimmer, John et al., "Polarization-Sensitive Optical Coherence Tomography of Invasive Basal Cell Carcinoma," Journal of Biomedical Optics, vol. 9, No. 2, Mar./Apr. 2004, pp. 292-298.

Summons to attend Oral Proceedings dated Oct. 9, 2009 for European Patent Application No. 06813365.1.

Sun, C. S. (2003). "Multiplexing of fiber-optic acoustic sensors in a Michelson interferometer configuration." Optics Letters 28(12): 1001-1003.

Swan et al., "High Resolution Spectral Self-Interference Fluorescence Microscopy," Proc. SPIE 4621, 2002, pp. 77-85.

Swan et al., "Toward nanometer-scale resolution in fluorescene microscopy using self-interference," IEEE Quantum Electronics 9:294 (2003).

Swan, et al., "Toward Nanometer-Scale Resolution in Fluorescence Microscopy using Spectral Self-Interference," IEEE Journal. Selected Topics in Quantum Electronics, 9 (2) 2003, pp. 294-300.

Swanson, E. A., J. A. Izatt, et al. (1993). "In-Vivo Retinal Imaging by Optical Coherence Tomography." Optics Letters 18(21): 1864-1866.

Swanson, E.A., et al., "High-Speed Optical Coherence Domain Reflectometry," Optics Letters, vol. 17, pp. 151-153, Jan. 1992.

Takada, K., A. Himeno, et al. (1991). "Phase-Noise and Shot-Noise Limited Operations of Low Coherence Optical-Time Domain Reflectometry." Applied Physics Letters 59(20): 2483-2485.

(56)  References Cited

OTHER PUBLICATIONS

Takada, K., et al., "High-Resolution OFDR with Incorporated Fiberoptic Frequency Encoder," IEEE Photonics Technology Letters, vol. 4, pp. 1069-1072, Sep. 1992.

Takada, Kazumasa et al., "Narrow-Band light Source with Acoustooptic Tunable Filter for Optical Low-Coherence Reflectometry," IEEE Photonics Technology Letters, vol. 8, pp. 658-660, May 1996.

Takada, Kazumasa et al., "New Measurement System for Fault Location in Optical Wave-Guide Devices Based on an Interometric-Technique," Applied Optics, vol. 26, pp. 1603-1606, May 1987.

Takagi, Yasunari, "Application of a microscope to Brillouin scattering spectroscopy", Review of Scientific Instruments, No. 12, Dec. 1992, pp. 5552-5555.

Takenaka, H. (1973). "Unified Formalism for Polarization Optics by Using Group-Theory I (Theory)." Japanese Journal of Applied Physics 12(2): 226-231.

Tanaka, Hajime et al., "New Method of Superheterodyne Light Beating Spectroscopy for Brillouin-Scattering Using Frequency-Tunable Lasers", Physical Review Letters 1995, 74 (9): 1609-1612.

Tang C. L. et al., "Transient effects in wavelength-modulated dye lasers", Applied Physics Letters, vol. 26, No. 9, May 1, 1975, pp. 534-537.

Tang C. L. et al., "Wide-band electro-optical tuning of semiconductor lasers", Applied Physics Letters, vol. 30, No. 2, Jan. 15, 1977, pp. 113-116.

Tanno, N., T. Ichimura, et al. (1994). "Optical Multimode Frequency-Domain Reflectometer." Optics Letters 19(8): 587-589.

Targowski, P., M. Wojtkowski, et al. (2004). "Complex spectral OCT in human eye imaging in vivo." Optics Communications 229(1-6): 79-84.

Tateda, Mitsuhiro et al., "Interferometric Method for Chromatic Dispersion Measurement in a Single-Mode Optical Fiber," IEEE Journal of Quantum Electronics, vol. 17, pp. 404-407, Mar. 1981.

Tearney et al., "High-Speed Phase—and Group Delay Scanning with a Grating Based Phase Control Delay Line," Optics Letters, vol. 22, pp. 1811-1813, Dec. 1997.

Tearney et al., "Spectrally encoded miniature endoscopy" Optical Society of America; Optical Letters vol. 27, No. 6, Mar. 15, 2002; pp. 412-414.

Tearney, et al., "In Vivo Endoscopic Optical Biopsy with Optical Coherence Tomography," Science, vol. 276, Jun. 1997.

Tearney, G. J. et al., "Atherosclerotic plaque characterization by spatial and temporal speckle pattern analysis", CLEO 2001, vol. 56, pp. 307-307.

Tearney, G. J., B. E. Bouma, et al. (1996). "Rapid acquisition of in vivo biological images by use of optical coherence tomography." Optics Letters 21(17): 1408-1410.

Tearney, G. J., B. E. Bouma, et al. (1997). "In vivo endoscopic optical biopsy with optical coherence tomography." Science 276(5321): 2037-2039.

Tearney, G. J., H. Yabushita, et al. (2003). "Quantification of macrophage content in atherosclerotic plaques by optical coherence tomography." Circulation 107(1): 113-119.

Tearney, G. J., I. K. Jang, et al. (2000). "Porcine coronary imaging in vivo by optical coherence tomography." Acta Cardiologica 55(4): 233-237.

Tearney, G. J., M. E. Brezinski, et al. (1995). "Determination of the refractive index of highly scattering human tissue by optical coherence tomography." Optics Letters 20(21): 2258-2260.

Tearney, G. J., M. E. Brezinski, et al. (1996). "Catheter-based optical imaging of a human coronary artery." Circulation 94(11): 3013-3013.

Tearney, G. J., M. E. Brezinski, et al. (1997). "In vivo endoscopic optical biopsy with optical coherence tomography." Science 276(5321): 2037-9.

Tearney, G. J., M. E. Brezinski, et al. (1997). "Optical biopsy in human gastrointestinal tissue using optical coherence tomography." American Journal of Gastroenterology. 92(10): 1800-1804.

Tearney, G. J., R.H. Webb, et al. (1998). "Spectrally encoded confocal microscopy." Optics Letters 23(15): 1152-1154.

Tearney, G. J., S. A. Boppart, et al. (1996). "Scanning single-mode fiber optic catheter-endoscope for optical coherence tomography (vol. 21, p. 543, 1996)." Optics Letters 21(12): 912-912.

Tearney, G.J. et al., "In Vivo Endoscopic Optical Biopsy with Optical Coherence Tomography," Science, vol. 276, No. 5321, Jun. 27, 1997, ("C6"), pp. 2037-2039.

Telle, M. John, et al., "New method for electro-optical tuning of tunable lasers", Applied Physics Letters, vol. 24, No. 2, Jan. 15, 1974, pp. 85-87.

Telle, M. John, et al., "Very rapid tuning of cw dye laser", Applied Physics Letters, vol. 26, No. 10, May 15, 1975, pp. 572-574.

Thompson et al., "Diffusive media characterization with laser speckle", Applied Optics, 1997, 36(16):3726-3734.

Thompson et al., "Imaging in scattering media by use of laser speckle", Opt. Soc. Am. A., 1997, 14(9):2269-2277.

Thompson, R. et al., "Precise nanometer localization analysis for individual fluorescent probes," Biophysical Journal 82:2775 (2002).

Thomsen, Sharon et al. (1990) "Microscopic Correlates of Macroscopic Optical Property Changes During Thermal Coagulation of Myocardium" SPIE vol. 1202, pp. 2-11.

Todoriovic, Milos et al., "Determination of Local Polarization Properties of Biological Samples in the Presence of Diattenuation by use of Mueller Optical Coherence Tomography," Optics Letters, vol. 29, No. 20, Oct. 15, 2004, pp. 2402-2404.

Toide, M., et al., "Two-Dimensional Coherent Dectection Imaging in Multiple Scattering Media Based the Directional Resolution Capability of the Optical Heterodyne Method," Applied Physics B (Photophysics and Laser Chemistry), vol. 852, pp. 391-394, 1991.

Tower, T. T. and R. T. Tranquillo (2001). "Alignment maps of tissues: I. Microscopic elliptical polarimetry." Biophysical Journal 81(5): 2954-2963.

Tower, T. T. and R. T. Tranquillo (2001). "Alignment maps of tissues: II. Fast harmonic analysis for imaging." Biophysical Journal 81(5): 2964-2971.

Tripathi, Ranu et al., "Spectral Shaping for Non-Gaussian Source Spectra in Optical Coherence Tomography," Optics Letters, vol. 27, No. 6, pp. 406-408, Mar. 15, 2002.

Troy, T. L. and S. N. Thennadil (2001). "Optical properties of human skin in the near infrared wavelength range of 1000 to 2200 nm." Journal of Biomedical Optics 6 (2): 167-176.

Sankaran, V., J. T. Walsh, et al. (2000). "Polarized light propagation through tissue phanto, ehms containing densely packed scatterers." Optics Letters 25(4): 239-241.

Sankaran, V., M. J. Everett, et al. (1999). "Comparison of polarized-light propagation in biological tissue and phantoms." Optics Letters 24(15): 1044-1046.

Sarunic, M. V., M.A. Choma, et al. (2005). "Instantaneous complex conjugate resolved spectral domain and swept-source OCT using 3×3 fiber couplers." Optics Express 13(3): 957-967.

Sathyam, U.S., B. W. Colston, et al. (1999). "Evaluation of optical coherence quantitation of analytes in turbid media by use of two wavelengths." Applied Optics 38(10): 2097-2104.

Saxer et al., "High Speed Fiber-Based Polarization-Sensitive Optical Coherence Tomography of in Vivo Human Skin," Optical Society of America, vol. 25, pp. 1355-1357, Sep. 2000.

Schmitt, M. Joseph et al. "OCT elastography: imaging microscopic deformation and strain of tissue", Optics Express, vol. 3, No. 6, Sep. 14, 1998, pp. 199-211.

Schmitt, J.M. et al., (1999) "Speckle in Optical Coherence Tomography: An Overview", SPIE vol. 3726, pp. 450-461.

Schmitt, J.M. (1997). "Array detection for speckle reduction in optical coherence microscopy." Physics in Medicine and Biology 42(7): 1427-1439.

Schmitt, J.M. (1999). "Optical coherence tomography (OCT): A review." Ieee Journal of Selected Topics in Quantum Electronics 5(4): 1205-1215.

Schmitt, J.M. and A. Knuttel (1997). "Model of optical coherence tomography of heterogeneous tissue." Journal of the Optical Society of America a-Optics Image Science and Vision 14(6): 1231-1242.

Schmitt, J.M et al., "Cross-Polarized Backscatter in Optical Coherence Tomography of Biological Tissue," Optics Letters, vol. 23, No. 13, pp. 1060-1062, Jul. 1, 1998.

(56) References Cited

OTHER PUBLICATIONS

Schmitt, J.M., et al., "Measurement of Optical-Properties of Biological Tissues By Low-Coherence Reflectometry," Applied Optics, vol. 32, pp. 6032-6042, Oct. 1993.

Schmitt, J.M., M. J. Yadlowsky, et al. (1995). "Subsurface Imaging of Living Skin with Optical Coherence Microscopy." Dermatology. 191(2): 93-98.

Schmitt, J.M., S. H. Xiang, et al. (1998). "Differential absorption imaging with optical coherence tomography." Journal of the Optical Society of America a-Optics Image Science and Vision 15(9):2288-2296.

Schmitt, J.M., S. H. Xiang, et al. (1999). "Speckle in optical coherence tomography." Journal of Biomedical Optics 4(1): 95-105.

Schmitt, J.M., S. L. Lee, et al. (1997). "An optical coherence microscope with enhanced resolving power in thick tissue." Optics Communications 142(4-6): 203-207.

Schoenenberger, Klaus et al., "Mapping of Birefringence and Thermal Damage in Tissue by use of Polarization-Sensitive Optical Coherence Tomography," Applied Optics, vol. 37, No. 25, pp. 6026-6036, Sep. 1, 1998.

Seltzer et al., (1991) "160nm Continuous Tuning of a MQW Laser in an External Cavity Across the Entire 1.3 um Communications Window," Electronic Letters, vol. 27, pp. 95-96.

Sennaroglu, Alphan at al. (1995) "Efficient Continuous-Wave Chromium-Doped YAG Laser" Journal of Optical Society of America vol. 12, No. 5, pp. 930-937.

Seok, H. Yun et al., "Comprehensive Volumetric Optical Microscopy in Vivo," Nature Medicine, vol. 12, No. 12, Jan. 1, 2007.

Sepchler, Stuart Jon. (1997) "Barrett's Esophagus: Should We Brush off this Balloning Problem?" Gastroenterology vol. 112, pp. 2138-2152.

Shapo et al., "Intravascular strain imaging: Experiments on an Inhomogeneous Phantom", IEEE Ultrasonics Symposium 1996, 2:1177-1180.

Shapo et al., "Ultrasonic displacement and strain imaging of coronary arteries with a catheter array", IEEE Ultrasonics Symposium 1995, 2:1511-1514.

Sharma, P. et al.(2003) "Magnification Chromoendoscopy for the Detection of Intestinal Metaplasia and Dysplasia in Barrett's Oesophagus" Gut vol. 52, pp. 24-27.

Shen et al., "Ex Vivo Histology-Correlated Optical Coherence Tomography in the Dectection of Transmural Inflammation in Crohn's Disease," Clinical Gastroenterology and Heptalogy, vol. 2, No. 9, Sep. 1, 2004.

Shen et al., "In Vivo Coloscopic Optical Coherence Tomography for Transmural Inflammation in Inflammatory Bowel Disease," Clinical Gastroenterology and Hepatology, American Gastroenterological Association, US, vol. 2, No. 12, Dec. 1, 2004.

Shi, H., I. Nitta, et al. (1999). "Demonstration of phase correlation in multiwavelength mode-locked semiconductor diode lasers." Optics Letters 24(4): 238-240.

Shi, H., J. Finlay, et al. (1997). "Multiwavelength 10-GHz picosecond pulse generation from a single-stripe semiconductor diode laser:" Ieee Photonics Technology Letters 9(11): 1439-1441.

Shim, M.G. et al., "Study of Fiber-Optic Probes For In Vivo Medical Raman Spectroscopy" Applied Spectroscopy, vol. 53, No. 6, Jun. 1999.

Shribak, Michael et al., Techniques for Fast and Sensitive Measurements of Two-Dimensional Birefringence Distributions•,,, Applied Optics, vol. 42, No. 16, Jun. 1, 2003, pp. 3009-3017.

Siavash et al., "Self-Referenced Doppler Optical Coherence Tomography" Optics Letters, vol. 27, No. 23, Dec. 1, 2002.

Siavash Yazdanfar et al., "In Vivo imaging in blood flow in human retinal vessels using color Doppler optical coherence tomography", SPIE, 1999 vol. 3598, pp. 177-184.

Silberberg, Y., et al., "Passive-Mode Locking of a Semiconductor Diode-Laser," Optics Letters, vol. 9, pp. 507-509, Nov. 1984.

Silva et al., "Extended Range, Rapid Scanning Optical Delay Line for Biomedical Interferometric Imaging," Electronics Letters, IEEE Stevenage, GB vol. 35, No. 17, Aug. 19, 1999.

Simon, R. (1982). "The Connection between Mueller and Jones Matrices of Polarization Optics." Optics Communications 42(5): 293-297.

Sir Randall, John et al., "Brillouin scattering in systems of biological significance", Phil. Trans. R. Soc. Lond. A 293, 1979, pp. 341-348.

Smith, Montgomery L., et al., "Absolute Displacement Measurements Using Modulation of the Spectrum of White-Light in a Michelson Interferometer," Applied Optics, vol. 28, pp. 3339-3342, Aug. 1989.

Smith, P. J.M., (2000) "Variable-Focus Microlenses as a Potential Technology for Endoscopy." SPIE (vol. 919), USA pp. 187-192.

Smithies, D. J., T. Lindmo, et al. (1998). "Signal attenuation and localization in optical coherence tomography studied by Monte Carlo simulation." Physics in Medicine and Biology 43(10): 3025-3044.

Soetikno, Roy M. et al. (2003) "Endoscopic Mucosal resection" Gastrointestinal Endoscopy vol. 57, No. 4, pp. 567-579.

Somervell, A.RD. et al., "Direct Measurement of Fringe Amplitude and Phase Using a Heterodyne Interferometer Operating in Broadband Light," Elsevier, Optics Communications, Oct. 2003.

Sonehara, Tsuyoshi et al., "Forced Brillouin Spectroscopy Using Frequency-Tunable Continuous-Wave Lasers", Physical Review Letters 1995, 75 (23): 4234-4237.

Sonnenschein, C.M., et al., "Signal-To-Noise Relationships for Coaxial Systems that Heterodyne Backscatter from Atmosphere," Applied Optics, vol. 10, pp. 1600-1604, Jul. 1971.

Sorin, W. V. and D. F. Gray (1992). "Simultaneous Thickness and Group Index Measurement Using Optical Low-Coherence Reflectometry." Ieee Photonics Technology Letters 4(1): 105-107.

Sorin, W.V., et al., "A Simple Intensity Noise-Reduction Technique for Optical Low-Coherence Reflectometry," IEEE Photonics Technology Letters, vol. 4, pp. 1404-1406, Dec. 1992.

Sorin, W.V., et al., "Measurement of Rayleigh Backscattering at 1.55 mu m with 32 mu m Spatial Resolution," IEEE Photonics Technology Letters, vol. 4, pp. 374-376, Apr. 1992.

Srinivas, Shyam M. et al., "Determination of Burn Depth by Polarization-Sensitive Optical Coherence Tomography," Journal of Biomedical Optics, vol. 9, No. 1, Jan./Feb. 2004, pp. 207-212.

Stewart, C.J. et al., "A comparison of two laser-based methods for determination of burn scar perfusion: Laser Doppler versus laser speckle imaging", Elsevier Ltd., 2005, vol. 31, pp. 744-752.

Sticker, M., C. K. Hitzenberger, et al. (2001). "Quantitative differential phase measurement and imaging in transparent and turbid media by optical coherence tomography." Optics Letters 26(8): 518-520.

Sticker, M., M. Pircher, et al. (2002). "En face imaging of single cell layers by differential phase-contrast optical coherence microscopy." Optics Letters 27(13): 1126-1128.

Japanese Notice of Reasons for Rejection dated May 21, 2012 for JP 2008-551523.

Japanese Notice of Reasons for Rejection dated May 8, 2012 for JP 2008-533727.

Japanese Notice of Reasons for Rejections dated Nov. 27, 2012 for JP 2009-554772.

Japanese Notice of Reasons for Rejections dated Nov. 9, 2012 for JP 2007-530134.

Japanese Notice of Reasons for Rejections dated Oct. 10, 2012 for 2008-553511.

Japanese Notice of Reasons for Rejections dated Oct. 11, 2012 for JP 2008-533712.

Japanese Notice of Reasons for Rejections dated Oct. 2, 2012 for 2007-543626.

Japanese Office Action dated Apr. 13, 2010 for Japanese Patent Application No. 2007-515029.

Korean Office Action dated May 25, 2012 for KR 10-2007-7008116.

International Search Report and Written Opinion dated Aug. 11, 2008 for International Application No. PCT/US2008/058703.

International Search Report and Written Opinion dated Jul. 17, 2008 for International Application No. PCT/US2008/057450.

International Search Report and Written Opinion for PCT/US2007/081982 dated Oct. 19, 2007.

(56)                    References Cited

OTHER PUBLICATIONS

Notice of Allowance dated Oct. 3, 2007 for U.S. Appl. No. 11/225,840.
Notice of Allowance mailed Jun. 4, 2008 for U.S. Appl. No. 11/174,425.
Notice of Reasons for Rejection dated Feb. 19, 2013 for JP 2008-507983.
Notice of Reasons for Rejection dated Feb. 5, 2013 for JP 2008-509233.
Notice of Reasons for Rejection mailed Apr. 16, 2013 for JP 2009-510092.
Notice of Reasons for Rejection mailed Dec. 2, 2008 for Japanese Patent Application No. 200533782.
Notification Concerning Transmittal of International Preliminary Report on Patentability dated Oct. 13, 2005 for PCT/US04/10152.
Notification of the International Preliminary Report on Patentability mailed Oct. 21, 2005.
Office Action dated Apr. 15, 2009 for U.S. Appl. No. 12/205,775.
Office Action dated Apr. 17, 2009 for U.S. Appl. No. 11/537,343.
Office Action dated Apr. 8, 2010 of U.S. Appl. No. 11/414,564.
Office Action dated Aug. 10, 2007 for U.S. Appl. No. 10/997,789.
Office Action dated Aug. 13, 2009 for U.S. Appl. No. 10/136,813.
Office Action dated Aug. 18, 2009 for U.S. Appl. No. 12/277,178.
Office Action dated Aug. 21, 2008 for U.S. Appl. No. 11/505,700.
Office Action dated Aug. 21, 2008 for U.S. Appl. No. 11/956,079.
Office Action dated Aug. 24, 2006 for U.S. Appl. No. 10/137,749.
Office Action dated Aug. 25, 2008 for U.S. Appl. No. 11/264,655.
Office Action dated Aug. 27, 2010 for U.S. Appl. No. 11/569,790.
Office Action dated Aug. 31, 2010 for U.S. Appl. No. 11/677,278.
Office Action dated Aug. 5, 2010 for U.S. Appl. No. 11/623,852.
Office Action dated Aug. 6, 2009 for U.S. Appl. No. 11/624,455.
Office Action dated Dec. 15, 2009 for U.S. Appl. No. 11/549,397.
Office Action dated Dec. 18, 2006 for U.S. Appl. No. 10/501,276.
Office Action dated Dec. 18, 2007 for U.S. Appl. No. 11/288,994.
Office Action dated Dec. 21, 2007 for—U.S. Appl. No. 11/264,655.
Office Action dated Dec. 23, 2008 for U.S. Appl. No. 11/780,261.
Office Action dated Dec. 6, 2006 for U.S. Appl. No. 10/997,789.
Office Action dated Dec. 9, 2008 for U.S. Appl. No. 09/709,162.
Office Action dated Feb. 17, 2009 for U.S. Appl. No. 11/211,483.
Office Action dated Feb. 18, 2009 for U.S. Appl. No. 11/285,301.
Office Action dated Feb. 18, 2009 for U.S. Appl. No. 11/697,012.
Office Action dated Feb. 2, 2007 for U.S. Appl. No. 11/174,425.
Office Action dated Feb. 23, 2009 for U.S. Appl. No. 11/956,129.
Office Action dated Feb. 4, 2008 for U.S. Appl. No. 10/861,179.
Office Action dated Jan. 10, 2008 for U.S. Appl. No. 11/410,937.
Office Action dated Jan. 10, 2008 for U.S. Appl. No. 11/435,228.
Office Action dated Jan. 11, 2008 for U.S. Appl. No. 11/445,990.
Abbas, G.L., V.W.S. Chen, et al.,"Local-Oscillator Excess-Noise Suppression for Homodyne and Heterodyne-Dectection," Optics Letters, vol. 8, pp. 419-421, Aug. 1983 issue.
Acioli, L. H., M. Ulman, et al. (1991). "Femtosecond Temporal Encoding in Barium-Titanate." Ogtics Letters 16(24): 1984-1986.
Adams, S.B. Jr. et al., "The use of polarization sensitive optical coherence tomography and elastography to assess connective tissue", Optical Soc. of American Washington 2002, p. 3.
Adrain, Alyn L. et al. (1997) "High-Resolution Endoluminal Sonography is a Sensitive Modality for the Identification of Barrett's Meaplasia" Gastrointestinal Endoscopy vol. 46, No. 2, pp. 147-151.
Agrawal, G.P., "Population Pulsations and Nondegenerate 4-Wave Mixing in Semiconductor-Lasers and Amplifiers," Journal Of The Optical Society Of America B-Optical Physics, vol. 5, pp. 147-159, Jan. 1998.
Aigouy, L., A. Lahrech, et al. (1999). "Polarization effects in apertureless scanning near-field optical microscopy: an experimental study." Optics Letters 24(4): 187-189.
Aizu, Yet al. (1991) "Bio-Speckle Phenomena and Their Application to the Evaluation of Blood Flow" Optics and Laser Technology, vol. 23, No. 4, Aug. 1, 1991.
Akiba, M., K. P. Chan, et al. (2003). "Full-field optical coherence tomography by two-dimensional heterodyne detection with a pair of CCD cameras." Optics Letters 28(10): 816-818.

Akiba, Masahiro et al. "En-face optical coherence imaging for three-dimensional microscopy", SPIE, 2002, pp. 8-15.
Akkin, T., D. P. Dave, et al. (2003). "Imaging tissue response to electrical and photothermal stimulation with nanometer sensitivity." Lasers in Surgery and Medicine 33(4): 219-225.
Akkin, T., D. P. Dave, et al. (2003). "Surface analysis using phase sensitive optical low coherence reflectometry." Lasers in Surgery and Medicine: 4-4.
Akkin, T., D. P. Dave, et al. (2004). "Detection of neural activity using phase-sensitive optical low-coherence reflectometry." Optics Express 12(11): 2377-2386.
Akkin, T., T. E. Milner, et al. (2002). "Phase-sensitive measurement of birefringence change as an indication of neural functionality and diseases." Lasers in Surgery and Medicine: 6-6.
Anderson, R. Rox et al. (1983) "Selective Photothermolysis Precise Microsurgery by Selective Absorption of Pulsed Radiation" Science vol. 220, No. 4596, pp. 524-527.
Andretzky, P., et al., "Optical Coherence Tomography by Spectral Radar: Improvement of Signal-to-Noise Ratio," The International Society for Optical Engineering, USA, vol. 3915, 2000.
Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." Proceedings of SPIE—The International Society for Optical Engineering 3567: pp. 78-87.
Antcliff, R. J., M. R. Stanford, et al. (2000). "Comparison between optical coherence tomography and fundus fluorescein angiography for the detection of cystoid macular edema in patients with uveitis." Ophthalmology 107(3): 593-9.
Antcliff, R. J., T. J. ffytche, et al. (2000). "Optical coherence tomography of melanocytoma." American Journal of Ophthalmology 130(6): 845-7.
Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." Physics in Medicine and Biology 40(9): 1451-1465.
Anvari, B., T. E. Milner, et al. (1995). "Selective Cooling of Biological Tissues—Application for Thermally Mediated Therapeutic Procedures." Physics in Medicine and Biology 40(2): 241-252.
Arend, O., M. Ruffer, et al. (2000). "Macular circulation in patients with diabetes mellitus with and without arterial hypertension." British Journal of Ophthalmology 84(12): 1392-1396.
Arimoto, H. and Y. Ohtsuka (1997). "Measurements of the complex degree of spectral coherence by use of a wave-front-folded interferometer." Optics Letters 22(13): 958-960.
Athey, B.D. et al., "Development and Demonstration of a Networked Telepathology 3-D Imaging, Databasing, and Communication System," 1998 ("C2"), pp. 5-17.
Azzolini, C., F. Patelli, et al. (2001). "Correlation between optical coherence tomography data and biomicroscopic Interpretation of idiopathic macular hole." American Journal of Ophthalmology 132(3): 348-55.
Baba, T., K. Ohno-Matsui, et al. (2002). "Optical coherence tomography of choroidal neovascularization in high myopia." Acta Ophthalmological Scandinavica 80(1): 82-7.
Bachmann, A.H. et al., "Heterodyne Fourier Domain Optical Coherence Tomography for Full Range Probing with High Axial Resolution," Optics Express, OSA, vol. 14, No. 4, Feb. 20, 2006.
Bail, M.A. H., Gerd; Herrmann, Juergen M.; Lindner, Michael W.; Ringler, R. (1996). "Optical coherence tomography with the "spectral radar": fast optical analysis in volume scatterers by short-coherence interferometry." Proc. SPIE, 2925: p. 298-303.
Bailey, B. et al., "Enhancement of Axial Resolution in Fluorescence Microscopy by Standing-Wave Excitation," Nature 366:44 (1993).
Ballif, J., et al., "Rapid and Scalable Scans at 21 m/s in optical Low-Coherence Reflectometry," Optics Letters, vol. 22, pp. 757-759, Jun. 1997.
Baney, D. M. and W. V. Sorin (1993). "Extended-Range Optical Low-Coherence Reflectometry Using a Recirculating Delay Technique." IEEE Photonics Technology Letters 5(9): 1109-1112.

(56) References Cited

OTHER PUBLICATIONS

Baney, D. M., B. Szafraniec, et al. (2002). "Coherent optical spectrum analyzer." Ieee Photonics Technology Letters 14(3): 355-357.

Barakat, R. (1981). "Bilinear Constraints between Elements of the 4by4 Mueller-Jone Transfer-Matrix of Polarization Theory." Optics Communications 38(3): 159-161.

Barakat, R. (1993). "Analytic Proofs of the Arago-Fresnel Laws for the Interference of Polarized-Light." Journal of the Optical Society of America a-Optics Image Science and Vision 10(1): 180-185.

Barakat, Richard, "Statistics of the Stokes Parameters," J. Opt. Soc. Am. B., vol. 4, No. 7, pp. 1256-1263, Jul. 1987.

Barastathis, G. and D. J. Brady (1999). "Multidimensional tomographic imaging using volume holography." Proceedings of the Ieee 87(12): 2098-2120.

Bardal, S., A. Kamal, et al. (1992). "Photoinduced Birefringence-in Optical Fibers—a Comparative-Study of Low-Birefringence and High-Birefringence Fibers." Optics Letters 17(6): 411-413.

Barfuss et al. (1989) "Modified Optical Frequency Domain Reflectometry with High spatial Resolution for Components of Integrated Optic Systems," Journal of Lightwave Technology, IEEE, vol. 7, No. 1.

Barfuss, H., et al., "Modified Optical Frequency-Domain Reflectometry with High Spatial-Resolution for Components of Integrated Optic Systems." Journal of Lightwave Technology, vol. 7, pp. 3-10, Jan. 1989.

Barr, H et al. (2005) "Endoscopic Therapy for Barrett's Oesophagus" Gut vol. 54:875-884.

Barsky, S. H., S. Rosen, et al. (1980). "Nature and Evolution of Port Wine Stains—Computer-Assisted Study." Journal of Investigative Dermatology 74(3): 154-157.

Barton, J. K., A. J. Welch, et al. (1998). "Investigating pulsed dye laser-blood vessel interaction with color Doppler optical coherence tomography." Optics Express 3.

Barton, J. K., A. Rollins, et al. (2001). "Photothermal coagulation of blood vessels: a comparison of high-speed optical coherence tomography and numerical modelling." Physics in Medicine and Biology 46.

Barton, J. K., J. A. Izatt, et al. (1999). "Three-dimensional reconstruction of blood vessels from in vivo color Doppler optical coherence tomography images." Dermatology 198(4): 355-361.

Bashanksy, M.M.D. Duncan, et al. (1997) "Subsurface defect detection in ceramics by high-speed high-resolution optical coherent tomography." Optics Letters 22 (1): 61-63.

Bashkansky, et al., "Signal Processing for Improving Field Cross-Correlation Function in Optical Coherence Tomography," Optics & Photonics News, vol. 9, pp. 8137-8138, May 1998.

Bashkansky, M. and J. Reintjes (2000). "Statistics and reduction of speckle in optical coherence tomography." Optics Letters 25(8): 545-547.

Baumgartner, A., C. K. Hitzenberger, et al. (1998). "Signal and resolution enhancements in dual beam optical coherence tomography of the human eye." Journal of Biomedical Optics 3(1): 45-54.

Baumgartner, A., C. K. Hitzenberger, et al. (2000). "Resolution-improved dual-beam and standard optical coherence tomography: a comparison." Graefes Archive for Clinical and Experimental Ophthalmology 238(5): 385-392.

Baumgartner, A., S. Dichtl, et al. (2000). "Polarization-sensitive optical coherence tomography of dental structures." Caries Research 34(1): 59-69.

Baxter, "Image Zooming," Jan. 25, 2005, retrieved from the Internet.

Gang, Yao et al., "Monte Carlo Simulation of an Optical Coherene Tomography Signal in Homogenous Turbid Media," Physics in Medicine and Biology, 1999.

Ganz, Robert A. et al. (2004) "Complete Ablation of Esophageal Epithelium with a Balloon-based Bipolar Electrode: A Phased Evaluation in the Porcine and in the Human Esophagus" Gastrointestinal Endoscopy vol. 60, No. 6, pp. 1002-1010.

Garcia, N. and M. Nieto-Vesperinas (2002). "Left-handed materials do not make a perfect lens." Physical Review Letters 88(20).

Ge Z et al., "Identification of Colonic Dysplasia and Neoplasia by Diffuse Reflectance Spectroscopy and Pattern Recognition Techniques," Applied Spectroscopy, The Society for Applied Spectroscopy, vol. 52, No. 6, Jun. 1, 1998.

Geddert, H. et al., "Expression of Cyclin B1 in the Metaplasia-Dysphasia-Carcinioma Sequence of Barrett Esophagus," Jan. 2002, Cancer, vol. 94, No. 1, pp. 212-218.

Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.

Gelikonov, V. M., G. V. Gelikonov, et al. (1995). "Coherent Optical Tomography of Microscopic Inhomogeneities in Biological Tissues." Jetp Letters 61(2): 158-162.

Georgakoudi, Irene et al. (2001) "Fluorescence, Reflectance, and Light-Scattering Spectroscopy for Evaluating Dysplasia in Patients with Barrett's Esophagus" Gastroenterology vol. 120, pp. 1620-1629.

George, N. and A. Jain (1973). "Speckle Reduction Using Multiple Tones of Illumination." Applied Optics 12(6): 1202-1212.

Gibson, G. N., R. Klank, et al. (1996). "Electro-optically cavity-dumped ultrashort-pulse Ti:sapphire oscillator." Optics Letters 21(14): 1055.

Gil, J. J. (2000). "Characteristic properties of Mueller matrices." Journal of the Optical Society of America a-Optics Image Science and Vision 17(2): 328-334.

Gil, J. J. and E. Bemabeu (1987). "Obtainment of the Polarizing and Retardation Parameters of a Nondepolarizing Optical-System from the Polar Decomposition of Its Mueller Matrix." Optik 76(2): 67-71.

Gladkova, N. D., G. A. Petrova, et al. (2000). "In vivo optical coherence tomography imaging of human skin: norm and pathology." Skin Research and Technology 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." Archives of Dermatology 137(10): 1331-1335.

Glance, B., "Polarization Independent Coherent Optical Receiver," Journal of Lightwave Technology, vol. LT-5, p. 274, Feb. 1987.

Gloesmann, M., B. Hermann, et al. (2003). "Histologic correlation of pig retina radial stratification with ultrahigh-esolution optical coherence tomography." Investigative Ophthalmology & Visual Science 44(4): 1696-1703.

Glombitza, U., "Coherent Frequency-Domain Reflectometry for Characterization of Single-Mode Integrated-Optical Wave-Guides," Journal of Lightwave Technology, vol. 11, pp. 1377-1384, Aug. 1993.

Goldberg, L. and D. Mehuys (1994). "High-Power Superluminescent Diode Source." Electronics Letters 30(20): 1682-1684.

Goldsmith, J. A., Y. Li, et al. (2005). "Anterior chamber width measurement by high speed optical coherence tomography." Ophthalmology 112(2): 238-244.

Goldstein; L. E., J. A. Muffat, et al. (2003). "Cytosolic beta-amyloid deposition and supranuclear cataracts in lenses from people with Alzheimer's disease." Lancet 361(9365): 1258-1265.

Golubovic, B., B. E. Bouma, et al. (1996). "Thin crystal, room-temperature Cr/sup 4 +/:forstefite laser using near-infrared pumping." Optics Letters 21(24): 1993-1995.

Golubovic, B., et al., "Optical Frequency-Domain Reflectometry Using Rapid Wavelength Tuning of a Cr4+: Forsterite Laser," Optics Letters, vol. 11, pp. 1704-1706, Nov. 1997.

Gonick, Maria M., et al.(2002) "Visualization of Blood Microcirculation Parameters in Human Tissues by Time Integrated Dynamic Speckles Analysis" vol. 972, No. 1, Oct. 1, 2002.

Gonzalez, R.C. and Wintz, P., "Digital Image Processing," Addison-Weasley Publishing Company, Reading MA, 1987.

Gonzalez, S. and z. Tannous (2002). "Real-time, in vivo confocal reflectance microscopy of basal cell carcinoma." Journal of the American Academy of Dermatology 47(6): 869-874.

Gordon, M. O. and M.A. Kass (1999). "The Ocular Hypertension Treatment Study: design and baseline description of the participants." Archives of Ophthalmology 117(5): 573-83.

(56) References Cited

OTHER PUBLICATIONS

Gotzinger, Erich et al., "Measurement and Imaging of Birefringent Properties of the Human Cornea with Phase-Resolved, Polarization-Sensitive Optical Coherence Tomography," Journal of Biomedical Optics, vol. 9, No. 1, Jan./Feb. 2004, pp. 94-102.

Grayson, T. P., J. R. Torgerson, et al. (1994). "Observation of a Nonlocal Pancharatnam Phase-Shift in the Process of Induced Coherence without Induced Emission." Physical Review A 49(1): 626-628.

Greaney, M. J., D. C. Hoffman, et al. (2002). "Comparison of optic nerve imaging methods to distinguish normal eyes from those with glaucoma." Investigative Ophthalmology & Visual Science 43(1): 140-5.

Greenfield, D.S., H. Bagga, et al. (2003). "Macular thickness changes in glaucomatous optic neuropathy detected using optical coherence tomography." Archives of Ophthalmology 121(1): 41-46.

Greenfield, D.S., R. W. Knighton, et al. (2000). "Effect of corneal polarization axis on assessment of retinal nerve fiber layer thickness by scanning laser polarimetry." American Journal of Ophthalmology 129(6): 715-722.

Griffin, R. A., D. D. Sampson, et al. (1995). "Coherence Coding for Photonic Code-Division Multiple-Access Networks." Journal of Lightwave Technology 13(9): 1826-1837.

Groner, Warren et al., "Orthogonal Polarization Spectral Imaging: A New Method for Study of the Microcirculation," Nature Medicine Inc., vol. 5, No. 10, pp. 1209-1213, Oct. 1999.

Groot, De P et al., "Three Dimensional Imaging by Sub-Nyquist Sampling of White-Light Interferograms," Optics Letters, vol. 18, No. 17, Sep. 1, 1993.

Guedes, V., J. S. Schuman, et al. (2003). "Optical coherence tomography measurement of macular and nerve fiber layer thickness in normal and glaucomatous human eyes." Ophthalmology 110(1): 177-189.

Gueugniaud, P. Y., H. Carsin, et al. (2000). "Current advances in the initial management of major thermal burns. [Review] (76 refs]." Intensive Care Medicine 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." Journal of Cell Science 105: 317-331.

Guiliano, Scarcelli et al., "Confocal Brillouin Microscopy for Three-Dimensional Mechanical Imaging," Nat Photonis, Dec. 9, 2007.

Guiliano, Scarcelli et al., "Three-Dimensional Brillouin Confocal Microscopy," Optical Society of American, 2007, CtuV5.

Guo, Bujin et al., "Laser-based mid-infrared reflectance imaging of biological tissues", Optics Express, Jan. 12, 2004, vol. 12, No. 1, pp. 208-219.

Guo, Shuguang et al., "Depth-Resolved Birefringence and Differential Optical Axis Orientation Measurements with Finer-based Polarization-Sensitive Optical Coherence Tomography," Optics Letters, vol. 29, No. 17, Sep. 1, 2004, pp. 2025-2027.

Gurov, Igor et al., "High-Speed Signal Evaluation in Optical Coherene Tomography Based on Sub-Nyquist Sampling and Kalman Filtering Method," AIP Coherence Proceedings, vol. 860, Jan. 1, 2006.

Gurov, Igor et al., (2007) "Full-field High-Speed Optical Coherence Tomography System for Evaluating Multilayer and Random Tissues," Proc. of SPIE, vol. 6618.

Gurses-Ozden, R., H. Ishikawa, et al. (1999). "Increasing sampling density improves reproducibility of optical coherence tomography measurements." Journal of Glaucoma 8(4): 238-41.

Gustafsson, M., "Nonlinear structured illumination microscopy: Wide-field fluorescence imaging with theoretically unlimited resolution," PNAS 102:13081 (2005).

Gustafsson, M., "Surpassing the lateral resolution limit by a factor of two using structured illumination microscopy," Journal of Microscopy, 198:82 (2000).

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." Applied Optics Draft Copy.

Haberland, U. R., Walter; Blazek, Vladimir; Schmitt, Hans J. (1995). "Investigation of highly scattering media using hear-infrared continuous wave tunable semiconductor laser." Proc. SPIE , 2389: 503-512.

Haberland, U.H.P., et al., "Chirp Optical Coherence Tomography of Layered Scattering Media," Journal of Biomedical Optics, vol. 3, pp. 259-266, Jul. 1998.

Pierce, Mark C. et al., "Birefringence Measurements in Human Skin Using Polarization-Sensitive Optical Coherence Tomography," Journal of Biomedical Optics, vol. 9, No. 2, Mar./Apr. 2004, pp. 287-291.

Pierce, Mark C. et al., "Collagen Denaturation can be Quantified in Burned Human Skin Using Polarization-Sensitive Optical Coherence Tomography," Elsevier, Burns, 2004, pp. 511-517.

Pierce, Mark C. et al., "Simultaneous Intensity, Birefringence, and Flow Measurements with High-Speed Fiber-Based Optical Coherence Tomography," Optics Letters, vol. 27, No. 17, pp. 1534-1536, Sep. 1, 2002.

Pircher, M., E. Gotzinger, et al. (2003). "Measurement and imaging of water concentration in human cornea with differential absorption optical coherence tomography." Optics Express 11(18): 2190-2197.

Pircher, M., E. Gotzinger, et al. (2003). "Speckle reduction in optical coherence tomography by frequency compounding." Journal of Biomedical Optics 8(3): 56-569.

Pircher, Michael et al., "Imaging Of Polarization Properties of Human Retina in Vivo with Phase Resolved Transversal PS-OCT," Optics Express, vol. 12, No. 24, Nov. 29, 2004pp. 5940-5951.

Pircher, Michael et al., "Three Dimensional Polarization Sensitive OCT of Human Skin In Vivo," 2004, Optical Society of America.

Pircher, Michael et al., "Transversal Phase Resolved Polarization Sensitive Optical Coherence Tomography," Physics in Medicine & Biology, 2004, pp. 1257-1263.

Podbielska, H. "Interferometric Methods and Biomedical Research", SPIE, 1999, 2732:134-141.

Podoleanu, A. G. and D. A. Jackson (1999). "Noise analysis of a combined optical coherence tomograph and a confocal scanning ophthalmoscope." Applied Optics 38(10): 2116-2127.

Podleanu, A. G., G. M. Dobre, et al. (1998). "En-face coherence imaging using galvanometer scanner modulation." Optics Letters 23(3): 147-149.

Podoleanu, A.G., J. A. Rogers, et al. (2000). "Three dimensional OCT images from retina and skin." Optics Express 7(9): 292-298.

Podoleanu, A.G., M. Seeger, et al. (1998). "Transversal and longitudinal images from the retina of the living eye using low coherence reflectometry." Journal of Biomedical Optics 3(1): 12-20.

Podoleanu, Adrian G., "Unbalanced Versus Balanced Operation in an Optical Coherence Tomography System," Applied Optics, vol. 39, pp. 173-182, Jan. 2000.

Polkowski, W. et al., (1998) "Clinical Decision making in Barrett's Oesophagus can be supported by Computerized Immunoquantitation and Morphometry of Features Associated with Proliferation and Differentiation," Journal of Pathology, vol. 184, pp. 161-168.

Poneros et al., "Optical Coherence Tomography of the Biliary Tree During ERCP," Gastrointestinal Endoscopy, Elsevier, NL, vol. 55, No. 1, Jan. 1, 2002, pp. 84-88.

Poneros, John M. "Diagnosis of Barrett's esophagus using optical coherence tomography", Gastrointestinal Endoscopy clinics of North America, 14 (2004) pp. 573-588.

Poneros, John M. et al. (2001) "Diagnosis of Specialized Intestinal Metaplasia by Optical Coherence Tomography" Gastroenterology vol. 120, pp. 7-12.

Poole, C. D. (1988). "Statistical Treatment of Polarization Dispersion in Single-Mode Fiber." Optics Letters 13(8): 687-689.

Povazay, B., K. Bizheva, et al. (2002). "Submicrometer axial resolution optical coherence tomography." Optics Letters 27(20): 1800-1802.

Pratt, Viliyam K., Lazernye Sistemy Svyazi. Moskva, Izdatelstvo, "Svyaz", 1972, pp. 68-70.

Price, J.H.V., et al., Tunable, Femtosecond Pulse Source Operating in the Range 1.06-1.33 mum Based on an Yb3+-doped Holey Fiber

(56)          References Cited

OTHER PUBLICATIONS

Amplifier, Journal of the Optical Society of America B-Optical Physics, vol. 19, pp. 1286-1294, Jun. 2002.

Pyhtila, John W. et al., "Determining nuclear morphology using an improved angle-resolved low coherence interferometry system", Optics Express, Dec. 15, 2003, vol. 11, No. 25, pp. 3473-3484.

Pythila, John W. et al., "Rapid, depth-resolved light scattering measurements using Fourier domain, angle-resolved low coherence interferometry", Optics Society of America, 2004.

Qi, B., A. P. Rimmer, et al. (2004). "Dynamic focus control in high-speed optical coherence tomography based on a microelectromechanical mirror." Optics Communications 232(1-6): 123, 128.

Qi, X. et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. Of Confernce on., vol. 5316, pp. 33-40.

Qiang, Zhou et al., "A Novel Machine Vision Application for Analysis and Visualization of Confocal Microscopic Images," Machine Vision and Applications, vol. 16, No. 2, Feb. 1, 2005.

Rdhakrishnan, S., A. M. Rollins, et al. (2001). "Real-time optical coherence tomography of the anterior segment at 1310 nm." Archives of Ophthalmology 119(8): 1179-1185.

Reid, Brian J. (2001) "p53 and Neoplastic Progression in Barrett's Esophagus" The American Journal of Gastroenterology vol. 96, No. 5, pp. 1321-1323.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," Optics Letters, vol. 27, No. 19, pp. 1702-1704, Oct. 1, 2002.

Richards, G.J. et al. (1997) "Laser Speckle Contrast Analysis (LASCA): A Technique for Measuring Capillary Blood Flow Using the First Order Statistics of Laser Speckle Patterns" Apr. 2, 1997.

Richards-Kortum et al., "Spectral diagnosis of atherosclerosis using an optical fiber laser catheter", American Heart Journal, 1989, 118(2):381-391.

Ripley, Paul M. et al., "A comparison of Artificial Intelligence techniques for spectral classification in the diagnosis of human pathologies based upon optical biopsy", Journal of Optical Society of America, 2000, pp. 217-219.

Roch, Maurice L. et al. "Noninvasive Vascular Elastography: Theoretical Framework", IEEE Transactions on Medical Imaging, vol. 23, No. 2, Feb. 2004, pp. 164-180.

Rogers, A. J. (1981). "Polarization-Optical Time Domain Reflectometry—a Technique for the Measurement of Field Distributions." Applied Optics 20(6): 1060-1074.

Rollins et al., "In Vivo Video Rate Optical Coherence Tomography," Optics Express, vol. 3, pp. 219-229, Sep. 1998.

Rollins, A. M. and J. A. Izatt (1999). "Optimal interferometer designs for optical coherence tomography." Optics Letters 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." Optics Letters 24 (19): 1358-1360.

Rollins, A. M., S. Yazdanfar, et al. (2000). "Imaging of human retinal hemodynamics using color Doppler optical coherence tomography." Investigative Ophthalmology & Visual Science 41(4): S548-S548.

Rollins, A. M., S. Yazdanfar, et al. (2002). "Real-time in vivo colors Doppler optical coherence tomography." Journal of Biomedical Optics 7(1): 123-129.

Rotate, K. and T. Okugawa (1994). "Optical Information-Processing by Synthesis of the Coherence Function." Journal of Lightwave Technology 12(7): 1247-1255.

Roth, Jonathan E. et al., "Simplified Method for Polarization-Sensitive Optical Coherence Tomography," Optics Letters, vol. 26, No. 14, pp. 1069-1071, Jul. 15, 2001.

Rust, M. et al., "Sub-diffraction-limited imaging by stochastic optical reconstruction microscopy (STORM)," Nature Methods 3:783 (2006), and structured illumination microscopy (SIM).

Ruth, B. "blood flow determination by the laser speckle method", Int J Microcirc: Clin Exp, 1990, 9:21-45.

Sadhwarii, Ajay et al., "Determination of Teflon thickness with laser speckle I. Potential for bum depth diagnosis", Optical Society of America, 1996, vol. 35, No. 28, pp. 5727-5735.

Salunke, N.V. et al., "Biomechanics of Atherosclerotic Plaque" Critical Reviews™ in Biomedical Engineering 1997, 25(3):243-285.

Sampliner, Richard E. (2004) "Endoscopic Ablative Therapy for Barrett's Esophagus: Current Status" Gastrointestinal Endoscopy):'. vol. 59, No. 1, pp. 66-69.

Sampliner, Richard E. et al. (1996) "Reversal of Barrett's Esophagus with Acid Suppression and Multipolar Electrocoagulation: Preliminary Results" Gastrointestinal Endoscopy vol. 44, No. 5, pp. 532-535.

Sanchez et al., "Near-Field Fluorscence Microscopy Based on Two-Photon Excvitation with Metal Tips," Phys. Rev. Lett. 82 (20) 1999, pp. 4014-4017.

Sandoz, P. (1997). "Wavelet transform as a processing tool in white-light interferometry." Optics Letters 22(14): 1065-1067.

Zhao, Y., Z. Chen, et al. (2002). "Real-time phase-resolved functional optical coherence tomography by use of optical Hilbert transformation." Optics Letters 27(2): 98-100.

Zhao, Yong et al., "Virtual Data Grid Middleware Services for Data-Intensive Science," Concurrency and Computation: Practice and Experience, Wiley, London, GB, Jan. 1, 2000, pp. 1-7, pp. 1532-0626.

Zhao, D., P.R. Prucnal, et al. (1998). "A widely tunable narrow linewidth semiconductor fiber ring laser." IEEE Photonics Technology Letters 10(6): 781-783.

Zhou, Xiao-Qun et al., "Extended-Range FMCW Reflectometry Using an optical Loop with a Frequency Shifter," IEEE Photonics Technology Letters, vol. 8, pp. 248-250, Feb. 1996.

Zimnyakov et al., "A study of statistical properties of partially developed speckle fields as applied to the diagnosis of structural changes in human skin", Optics and Spectroscopy. 1994, 76(5): 747-753.

Zimnyakov, Dmitry A. et al.(2002) "Speckle-Contrast Monitoring of Tissue Thermal Modification" Applied Optics vol. 41, No. 28, pp. 5989-5996.

Zimnyakov et al., "Spatial speckle correlometry in applications to tissue structure monitoring", Applied Optics 1997, 36(22): 5594-5607.

Zimnyakov et al., "Speckle patterns polarization analysis as an approach to turbid tissue structure monitoring", SPIE 1999, 2981:172-180.

Zorabedian, Paul et al., "Tuning Fidelity of Acoustooptically Controlled External Cavity Semiconductor-Lasers," Journal of Lightwave Technology, vol. 13, pp. 62-66, Jan. 1995.

Zuluaga, A. F. and R. Richards-Kortum (1999). "Spatially resolved spectral interferometry for determination of subsurface structure." Optics Letters 24(8): 519-521.

Zumbusch, Andreas et al. "Three-dimensional vibrational imaging by coherent anti-Stokes Raman scattering", Physical Review Letters 1999, 82 (20): 4142-4145.

Zvyagin, A. V., J. B. FitzGerald, et al. (2000). "Real-time detection technique for Doppler optical coherence tomography." Optics Letters 25(22): 1645-1647.

Liu, J., X. Chen, et al. (1999). "New thermal wave aspects on burn evaluation of skin subjected to instantaneous heating." IEEE Transactions on Biomedical Engineering 46(4): 420-8.

Loree et al., "Mechanical Properties of Model Atherosclerotic Lesion Lipid Pools", Arteriosclerosis and Thrombosis, 1994, 14(2):230-234.

Lu, Shih-Yau et al., "Homogeneous and Inhomogeneous Jones Matrices," J. Opt. Soc. Am. A., vol. 11, No. 2, pp. 766-773, Feb. 1994.

Luke, D. G., R. McBride, et al. (1995). "Polarization mode dispersion minimization in fiber-wound piezoelectric cylinders." Optics Letters 20(24): 2550-2552.

(56) References Cited

OTHER PUBLICATIONS

MacNeil, B. D., I. K. Jang, et al. (2004). "Focal and multi-focal plaque distributions in patients with macrophage acute and stable presentations of coronary artery disease." Journal of the American College of Cardiology 44(5): 972-979.

Mahgerefteh, D. and C.R. Menyuk (1999). "Effect of first-order PMD compensation on the statistics of pulse proadening in a fiber with randomly varying birefringence." Ieee Photonics Technology Letters 11(3): 340-342.

Maitland, D. J. and J. T. Walsh, Jr. (1997). "Quantitative measurements of linear birefringence. during heating of native collagen." Lasers in Surgery & Medicine 20 (3): 310-8.

Majaron, B., S. M. Srinivas, et al. (2000). "Deep coagulation of dermal collagen with repetitive Er: YAG laser irradiation." Lasers in Surgery and Medicine 26(2): 215-222.

Manoharan, Ramasamy et al., "Biochemical analysis and mapping of atherosclerotic human artery using FT-IR microspectroscopy", Atherosclerosis, May 1993, 181-1930.

Mansuripur, M. (1991). "Effects of High-Numerical-Aperture Focusing on the State of Polarization in Optical and Magnetooptic Data-Storage Systems." Applied Optics 30(22): 3154-3162.

Marshall, G. W., S. J. Marshall, et al. (1997). "The dentin substrate: structure and properties related to bonding." Journal of Dentistry 25(6): 441-458.

Martin, P. (1997). "Wound healing—Aiming for perfect skin regeneration." Science 276 (5309): 75-81.

Martinez, O. E. (1987). "3000 Times Grating Compressor with Positive Group-Velocity Dispersion-Application to Fiber Compensation in 1.3-1.6 Mu-M Region." Ieee Journal of Quantum Electronics 23(1): 59-64.

Martinez, O. E., J.P. Gordon, et al. (1984). "Negative Group-Velocity Dispersion Using Refraction." Journal of the Optical Society of America a-Optics Image Science and Vision 1(10):1003-1006.

Martinez, Oscar Eduardo, "3000 Times Grating Compress or with Postive Group Velocity Dispersion," IEEE, vol. QE-23, pp. 59-64, Jan. 1987.

Masahiro, Yamanari et al., "Polarization-Sensitive Swept-Source Optical Coherence Tomography with Continuous Source Polarization Modulation," Optics Express, vol. 16, No. 8, Apr. 14, 2008.

Matcher, Stephen J. et al., "The Collagen Structure of Bovine Intervertebral Disc Studied Using Polarization-Sensitive Optical Coherence Tomography," Physics in Medicine and Biology, 2004, pp. 1295-1306.

McKenzie, A. L. (1990) "Physics of Thermal Processes in Laser-Tissue Interaction" Phys. Med. Biol vol. 35, No. 9, pp. 1175-1209.

McKinney, J. D., M.A. Webster, et al. (2000). "Characterization and imaging in optically scattering media by use of laser speckle and a variable-coherence source." Optics Letters 25(1): 4-6.

Miglior, S., M. Casula, et al. (2001). "Clinical ability of Heidelberg retinal tomograph examination to detect glaucomatous visual field changes." Ophthalmology 108 (9): 1621-7.

Milner, T. E., D. J. Smithies, et al. (1996). "Depth determination of chromophores in human skin by pulsed photothermal radiometry." Applied Optics 35(19): 3379-3385.

Milner, T. E., D. M. Goodman, et al. (1995). "Depth Profiling of Laser-Heated Chromophores in Biological Tissues by Pulsed Photothermal Radiometry." Journal of the Optical Society of America a-Optics Image Science and Vision 12(7): 1479-1488.

Milner, T. E., D. M. Goodman, et al. (1996). "Imaging laser heated subsurface chromophores in biological materials: Determination of lateral physical dimensions." Physics in Medicine and Biology 41(1): 31-44.

Mishchenko, M. I. and J. W. Hovenier (1995). "Depolarization of Light Backscattered by Randomly Oriented Nonspherical Particles." Optics Letters 20(12): 1356-&.

Mistlberger, A., J.M. Liebmann, et al. (1999). "Heidelberg retina tomography and optical coherence tomography in normal, ocular-hypertensive, and glaucomatous eyes." Ophthalmology 106(10): 2027-32.

Mitsui, T. (1999). "High-speed detection of ballistic photons propagating through suspensions using spectral Interferometry." Japanese Journal of Applied Physics Part I—Regular Papers Short Notes & Review Papers 38(5A): 2978-2982.

Mitsui, Takahisa, "Dynamic Range of Optical Reflectometry with Spectral Interferometry," Japanese Journal of Applied Physics Part 1—Regular Papers Short Notes & Review Papers, vol. 38, pp. 6133-6137, 1999.

Moiseev et al., "Spectral Self-Interfence Fluorescence Microscopy," J. Appl. Phys. 96 (9) 2004, pp. 5311-5315.

Molteno, A. C., N. J. Bosma, et al. (1999). "Otago glaucoma surgery outcome study: long-term results of trabeculectomy—1976 to 1995." Ophthalmology 106(9): 1742-50.

Montag, Ethan D., "Parts of the Eye," online textbook for JIMG 774: Vision & Psycophysics, download on Jun. 23, 2010 from http://www.cis.rit.edu/people/faculty/montag/vandplite/pages/chap_8/ch8p3.html.

Montgomery, E. et al., "Reproducibility of the Diagnosis of Dysplasia in Barrett Esophagus: A Reaffirmation," Apr. 2001, Human Pathology, vol. 32, No. 4, pp. 368-378.

Moreau, Julien et al., "Full-Field Birefringence Imaging by Thermal-Light Polarization-Sentive Optical Coherence Tomography. II. Instrument and Results," Applied Optics, vol. 42, No. 19, pp. 3811-3818, Jul. 1, 2003.

Moreau, Julien et al., "Full-Field Birefringence Imaging by Thermal-Light Polarization-Sensitive Optical Coherence Tomography I. Theory," Applied Optics, vol. 42, No. 19, pp. 3800-3810, Jul. 1, 2003.

Morelli, J.G., et al.(1986) "Tunable Dye Laser (577 nm) Treatment of Port Wine Stains" Lasers in Surgery and Medicine vol. 6, pp. 94-99.

Morgan, Stephen P. et al., "Surface-Reflection Elimination in Polarization Imaging of Superficial Tissue," Optics Letters, vol. 28, No. 2, pp. 114-116, Jan. 15, 2003.

Morgner, U., F. X. Kartner, et al. (1999). "Sub-two-cycle pulses from a Kerr-lens mode-locked Ti: sapphire laser (vol. 24, p. 411, 1999)." Optics Letters 24(13): 920-920.

Morgner, U., W. Drexler, et al. (2000). "Spectroscopic optical coherence tomography." Optics Letters 25(2): 111-113.

Motaghian Nezam, S.M. et al., "High-speed Wavelength-Swept Semiconductor laser using a Diffretion Grating and a Polygon Scanner in Littro Configuration" Optical Fiber Communication and the National Fiber Optic Engineers Conference Mar. 29, 2007.

Motaghian Nezam, S.M.R. (2007) "increased Ranging Depth in optical Frequency Domain Imaging by Frequency Encoding" Optics Letters, vol. 32, No. 19, Oct. 1, 2007.

Motz, J.T. et al., "Spectral-and Frequency-Encoded Fluorescence Imaging" Optics Letters, OSA, Optical Society of America, Washington, DC, US, vol. 30, No. 20, Oct. 15, 2005, pp. 2760-2762.

Mourant, J. R., A.H. Hielscher, et al. (1998). "Evidence of intrinsic differences in the light scattering properties of tumorigenic and nontumorigenic cells." Cancer Cytopathology 84(6): 366-374.

Muddassir, M. Gualini et al., "Recent Advancements of Optical Interferometry Applied to Medicine", IEEE Transactions on Medical Imaging, vol. 23, No. 2, Feb. 2004, pp. 205-212.

Muller, M., J. Squier, et al. (1998). "Dispersion pre-compensation of 15 femtosecond optical pulses for high-numerical-aperture objectives." Journal of Microscopy-Oxford 191: 141-150.

Murakami, K., "A Miniature Confocal Optical Scanning Microscopy for Endscopes," Proceedings of SPIE, vol. 5721, pp. 119-131, Feb. 28, 2005.

Muscat, S., N. McKay, et al. (2002). "Repeatability and reproducibility of corneal thickness measurements by optical coherence tomography." Investigative Ophthalmology & Visual Science 43(6): 1791-5.

Musch, D. C., P.R. Lichter, et al. (1999). "The Collaborative Initial Glaucoma Treatment Study. Study Design, MethodsR, and Baseline Characteristics of Enrolled Patients." Ophthalmology 106:653-662.

Nadkarni, Seemantini K. et al.(2005) "Charaterization of Atherosclerotic Plaques by Laser Speckle Imaging" Circulation vol. 112, pp. 885-892.

Nadkarni, Seemantini K., et al., "Measurement of fibrous cap thickness in atherosclerotic plaques by spatiotemporal analysis of

(56) References Cited

OTHER PUBLICATIONS laser speckle images", Journal of Biomedical Optics, vol. 11 Mar./Apr. 2006, pp. 021006-1-021006-8.

Naganuma, Kazunori et al., "Group-Delay Measurement Using the Fourier-Transorm of an Interferometric Cross-Correlation Generated by White Light," Optics Letters, vol. 15, pp. 393-395, Apr. 1990.

Nahen, Kester et al. (1999) "Investigations on Acoustic On-Line Monitoring of IR Laser Ablation of burned Skin" asers in Surgery and Medicine vol. 25, pp. 69-78.

European Official Communication dated Aug. 11, 2012 for EP 10193526.0.

European Official Communication dated Feb. 6, 2013 for 04822169.1.

European Patent Office Search Report dated Nov. 20, 2007 for European Application No. 05791226.3.

European Search Report dated Jun. 25, 2012 for EP 10733985.5.

European Search Report for 12194876.4 dated Feb. 1, 2013.

European Search Report issued May 5, 2009 for European Applications No. 01991471.2.

European Search Report mailed on Mar. 11, 2013 for EP 10739129.4.

Extended European Search Report dated Mar. 8, 2017 for European Patent Application No. 14826957.4.

Extended European Search Report mailed Dec. 14, 2010 for EP 10182301.1.

International Preliminary Report on Patenatability dated Jun. 7, 2007 for PCT/US2005/042408.

International Search and Written Opinion dated Jun. 10, 2009 for PCT/US2008/075456.

International Search Report and Written Opinion dated Dec. 20, 2004 for PCT/US04/10152.

International Search Report and Written Opinion dated Feb. 2, 2009 for International Application No. PCT/US2008/071786.

International Search Report and Written Opinion dated Feb. 24, 2009 for PCT/US2008/076447.

International Search Report and Written Opinion dated Feb. 28, 2007 for International Applicatin No. PCT/US2006/038277.

International Search Report and Written Opinion dated Jan. 15, 2009 for International Application No. PCT/US2008/074863.

International Search Report and Written Opinion dated Jan. 30, 2009 for International Application No. PCT/US2008/081834.

International Search Report and Written Opinion dated Mar. 23, 2006 for PCT/US2005/042408.

International Search Report and Written Opinion dated May 26, 2008 for International Application No. PCT/US2008/051404.

International Search Report and Written Opinion for PCT/US2013/022136.

International Search Report and Written Opinion mailed Aug. 30, 2012 for PCT/US2012/035234.

International Search Report and Written Opinion mailed Feb. 9, 2012 based on PCT/US2011/034810.

International Search Report and Written Opinion mailed Jan. 31, 2013 for PCT/US2012/060843.

International Search Report and Written Opinion mailed Jul. 18, 2008 for PCT/US2008/057533.

International Search Report and Written Opinion mailed Jul. 4, 2008 for PCT/US2008/051432.

International Search Report and Written Opinion mailed Jun. 10, 2008 for PCT/US2008/051335.

International Search Report and Written Opinion mailed Mar. 14, 2005 for PCT/US2004/018045.

International Search Report and Written Opinion mailed Mar. 7, 2006 for PCT/US2005/035711.

International Search Report and Written Opinion mailed Oct. 25, 2012 for PCT/US2012/047415.

International Search Report dated Apr. 29, 2011 for PCT/US2010/051715.

International Search Report dated Feb. 23, 2010 for U.S. Appl. No. 11/445,131.

International Search Report dated Jan. 27, 2010 for PCT/US2009/047988.

International Search Report dated Jan. 27, 2010 for PCT/US2009/050553.

International Search Report dated Jul. 28, 2011 for PCT/US2010/059534.

International Search Report dated May 27, 2010 for PCT/US2009/063420.

International Search Report dated Nov. 18, 2011 for PCT/US2011/027437.

International Search Report dated Nov. 18, 2011 for PCT/US2011/027450.

International Search Report dated Sep. 13, 2010 for PCT/US2010/023215.

International Search Report for International Application No. PCT/US2014/047034 mailed on Nov. 26, 2014.

International Search Report mailed Jan. 31, 2013 for PCT/US2012/061135.

International Search Reported dated Nov. 22, 2011 for PCT/US2011/027421.

Invitation of Pay Additional Fees mailed Aug. 7, 2008 for International Application No. PCT/US2008/062354.

Invitation of Pay Additional Fees mailed Jul. 20, 2008 for International Application No. PCT/US2007/081982.

Japanese Language Appeal Decision dated Jan. 10, 2012 for JP 2006-503161.

Japanese Notice of Grounds for Rejection dated Dec. 28, 2011 for JP2008-535793.

Japanese Notice of Grounds for Rejection dated Oct. 28, 2011 for JP2009-294737.

Japanese Notice of Reasons for Rejection dated Dec. 12, 2011 for JP2008-533712.

Japanese Notice of Reasons for Rejection dated Jul. 14, 2009 for Japanese Patent Application No. 2006-503161.

Japanese Notice of Reasons for Rejection dated Jun. 20, 2012 for JP 2009-546534.

Japanese Notice of Reasons for Rejection dated Mar. 27, 2012 for JP2003-102672.

European Patent Office, Extended Search Report, Application No. 24156541.5, May 17, 2024, 9 pages.

* cited by examiner

IMAGING APPARATUS AND METHOD WHICH UTILIZES MULTIDIRECTIONAL FIELD OF VIEW ENDOSCOPY

CROSS-REFERENCE TO RELATED APPLICATION(S)

The present application is a continuation of U.S. patent application Ser. No. 14/906,090, filed Jan. 19, 2016, which is the U.S. national stage entry of International Application PCT/US2014/047034, filed Jul. 17, 2014, which claims benefit of U.S. patent application Ser. No. 61/856,152, filed Jul. 19, 2013, and U.S. patent application Ser. No. 61/985,824, filed Apr. 29, 2014, the contents of each are incorporated berein in their entireties.

STATEMENT REGARDING FEDERALY SPONSORED RESEARCH

This invention was made with government support under FA9550-11-1-0331 awarded by the Air Force Office of Scientific Research. The government has certain rights in the invention.

FIELD OF THE DISCLOSURE

The present disclosure relates to exemplary embodiments of medical endoscopic imaging apparatus and method used to improve, e.g., the field of view, speed and efficiency of diagnostic endoscopic procedure, therapeutic endoscopic procedure, and other industrial inspection endoscopic procedures. The exemplary apparatus and method can be utilized and/or performed in conjunction with any endoscope.

BACKGROUND INFORMATION

Endoscopic arrangements generally use a rigid or flexible endoscope with accessory channel(s) to aid diagnosis, carry out treatment or inspection. The endoscope can be inserted into animal or human body in medical applications, including gastrointestinal tract, respiratory tract, and other internal organs, or other environments with special interests or under extreme conditions. The field of view of current endoscopic arrangement is generally limited by its configuration or light delivery and lens system, which only allows forward or another single directional field of view. The limitation of current endoscopic and laparoscopic devices to provide only one field of view typically decreases the diagnostic accuracy, and can cause various lesions to be missed.

One method for visualizing the backwards field of view can include inserting a separate backwards viewing endoscope through the accessory port of another endoscope. While this method provides backwards viewing, it can prevent the use of the accessory port while the backwards viewing endoscope is inserted therein. The backwards viewing endoscope should be withdrawn prior to biopsy acquisition, suction, and flushing, which can increase the time and cost of the procedure. A separate endoscope typically is furthermore sterilized following use, which can again increase the complexity of the procedure. The use of multiple endoscopes may also require multiple connections to an imaging console, which can further complicate the procedure. The additional complexity and cost of utilizing a separate endoscope can make it inconvenient to see in multiple directions, which may result in a decreased adoption of multiple endoscopes for obtaining images of additional fields of view.

The application of conventional forward viewing Endoscopy is limited primarily by the viewing angle of the instruments. Although large field of view endoscope is available, in many circumstances, there are considerable missed detections of important areas of interest, which could cause potential calamity without prompt treatment.

There may therefore be a need for addressing at least some of the issues and/or deficiencies identified above. To that end, it may be beneficial to provide an endoscopic or laparoscopic imaging system configuration that can facilitate multiple fields of view, including side and backwards fields. In addition, there may be a need to provide an imaging system for multidirectional fields of view endoscopy, in which the movement of the imaging system can be fully controlled and the diagnostic and therapeutic endoscopy can be performed in single procedure, if necessary.

SUMMARY OF EXEMPLARY EMBODIMENTS

Thus, apparatus and method according to an exemplary embodiment of the present disclosure can be provided that facilitates additional fields of view in a more beneficial device that does not remove the functionality of the endoscope's accessory port during the imaging procedure.

In various exemplary embodiments according to the present disclosure, exemplary configurations for the acquisition of multidirectional viewing during endoscopic examination can be provided. Exemplary applications can be utilized, in which increasing the field of view while using endoscopic systems can be improved with the exemplary embodiments of the apparatus and method of continuous and simultaneous forward and multidirectional views during a colonoscopic, baroscopic, laparoscopic, angioscopic, or other endoscopic procedures.

Multiple wavelengths illumination, fluorescence detection, 3D surface measurement, signal detector configuration, power management, image device clean mechanism, multiple sensors for measurement of temperature, blood pressure, positions, pH value, and heart rate, etc., can be configured into this image device to be used as a multifunctional and multidirectional fields of view device in cooperated with conventional endoscopy to provide controllable and effective diagnostic and therapeutic procedures.

In an exemplary embodiment of the present disclosure, an exemplary device/apparatus providing the multidirectional fields of view can be attached to the endoscope, which does not generally affect the normal function of the Endoscope, such as the accessory port and angulations. The exemplary apparatus can provide continuous and simultaneous forward and multidirectional views during a colonoscopic, baroscopic, laparoscopic, angioscopic, or other endoscopic procedures. Exemplary embodiments of the present disclosure can be applied to rigid, flexible, wireless or telescoping endoscope to provide, e.g., continuous multidirectional views of animate and inanimate hollow spaces. The dimensions of the exemplary apparatus may be scaled to fit specific scope sizes.

Exemplary embodiments of the present disclosure can relate generally to exemplary configuration of optical and electronic elements, and to the application(s) thereof in exemplary endoscopic imaging systems which can be used with medical and industrial applications to improve the field of view, speed and efficiency of an endoscopic procedure.

According to another exemplary embodiment of the present disclosure, the exemplary device/apparatus can include a video/analog/digital image sensor/camera and/or signal detectors and sensors that can be embedded in a cap that can be attached to the part of the endoscope. In a further exemplary embodiment of the present disclosure, multiple configurations of signals and/or images sensors/detectors can be contained within the cap.

In a further exemplary embodiment of the present disclosure, compressive imaging can be implemented to acquire the images. According to still another exemplary embodiment of the present disclosure, images can be detected by photodetectors, such as photodiodes, photocathodes, photomultiplier tubes, photoconductive cells, photovoltaic cells, photoresistors, phototransistors, cryogenic detectors, or single pixel CCD or single pixel CMOS sensors. According to another exemplary embodiment of the present disclosure, multiple pixels CCD and CMOS sensors can be used. For example, random and/or pseudorandom binary patterns and/or masks can be used to reconstruct the images of the subjects under examination. The patterns and/or masks can be generated by spatial light modulators, digital micromirror array, spinning disk of random patterns and/or masks. The masks can be implemented by using a set of light attenuating layers to modulate the light. The masks can also be implemented by using array of aperture elements, like liquid crystal display (LCD), of which each element can be controlled independently. For example, scanning mirrors, spatial light modulators, digital micromirror array, and/or array of aperture elements can be used to control the direction of the light illumination, so that images of the subjects under examination can be reconstructed.

According to yet another exemplary embodiment of the present disclosure, multiple configurations of light illumination can be included in the cap so as to illuminate the additional fields of view and provide multi wavelengths illumination and tissue fluorescence images. Multi wavelengths can be different colors, including red, green, blue, and/or white color, to provide multi bands imaging and different contrast for the tissue imaging, such as narrow band imaging used frequently in endoscopy. Fluorescence images include tissue autofluorescence images and exogenous fluorescence images by using exogenous fluorescent contrast agents.

In still a further exemplary embodiment of the present disclosure, switchable different wavelengths and/or color filters can be put in front of the light illumination sources to provide different illuminations. For example, switchable different wavelengths and/or color filters can be put in front of the image sensors, and/or signal detectors to filter different signals associated with different wavelengths.

According to yet another exemplary embodiment of the present disclosure, the imaging cap can be rotated, so that any particular area of interest can be accessed by the imaging device. A mechanical motor can be controlled by the imaging device and rotate the imaging cap around the endoscope.

In yet a further exemplary embodiment of the present disclosure, a three-dimensional structure can be measured by the imaging device by using passive stereo vision, by using multiple camera and/or image sensors, and/or detectors. For example, a three-dimensional structure can be measured by the imaging device by using active stereo vision, by using structured illumination, laser structured light, and/or scanned light beams.

According to yet another exemplary embodiment of the present disclosure, the signals and/or images can be transmitted remotely via a wireless transmitter. In addition or as an alternative, a battery source can be contained within the cap that can power the signals and/or images sensors/detectors and illumination sources without requiring an external connection.

In yet another exemplary embodiment of the present disclosure, the wireless transmission method includes radio frequency (RF) wireless technology and optical transmission of the signals using light wavelengths that penetrate the body effectively. For example, the light source can be light emitting diode (LED), laser diode (LD), and/or superluminescent diode (SLD). The wavelength can be in the visible range, near infra red, and/or infra red. The light source emits light modulated by the signals or the images. Two-way communication can be implemented. A signal receiver within the device can be used to receive commands from outside of the subject and send the commands to central processing unit in the device to function accordingly.

According to yet another exemplary embodiment of the present disclosure, the signals and/or images can be transmitted via one or more electrical wires that can be attached to the cap, and extend outside alongside the primary endoscope or probe device to an external signal/image processor. In yet another exemplary embodiment, power can be provided by electrical wires that can be attached to the cap, and extend outside alongside the primary endoscope or probe device with an external power supply.

In an additional exemplary embodiment of the present disclosure, the power can be provided by wirelessly and externally. Inductive coupling can be used to provide the power of the imaging device. According to yet another exemplary embodiment of the present disclosure, an ultrasonic transducer can be used to convert ultrasonic energy into an electrical energy and provide power of the imaging device.

Further, an exemplary apparatus can include an endoscopic first arrangement, a radiation source second arrangement which can provide at least one electro-magnetic radiation, a detector third arrangement, a signals/images transmission fourth arrangement, a power supply fifth arrangement and multifunctional sensors sixth arrangement. For example, the second to sixth arrangements can be attached to at least one portion of the endoscopic arrangement.

An exemplary detector arrangement can be provided, whereas the endoscopic arrangement can be associated with the radiation source arrangement, the signals/images transmission arrangement, the power supply arrangement, multifunctional sensors and/or the detector arrangement. The radiation can be directed in a backward direction or a side direction with illuminating 360 degrees of azimuth angle or any other degrees of angles with respect to the forward direction of the endoscopic first arrangement. Further, an electronic arrangement can be provided which can be configured to regulate and/or synchronize the radiation source arrangement, the detector arrangement, the signals/images transmission arrangement, the power supply arrangement, and the multifunctional sensors arrangement. As an alternative or in addition, the electronic arrangement can be configured to (i) synchronize the signals/images transmission arrangement and the detector arrangement, (ii) control the detector arrangement to detect signals from the anatomical or physical structure(s) illuminated by the radiation source, (iii) separate the signals from each detector based the synchronization with the signals/images transmission arrangement, (iv) manage the power for the electronic elements, (v) control the multifunctional sensors, and (vi)

control the mechanical motors to position the imaging cap, light illumination, the supportive balloon and projections, etc.

According to yet another exemplary embodiment of the present disclosure, the imaging cap can be put on endoscopes by universal fit. Memory foam and/or silicone gel can be used as the inner tube materials. The materials will provide sufficient friction to grab the endoscopes and prevent the cap to fall off. For example, clamps can be used to grip tightly the imaging cap, and/or flexible connection segment between the battery housing and cap, with the endoscope. The cap can fit to the endoscope by use of a compression coupling arrangement in which the cap rotates in one direction on itself to increase the internal diameter for accepting the endoscope and rotates in the opposite direction on itself to reduce the internal diameter and temporarily fasten to the endoscope.

In yet a further another exemplary embodiment of the present disclosure, the transparent window of the imaging cap can be cleaned by water or air nozzle, which is connected by small hoses and/or ducts with the water or air nozzles of the endoscope. The imaging cap can be rotated, so that a window shield can be used to scrub the imaging window to keep it clean. Further or alternatively, the imaging window can be coated with materials (e.g. hydrophobic coatings) to prevent mucus and other environmental fluids to stain the imaging window so to keep it clean.

According to yet another exemplary embodiment of the present disclosure, the imaging cap may be constructed such that the outer covering material of the cap is designed to be disposable, while the internal optics and electronics are designed to be reusable. The cap covering material would be designed such that it may be sterilized. Once sterile, it would be opened by a person in the sterile field, while the non-sterile internal optics and electronics would be placed inside. Once the electronics and optics are inserted, the cap would be closed by the person in the sterile field and the procedure would continue.

In one exemplary embodiment of the present disclosure, an exemplary apparatus for coupling to a probe and providing information regarding at least one structure can be provided. For example, the apparatus can include an electronics arrangement which is configured to obtain the information and transmit the information wirelessly, and a structural connection configuration which is structured and configured to be attached to the probe.

For example, the probe can include an endoscope. The structural connection configuration can be structured to be connected to the probe at or near a distal end thereof. The information can be regarding at least one portion of the structure(s) that is different from further information regarding the structure(s) obtained separately by the probe. The electronics arrangement can be configured to obtain the information from a first direction, and the probe can be configured to obtain the further information from a second direction, which is approximately either opposite or perpendicular to the first direction.

According to an exemplary variant, the electronics arrangement can include a first illumination arrangement which can be structured and positioned to illuminate the structure(s) in a first direction, and the probe can include a second illumination arrangement which can be structured and positioned to illuminate the structure(s) in a second direction, which is approximately either opposite or perpendicular to the first direction. Further or in addition, the electronics arrangement can include a portable power arrangement which can be configured to provide power to at least one component of the electronics arrangement.

An inductive arrangement can also be provided which can be configured to recharge the power arrangement. A portable power arrangement can also be provided which can be coupled, in a wired configuration, to a housing of the electronics arrangement, and configured to provide power to at least one component of the electronics arrangement. In addition, a housing can be provided that at least partially encloses the electronics arrangement, where a total length of the housing that extends along an extension of the probe can be at most 35 mm and at least 25 mm. A total thickness of a wall of the housing that extends radially from the probe can be at most 2 mm and at least 1 mm.

In yet another exemplary embodiment of the present disclosure, the electronics arrangement can include a radiation-providing arrangement which can be configured to forward multiple radiations at different respective wavelengths to at least one portion of the sample (s). The electronics arrangement can further include a detector arrangement which is configured to detect image information regarding the portion(s) based on the wavelengths. The detector arrangement can include a single pixel detector and/or a multi-pixel detector. The detector arrangement can also include multiple detectors detecting return radiations from different respective portions of the sample(s). A computer arrangement can also be provided which is configured to generate further information based on the image information as a function of the wavelengths. The multiple radiations being provided by the radiation-providing arrangement can include predetermined patterns of light radiations A detector arrangement can also be provided which is configured to detect at least one return radiation from at least one portion of at least one sample based on the predetermined patterns, and provide the data for the portion(s) based on the return radiation(s). In addition, a computer arrangement can be provided which is configured to generate the information with includes image data for the portion(s) as a function of the data and prior knowledge of the predetermined patterns.

According to still another exemplary embodiment of the present disclosure, an apparatus for coupling to a probe and providing image information regarding at least one structure can be provided. For example, the apparatus can include a light-providing arrangement which is configured to forward predetermined patterns of light radiation to the structure(s), and a detector arrangement which can be configured to detect at least one return radiation from at least one portion of the structure based on the predetermined patterns, and provide the data for the portion(s) based on the return radiation(s). Further, a computer arrangement can be provided which is configured to generate the image information for the portion(s) as a function of the data and prior knowledge of the predetermined patterns. A structural connection configuration can further be provided which is structured and configured to be attached to the probe, and connected to the detector arrangement.

For example, the detector arrangement can include a single pixel detector, a multi-pixel detector, and/or multiple detectors detecting return radiations from different respective portions of the sample(s). The light-providing arrangement can include a source arrangement. The probe can include an endoscope. The detector and the computer arrangement can be part of an electronics arrangement which can be configured to transmit the image information wirelessly. A first fluid transmitting arrangement can be coupled to a second fluid transmitting arrangement of the probe.

In still a further exemplary embodiment of the present disclosure, an apparatus for coupling to a probe and providing information regarding at least one structure can be provided. The exemplary apparatus can include an electronics arrangement which is configured to obtain the information, a structural connection configuration which is structured and configured to be attached to the probe, and a first fluid transmitting arrangement coupled to a second fluid transmitting arrangement of the probe. For example, the first fluid transmitting arrangement can be configured to transmit a fluid thereof to an external portion of the apparatus. The fluid can be a gas and/or a liquid. The apparatus can also include a light-providing arrangement which is configured to forward predetermined patterns of light radiation to the structure(s), and a detector arrangement which is configured to detect at least one return radiation from at least one portion of the structure(s) based on the predetermined patterns, and provide the data for the portion(s) based on the return radiation(s). A computer arrangement can also be provided which is configured to generate the information for the portion(s) as a function of the data and prior knowledge of the predetermined patterns. The electronics arrangement can be configured to transmit the information wirelessly.

These and other objects, features and advantages of the exemplary embodiments of the present disclosure can become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure can become apparent from the following detailed description taken in conjunction with the accompanying Figures showing illustrative embodiments of the present disclosure, in which.

Figure 1A:
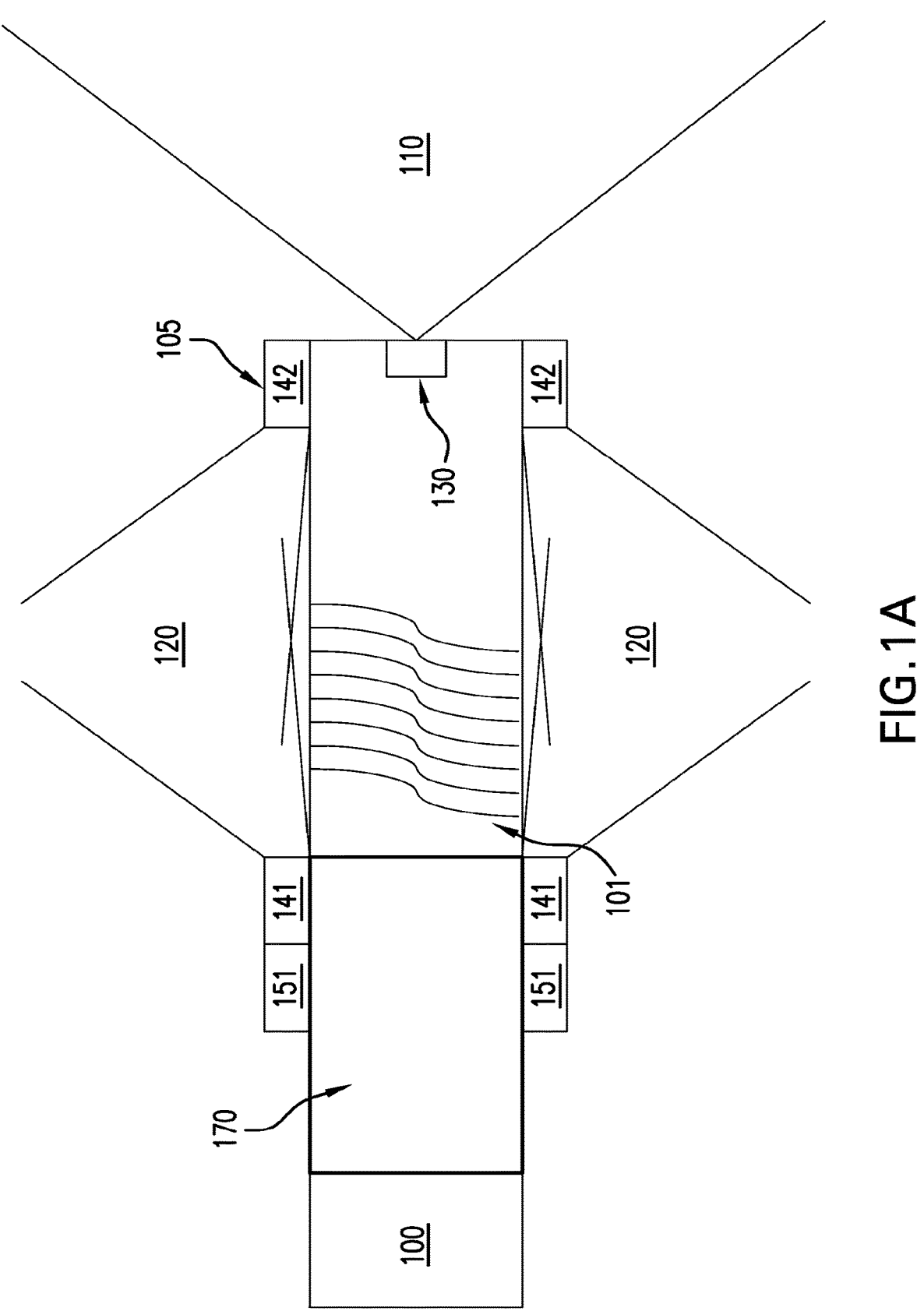
FIGS. 1A-D are exemplary block diagrams of an imaging apparatus, and optical, and electronic elements thereof, according to certain exemplary embodiments of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures, or the appended claims.

DETAILED DESCRIPTION OF EXEMPLARY EMBODIMENTS

Using the exemplary embodiments of the apparatus, system and method of the present disclosure, it is possible to facilitate a visualization of a plurality of fields of view, and monitor plurality of indicators of diagnostic and therapeutic procedures, e.g., at a plurality of angles with respect to the long axis of the endoscope by multiplexing image fields of view, and multiple functional sensors by using an optical and electronic apparatus. In one exemplary embodiment of the present disclosure, an optical and electronic apparatus can be provided in which multiple miniature image sensors, signal detectors, lenses, and light emitting diodes (LEDs) are mounted at certain positions such that certain radiations are directed to and/or received from different field angles and therefore illuminate and/or receive different fields of view. Further, multiple sensors can be attached at certain positions to monitor temperature, blood pressure, positions, pH value, and heart rate, etc. In one exemplary embodiment of the present disclosure, a battery (e.g., 170) and wireless transmitters (e.g., 151) can be attached to provide power and transmit the captured images and acquired signals to a wireless receiver outside the subject under examination.

Figure 1B:
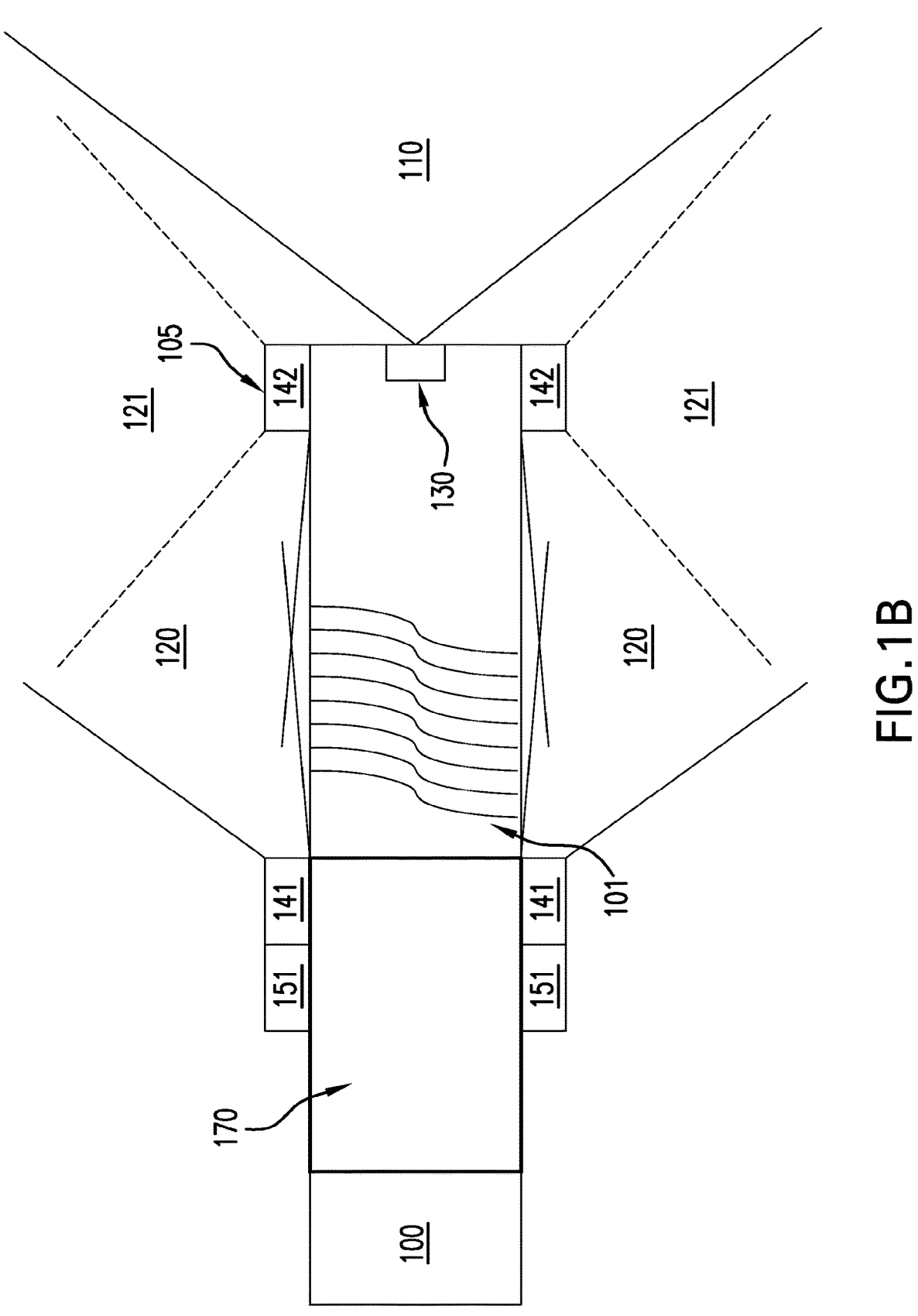
Figure 1C:
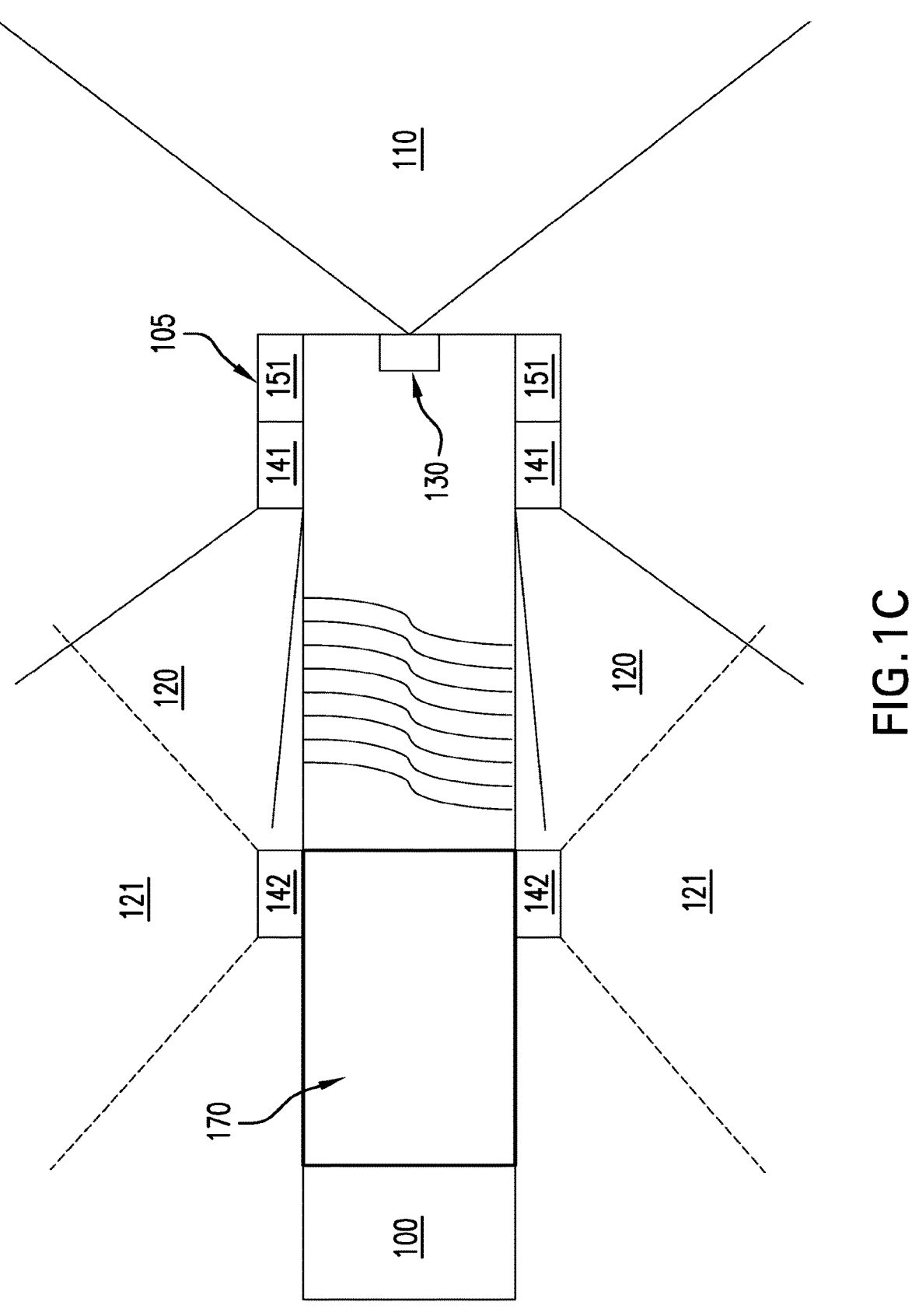

According to an exemplary embodiment of the present disclosure, as shown in FIGS. 1A-1C, the illumination sources 142 can be separated with the imaging optics, image sensors and/or signal detectors 141. According to yet another exemplary embodiment of the present disclosure (see FIGS. 1A and 1B), the image sensor and/or signal detectors 141 can be provided a number of centimeters away from the distal end of an endoscope 100, while the illumination sources 142 are provided on the distal end of the endoscope 100. According to another exemplary embodiment of the present disclosure (see FIG. 1C), the illumination sources 142 can be a particular number of centimeters away from the distal end of the endoscope 100, while the image sensor and/or signal detectors 141 are provided on the distal end of the endoscope 100. An endoscope objective lens 130 can image a forward view 110, while the image sensor and/or signal detectors 141 can image a side/backwards views 120.

Figure 1D:
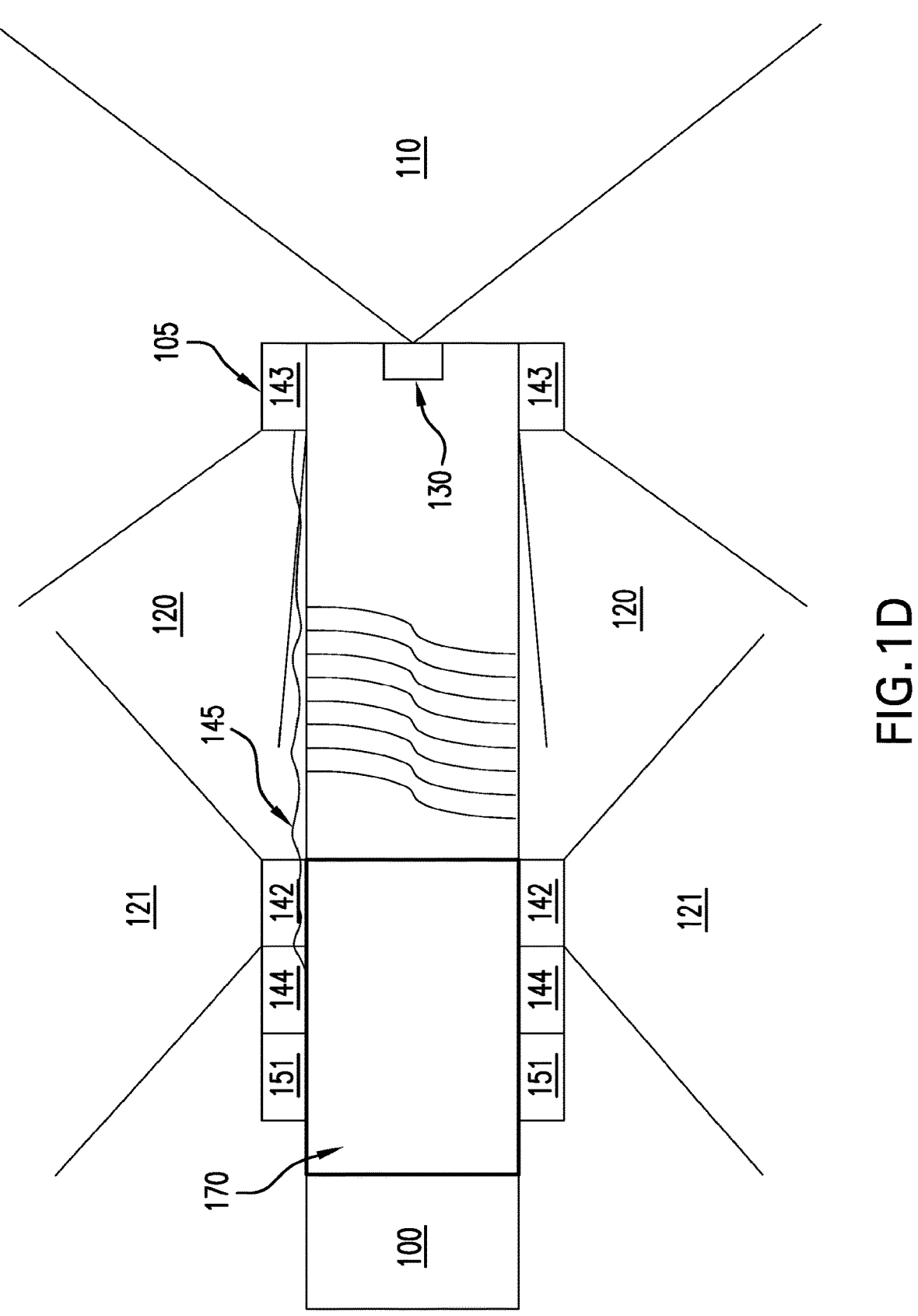

In yet another exemplary embodiment of the present disclosure, as shown in FIG. 1D, imaging optics 143 can be separated with image sensors and/or signal detector 144. For example, the image can be transported from the imaging optics 143 to the image sensor and/or signal detectors 144 using optical fibers 145 and/or relay optical components, such as, e.g., lenses and/or mirrors.

Figure 2A:
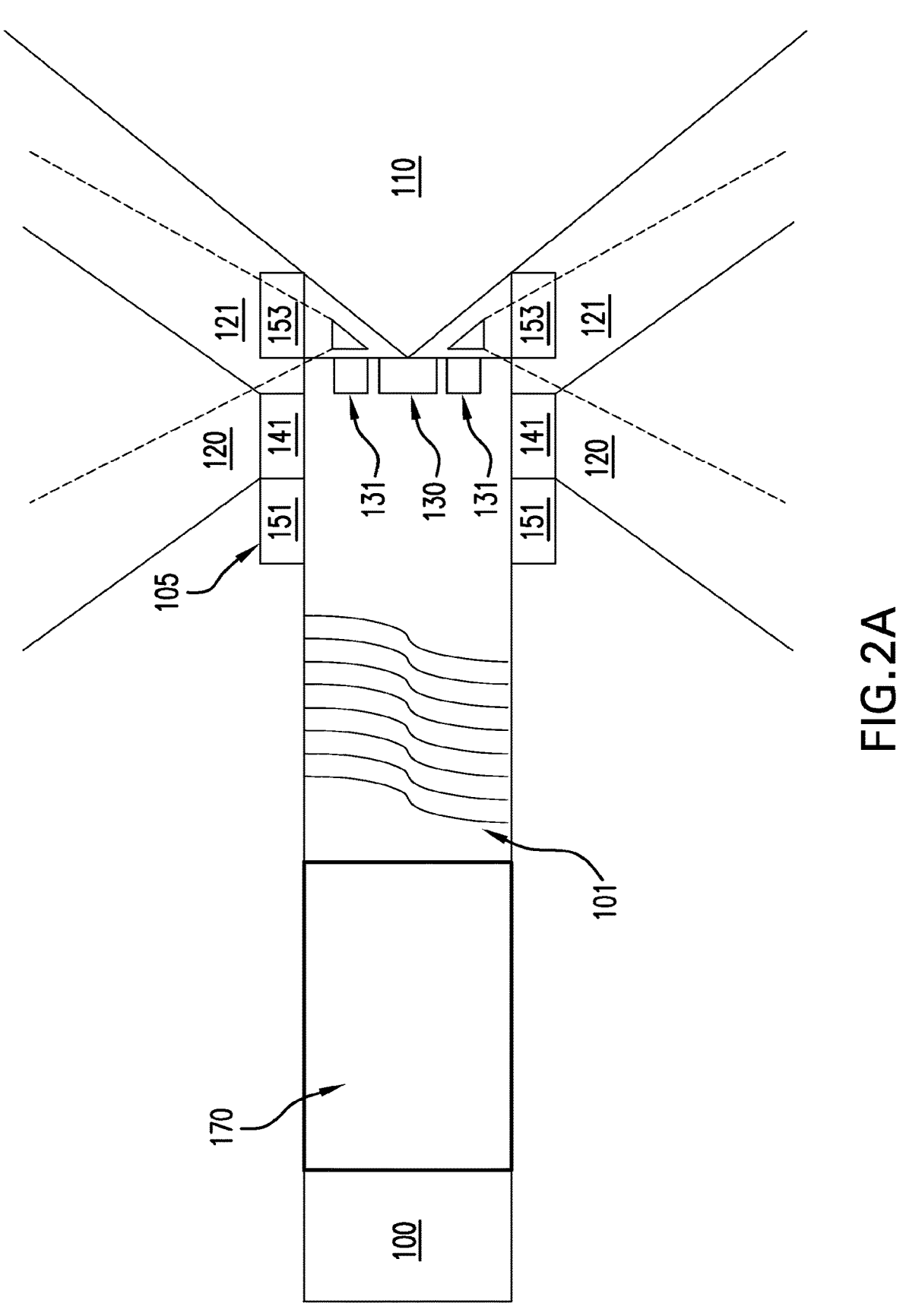
FIGS. 2A and 2B are exemplary block diagrams of a redirected light illumination from an endoscope thereof, according to certain exemplary embodiments of the present disclosure.
Figure 2B:
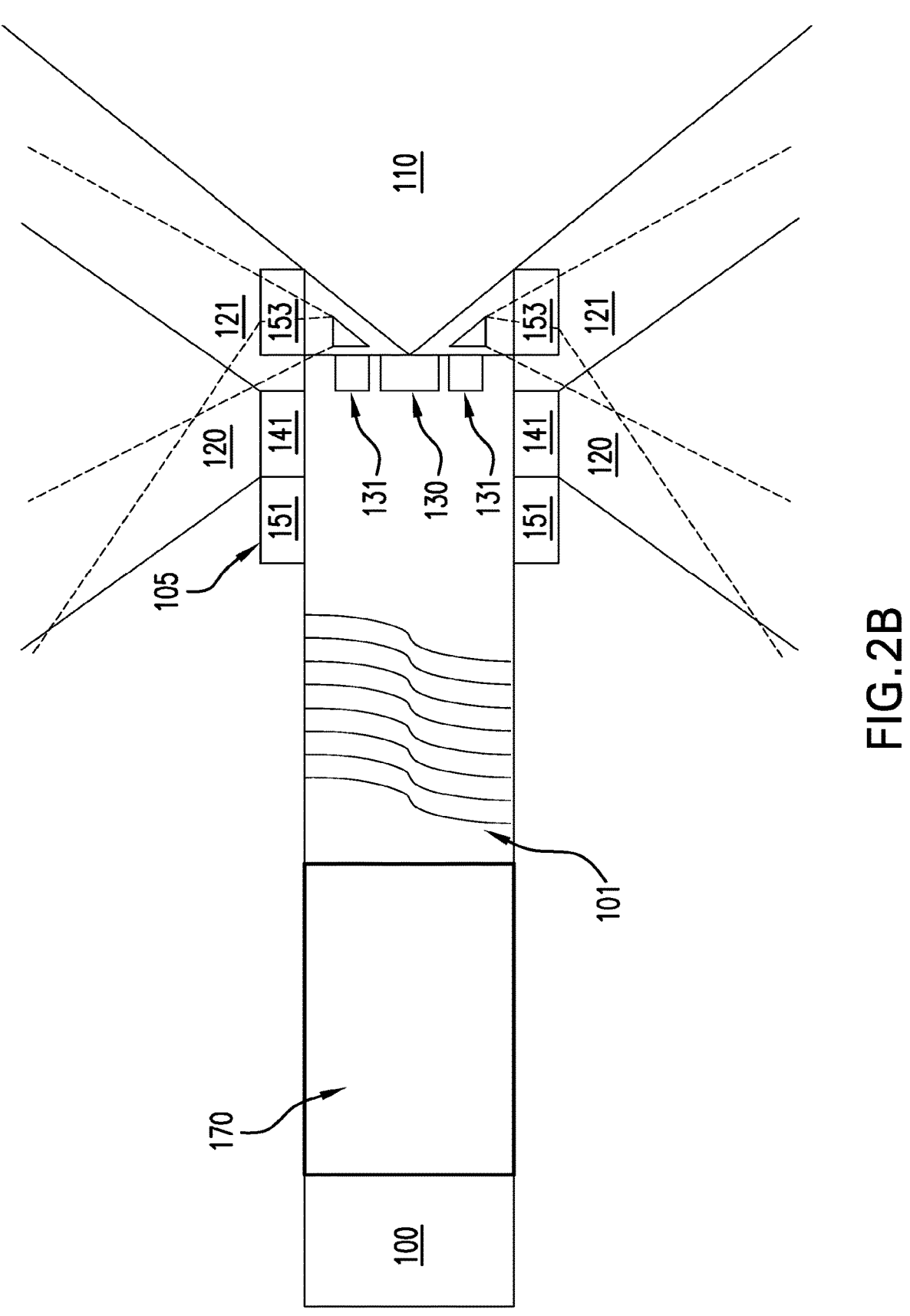

According to another exemplary embodiment of the present disclosure, as shown in FIGS. 2A and 2B, no additional illumination source has to be used. The illumination light 131 from the endoscope can be at least partially redirected to provide side/backwards illumination 121 in different directions in side/backwards views 120. The image sensor and/or signal detectors 141 can image the side/backwards views 120, while the endoscope objective lens 130 can image the forward view 110.

Figure 3A:
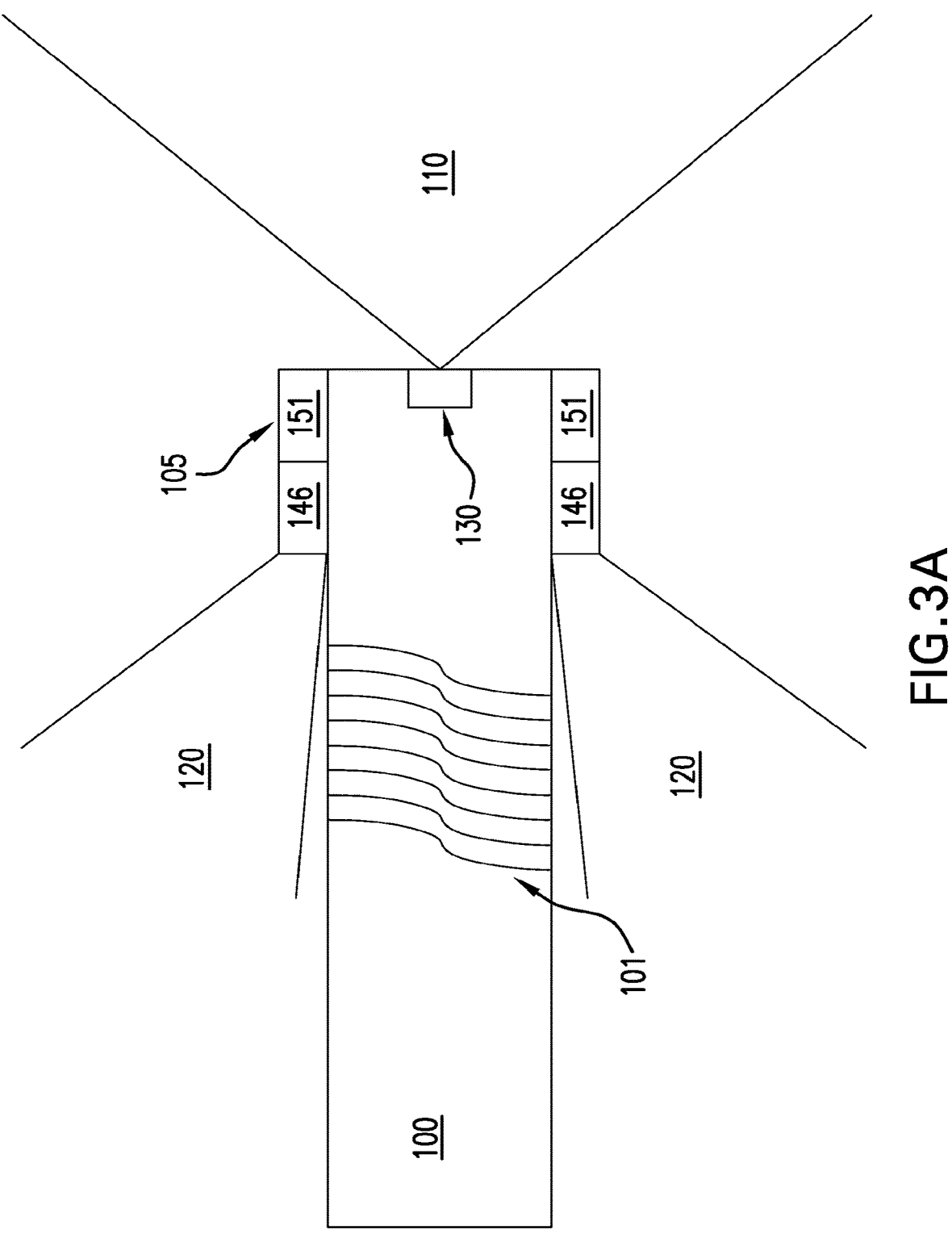
FIGS. 3A and 3B are exemplary block diagrams of an imaging apparatus, and optical, electronic, and scanning elements thereof according to certain exemplary embodiments of the present disclosure.
Figure 3B:
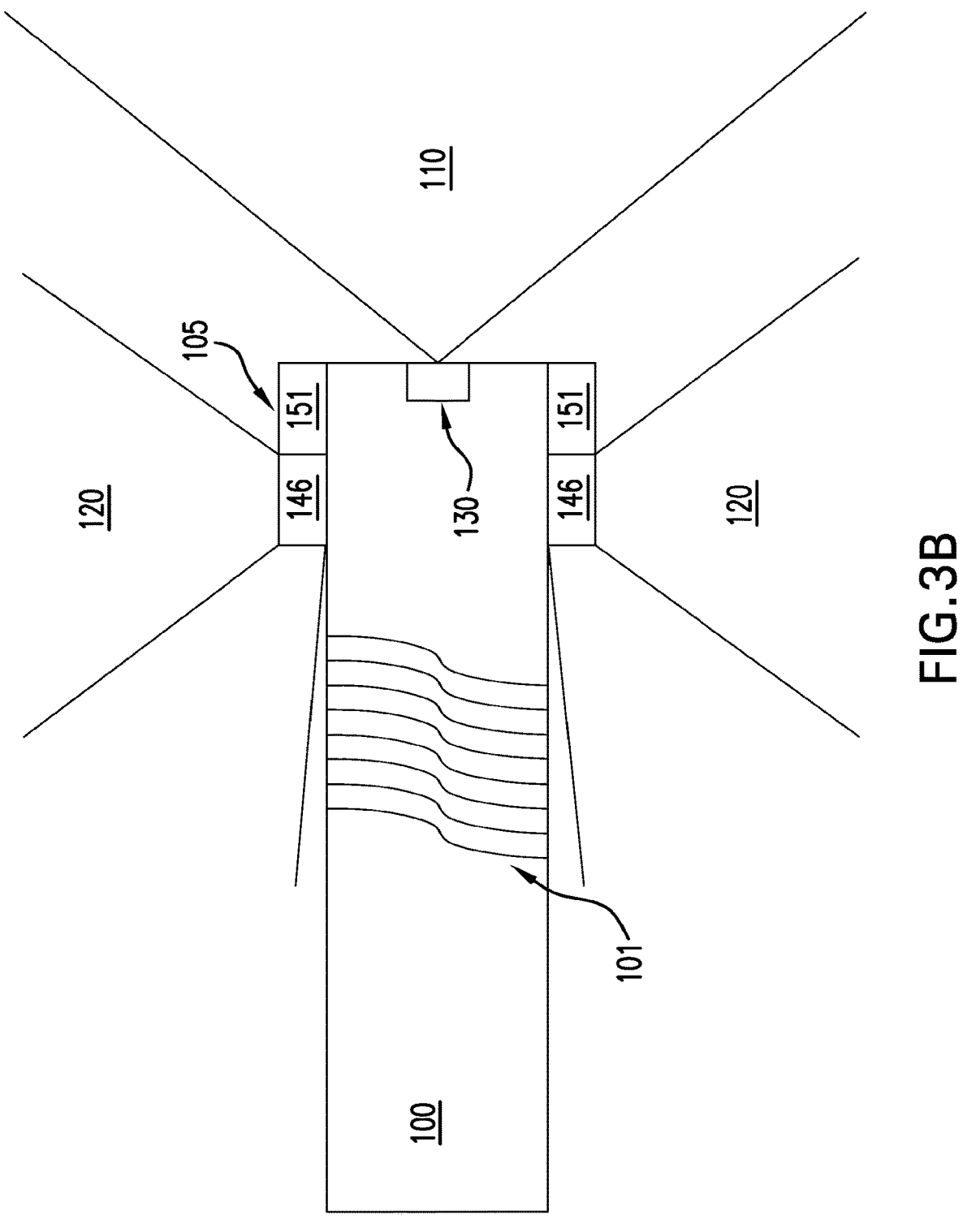

Traditional imaging using a camera can be replaced with the procedure of, e.g., compressive imaging according to an exemplary embodiment of the present disclosure. For example, a single detector, in addition to a suitable scanning mechanism, can be used to acquire the images of the subject under examination. According to still another exemplary embodiment of the present disclosure, as shown in FIGS. 3A and 3B, exemplary images can be detected by photodetectors 146, such as, e.g., photodiodes, photo cathodes, photomultiplier tubes, photoconductive cells, photovoltaic cells, photoresistors, phototransistors, cryogenic detectors, or single pixel CCD or single pixel CMOS sensors. In a further exemplary embodiment of the present disclosure, multiple pixels CCD and CMOS sensors can be used. According to another exemplary embodiment of the present disclosure, random and/or pseudorandom binary patterns and/or masks can be used as or instead of the photodetectors 146 to reconstruct the images of the subjects under examination. The exemplary patterns and/or masks 146 can be generated by spatial light modulators, digital micromirror array, spinning disk of random patterns and/or masks. According to another exemplary embodiment of the present disclosure, the masks 146 can be implemented using a set of light attenuating layers to modulate the light. In still another exemplary embodiment of the present disclosure, the masks 146 can be implemented using, e.g., array of aperture elements, like liquid crystal display (LCD), of which each element can be controlled independently. According to a further exemplary embodiment of the present disclosure, scanning mirrors, spatial light modulators, digital micromirror array, and/or array of aperture elements 146 can be used to control the direction of the light illumination, so that images of the subjects under examination can be reconstructed.

In an alternative exemplary embodiment of the present disclosure, three-dimensional structures can be measured by the imaging device by using passive stereo vision, using, e.g., multiple camera and/or image sensors, and/or detectors 146. According to yet another exemplary embodiment of the present disclosure, three-dimensional structure can be measured by the imaging device using active stereo vision, e.g., using structured illumination, laser structured light, and/or scanned light beams 146.

In a still further exemplary embodiment of the present disclosure, the imaging cap 105 can be rotated, such that the imaging device can access any particular area of interest.

Figure 4A:
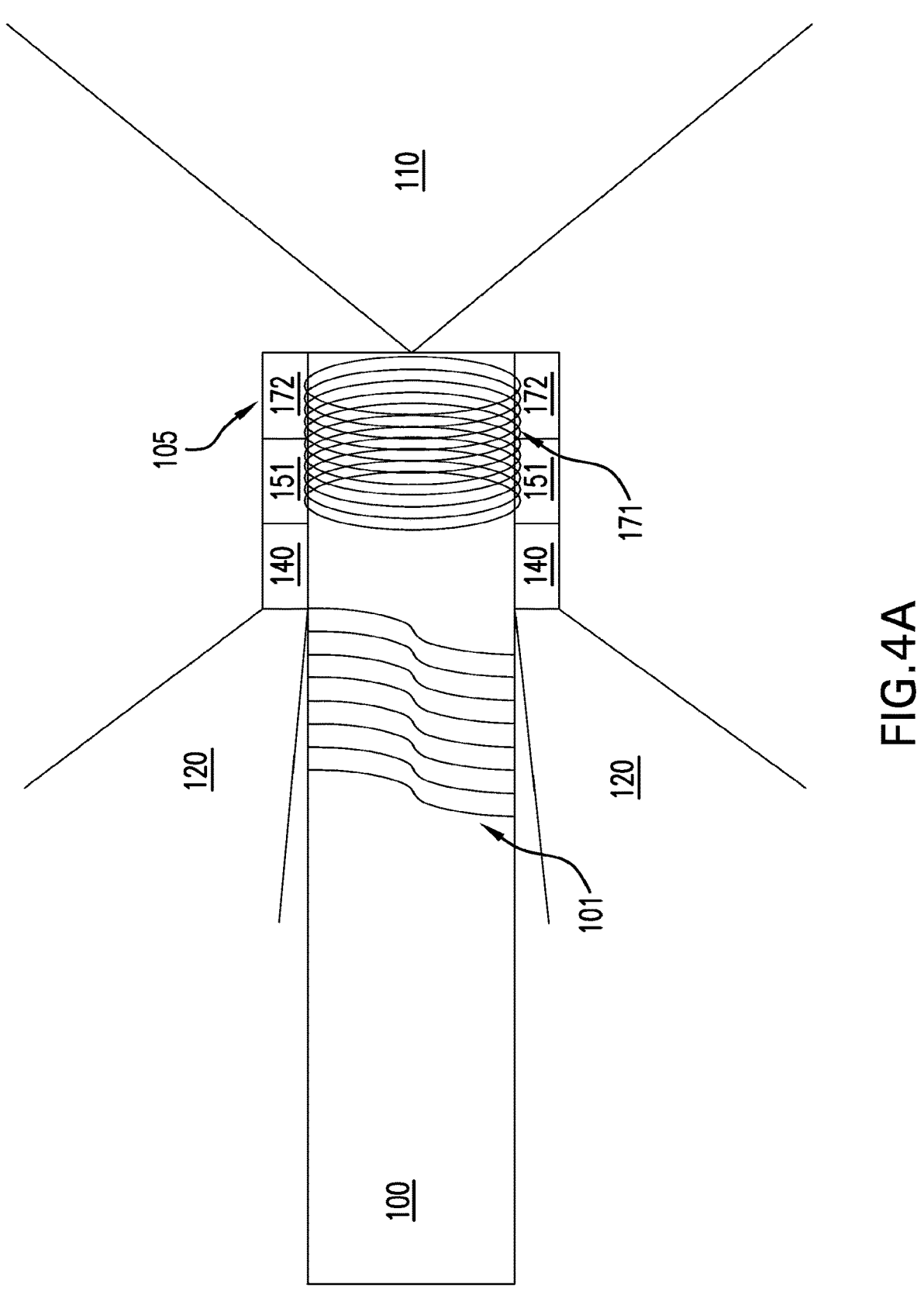
FIGS. 4A and 4B are exemplary block diagrams of inductive coupling power supply thereof according to certain exemplary embodiments of the present disclosure.
Figure 4B:
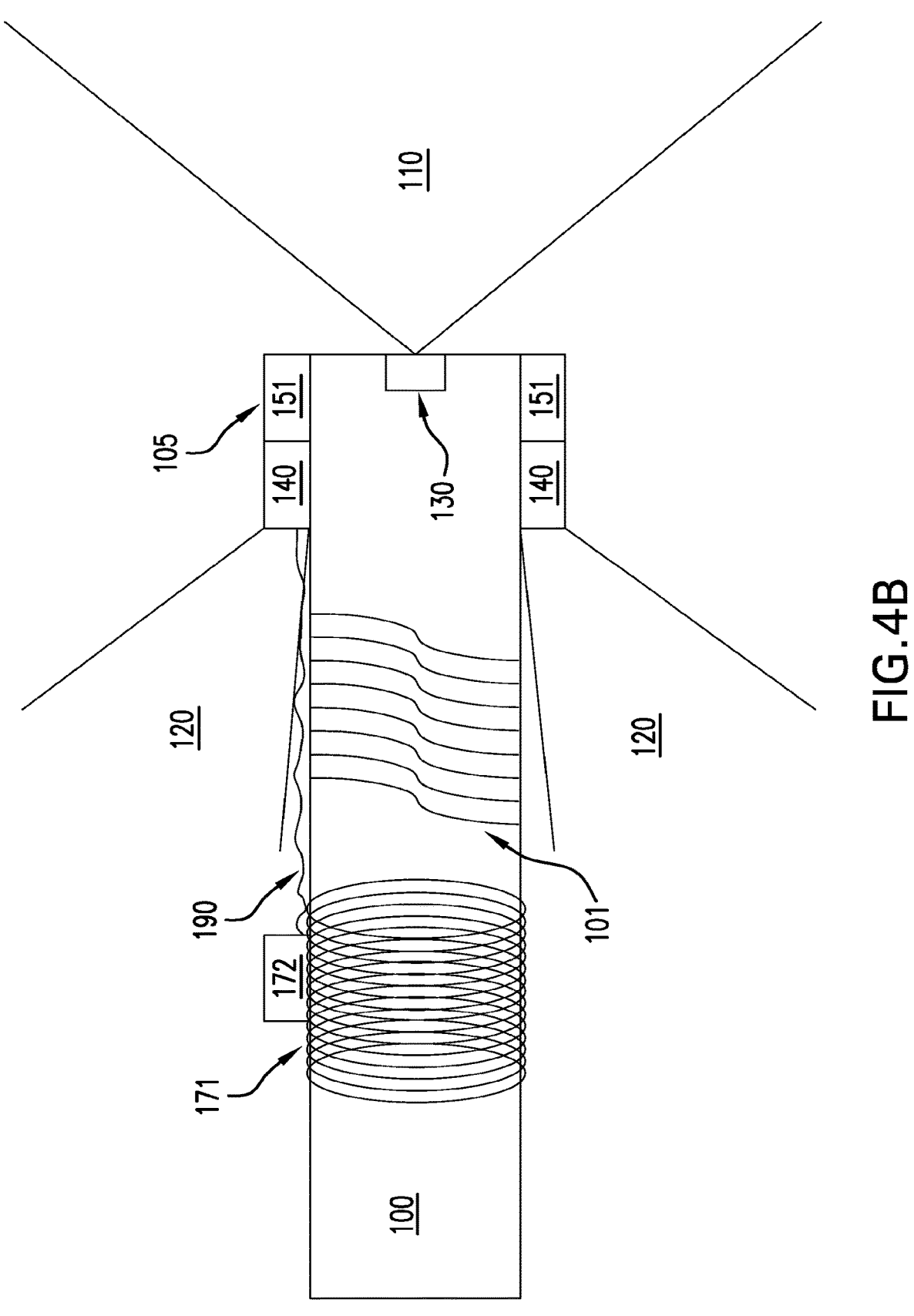

Furthermore, in one exemplary embodiment of the present disclosure, power can be provided wirelessly, e.g., via an inductive coupling. As shown in FIGS. 4A and 4B, inductive coils 171 can be arranged along the endoscope 100, and positioned such as to avoid the articulation section 101 of the endoscope. A power management circuit 172 can be provided to regulate the voltage and/or the current used in the imaging devices 140 and the wireless transmitters 151. The inductive coil 171 and the power management circuit 172 can be provided on the distal end of the endoscope 100 (see FIG. 4A) or at a variety of positions along the endoscope 100 (see FIG. 4B), in the latter exemplary case, connected to the imaging cap by wires 190.

Figure 5:
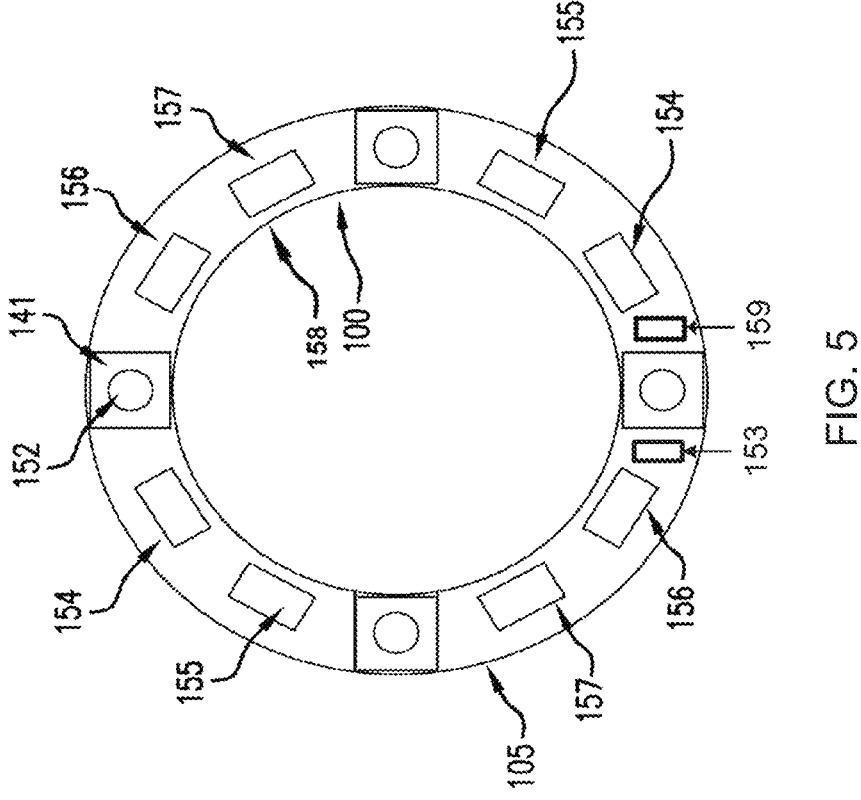
FIG. 5 is cross-sectional views of an exemplary imaging attachment cap that can be used with the exemplary apparati, which includes an inner shape and an outer shape, that can facilitate illuminating and imaging multidirectional fields of views.

According to yet another exemplary embodiment of the present disclosure, as shown in FIG. 5, multiple exemplary configurations of light illumination (see components 154-157) can be included in the cap 105 so as to illuminate the additional fields of view and provide multi wavelengths illumination and tissue fluorescence images. Multi wavelengths can be or have different colors, including, e.g., red, green, blue, and/or white, to provide multi bands imaging and different contrast for the tissue imaging, such as narrow band imaging used frequently in endoscopy. Fluorescence images can include tissue autofluorescence images and exogenous fluorescence images by using exogenous fluorescent contrast agents. In still another exemplary embodiment of the present disclosure, the light sources (see components 154-157) can be or include, e.g., light emitting diode (LED), laser diode (LD), and/or superluminescent diode (SLD).

According to a further exemplary embodiment of the present disclosure, switchable different wavelengths and/or color filters can be put in front of the light illumination sources (see components 154-157) to provide different illuminations. For example, switchable different wavelengths and/or color filters can be put in front of the image sensors, sources, and/or signal detectors (see, e.g., components 141, 142) to filter different signals associated with different wavelengths.

Furthermore, in one exemplary embodiment of the present disclosure, wireless transceivers can be attached to two-way communications with the wireless transceiver outside the subject under examination, to provide a fully functional management and control, such as, e.g., power management and regulation. For example, power can be turn on and off to save energy; light illumination modulation: the wavelength of the illumination source can be specifically chosen; and the positions of the camera can be rotated to provide maximum coverage of the area under examination.

In one exemplary embodiment of the present disclosure, to regulate power, the power supply (e.g., the battery 170) can be turned on/off and controlled by sensors of environmental indicators, such as the subject temperature, and/or pulse/heart rate. According to a particular exemplary embodiment of the present disclosure, the power supply (e.g., the battery 170) can also be turned on/off via a radio frequency (RF) wireless technology and/or optical transmission of the signals using light wavelengths that can penetrate the body effectively.

According to a further exemplary embodiment of the present disclosure, the apparatus is disposable, e.g., with only one time usage or after certain times of usages. In one exemplary embodiment of the present disclosure, a control circuit can be provided to allow the imaging device to turn on and off only a certain number of times. In addition or alternatively, the imaging device can be controlled or otherwise made to stop working after sterilization.

For example, to prevent an inappropriate operation of the imaging device, in one exemplary embodiment of the present disclosure, a sensor 153 (FIG. 5) can be provided in the device, such as heat and/or tension sensor, that can detect if there is any external force attempting to break or otherwise damage the imaging cap. If the external force is applied (up to a certain amount), the imaging device can stop working immediately.

In yet another exemplary embodiment of the present disclosure, the imaging cap 105 can be placed on endoscopes via a universal fit. According to yet another exemplary embodiment of the present disclosure, memory foam and/or silicone gel can be used as the inner tube 158 materials. The materials can provide sufficient friction to grab the endoscope and prevent the cap 105 from falling off. Further, clamps can be used to tightly grip the imaging cap 105, and/or a flexible connection segment can be provided between the battery housing 170 and the cap 105, with the endoscope 100.

Figure 6A:
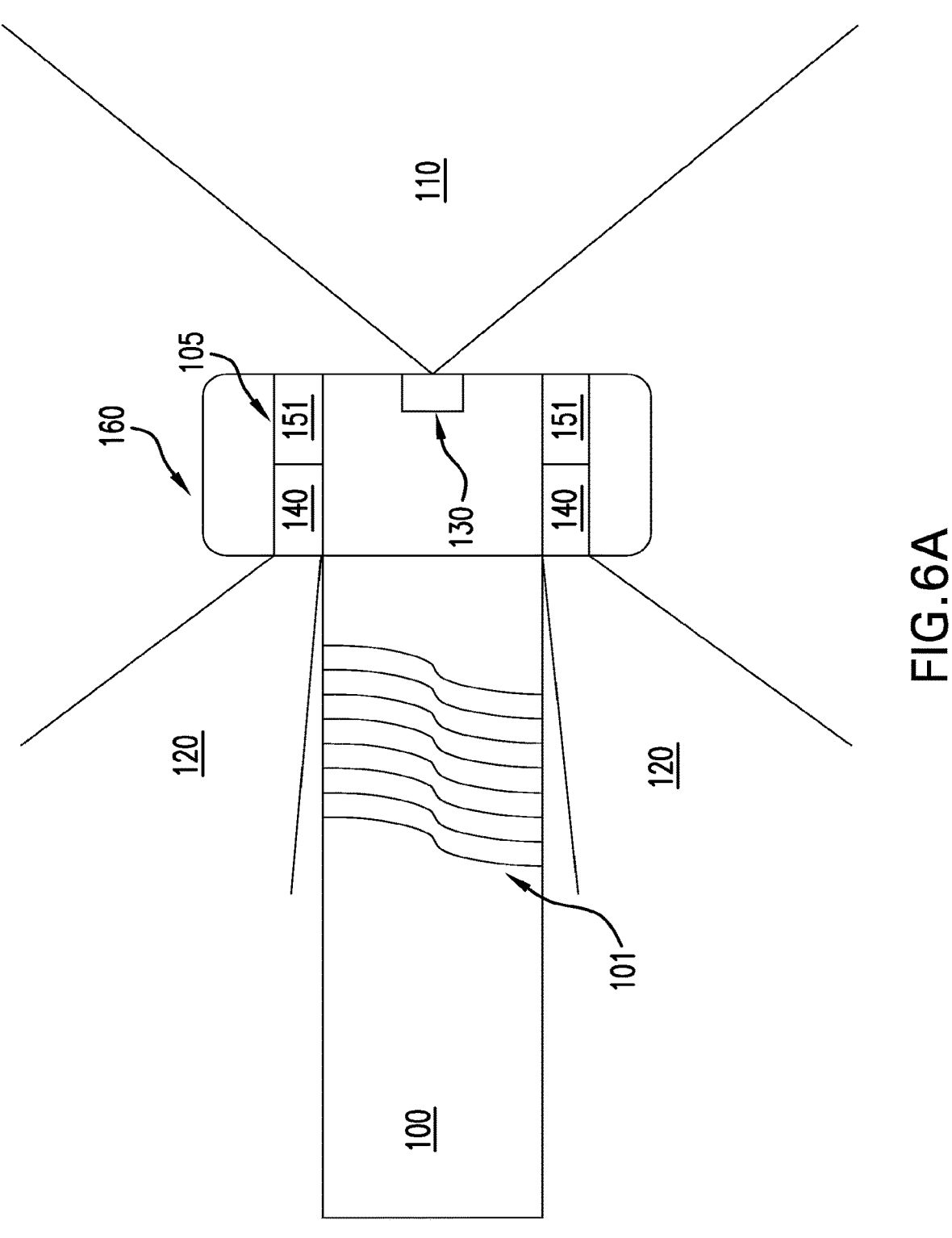
FIGS. 6A and 6B are exemplary block diagrams of the imaging apparatus, and optical, electronic, and mechanic elements thereof according to certain exemplary embodiments of the present disclosure.
Figure 6B:
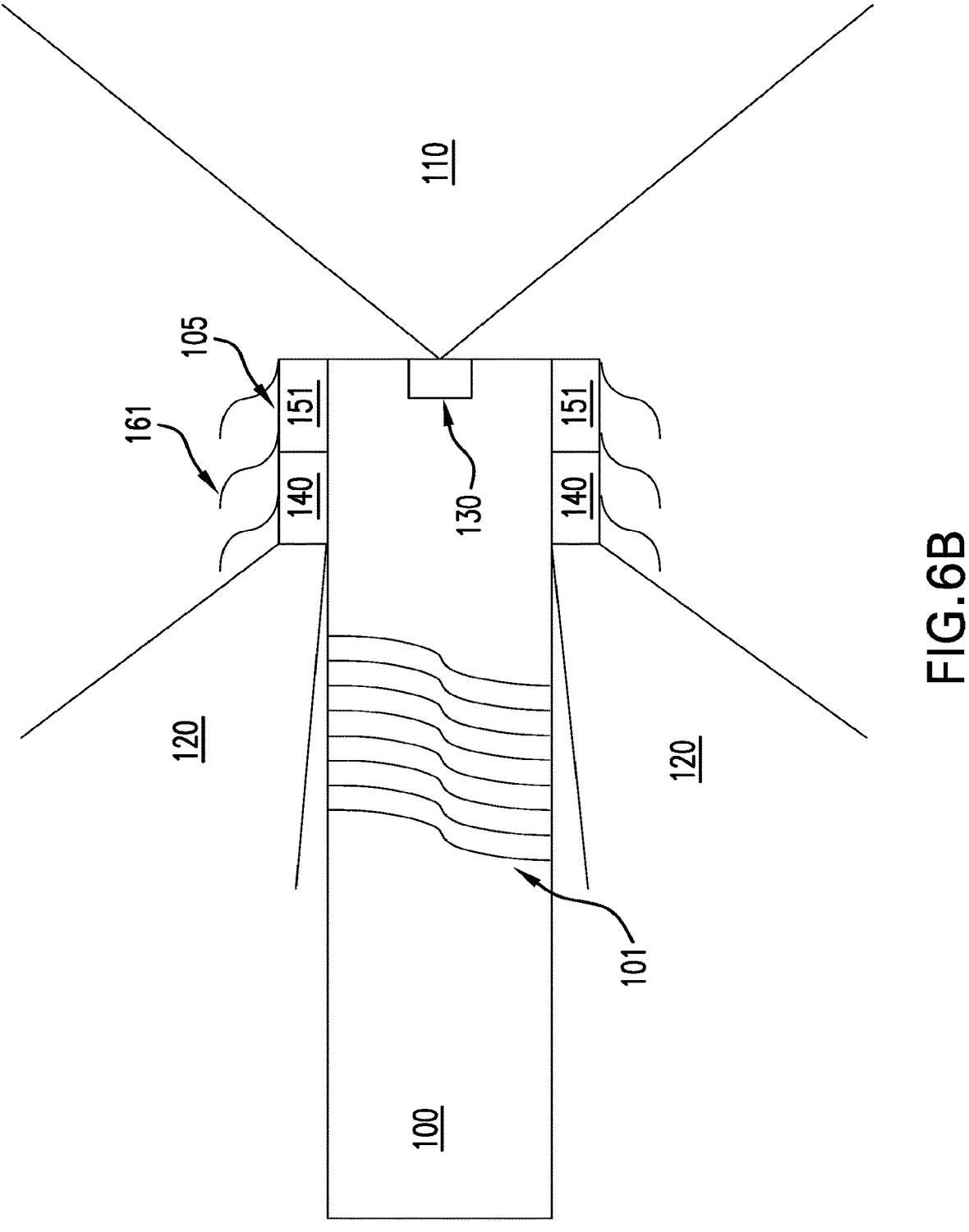

According to yet another exemplary embodiment of the present disclosure, as shown in FIGS. 6A and 6B, a balloon-like structure 160 and soft supportive projections 161, respectively, can be used to center the imaging devices (e.g., including the imaging cap 105) at the center of the anatomical structure, to provide better field of view, right depth of focus, reduction of the distortion due to the scaling, and reduction of the contact the mucosa. In a further another exemplary embodiment of the present disclosure, the balloon 160 and the soft supportive projections 161 can be transparent. According to yet another exemplary embodiment of the present disclosure, the diameter of the balloon-like structure 160 and the lengths and angles of the soft supportive projections 161 (as shown in FIGS. 6A and 6B, respectively) can be controlled by, e.g., a central processing unit (e.g., a computer) 159 in the image device (e.g., the imaging cap 105), see FIG. 5 by, e.g., inflating the balloon-like structure 160 and/or moving and rotating the soft supportive projections 151.

In still another exemplary embodiment of the present disclosure, the whole or part of the imaging cap 105 can be transparent. A first electro-magnetic radiation, and a second electro-magnetic radiation from at least one anatomical structure that based on the first electro-magnetic radiation can pass through the imaging window.

Figure 7:
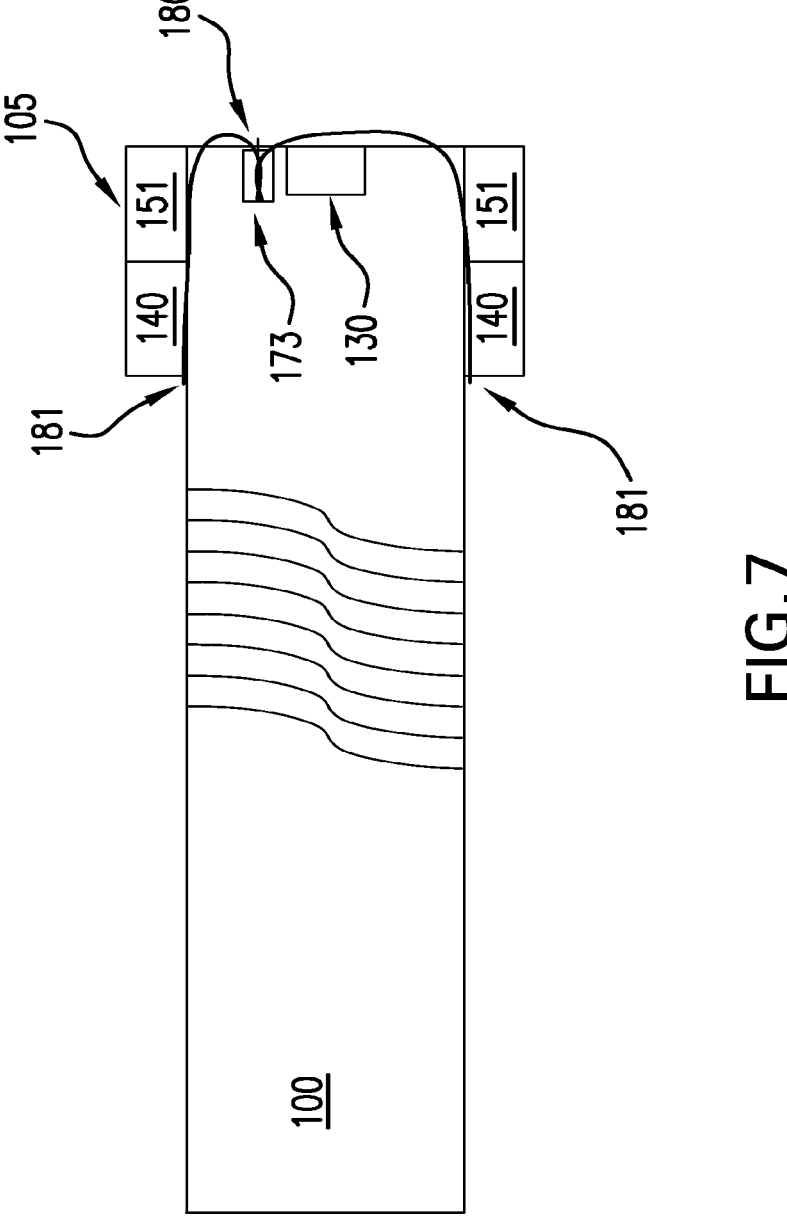
FIG. 7 is an exemplary block diagram of a redirected water or air nozzle and water or air ducts thereof according to certain exemplary embodiments of the present disclosure.

According to yet another exemplary embodiment of the present disclosure, as shown in FIG. 7, a transparent window of the imaging cap 105 can be cleaned by a water or air nozzle 181, which can be connected by small hoses and/or ducts 180 with the water or air nozzle 173 of the endoscope 100. In a further another exemplary embodiment of the present disclosure, the imaging cap 105 can be rotated, so that a window shield can be used to scrub the imaging window of the imaging cap 105 to keep it clean. According to yet further another exemplary embodiment of the present disclosure, the imaging window of the imaging cap 105 can be coated with materials (e.g., hydrophobic coatings) to prevent mucus and other environmental liquids from staining the imaging window of the imaging cap 105.

Figure 8A:
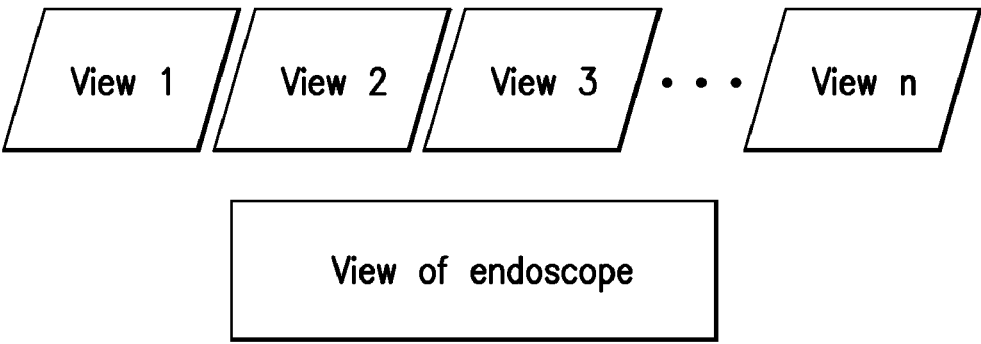
FIG. 8A is a block diagram of an image processing and display system according to an exemplary embodiment of the present disclosure.
Figure 8B:
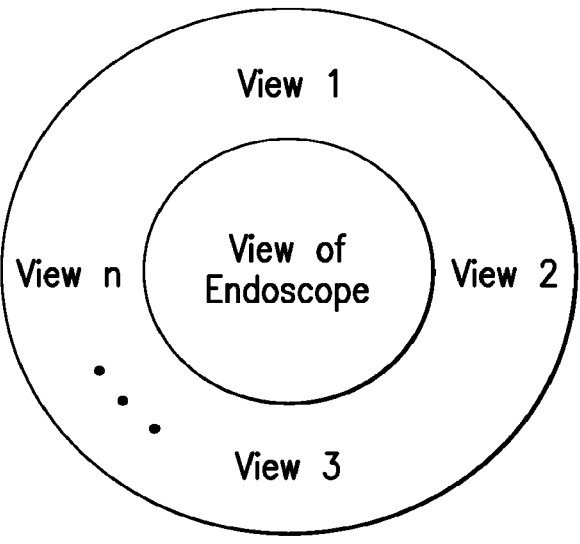
FIG. 8B is a diagram of a field of view provided by the image processing and display system shown in FIG. 8A.

In an additional exemplary embodiment of the present disclosure, as shown in FIGS. 8A and 8B, it is possible to simultaneously display all the captured images with the endoscope captured images, according to the relative space positions and orientations of the image sensors/signal detectors. Algorithms, procedures and/or software can be provided, e.g., used to program a computer, to correct any distortion of the anatomical structure under examination induced by the imaging apparatus, reconstruct the relative positions of different views related to the forward view of the endoscope, and balance the color. It is also possible to facilitate a toggling to selectively display any individual field of views via a manual and/or electronic switch the algorithms and/or software.

In order to facilitate an accurate localization of target lesions or regions of interest obtained with the exemplary imaging system, an exemplary procedure (which can be used to program a processing hardware arrangement, such as, e.g., a computer) can be used to reconstruct the three-dimensional positions of the target lesions and/or regions of interest.

According to yet another exemplary embodiment of the present disclosure, the imaging device (e.g., the imaging cap 105) can provide position information of the target lesions or regions of interest. In a further another exemplary embodiment of the present disclosure, the imaging device (e.g., the imaging cap 105) can mark the anatomical structure by ablation the tissue using heat or laser. According to still another exemplary embodiment of the present disclosure, the imaging device (e.g., the imaging cap 105) has position sensor which can provide three dimensional positions of the imaging device relative to a fix position outside the subject, such as the operation bed.

Figure 9:
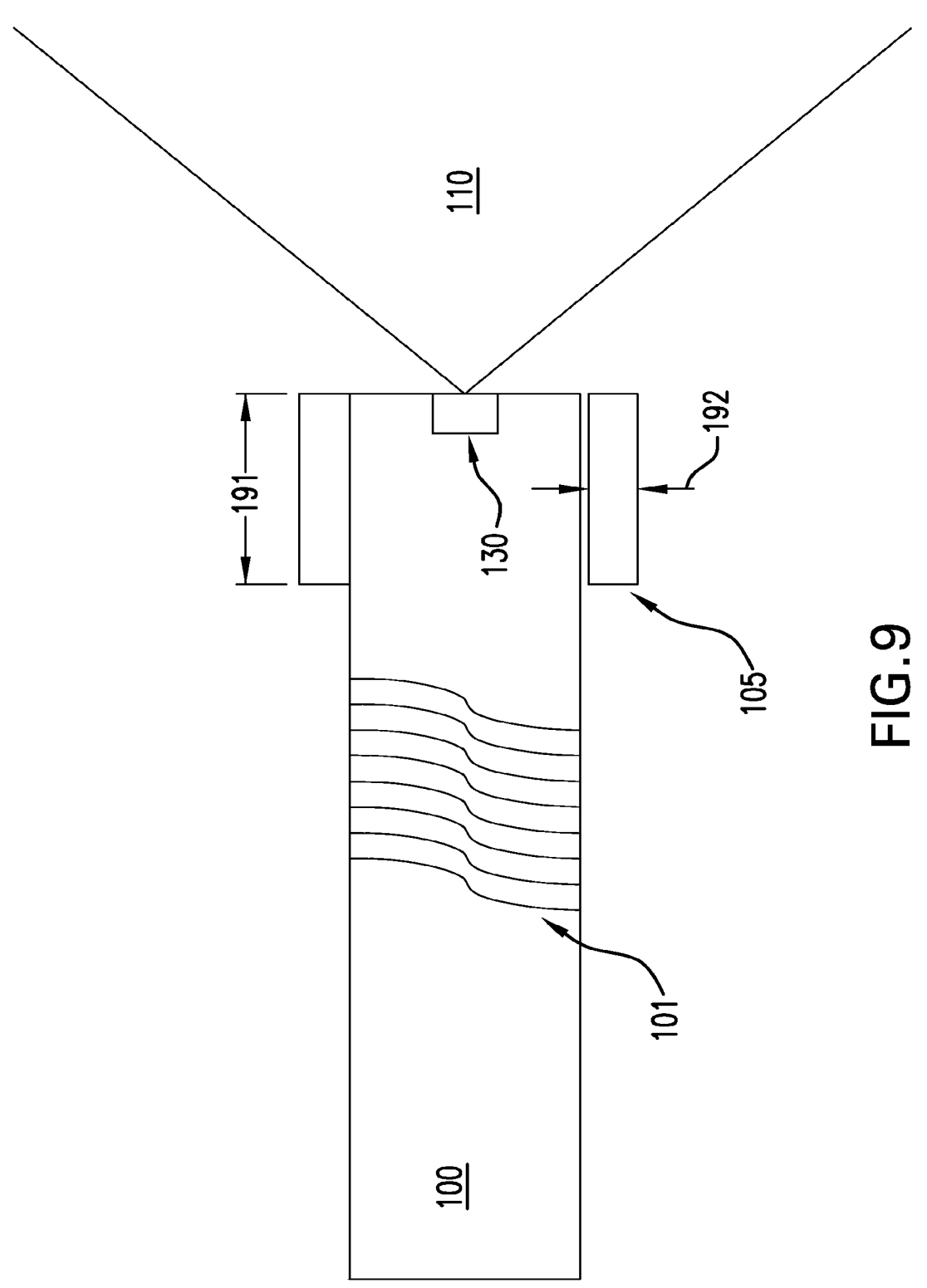
FIG. 9 is an exemplary block diagram of the imaging apparatus and probe in which a relative placement of the imaging apparatus and an exemplary length and thickness of an outer housing of the imaging apparatus are illustrated.

According to a further exemplary embodiment of the present disclosure, as shown in FIG. 9, the imaging apparatus (e.g., which can be or include the imaging cap 105) can include a protective outer housing with a total exemplary length measured along the axis of the probe (191) to be between about, e.g., 25 mm and 35 mm, and total thickness of a wall of the housing extending radially from the probe outer surface (192) can be between about, e.g., 1 mm and 2 mm.

The foregoing merely illustrates the principles of the disclosure. Various modifications and alterations to the described embodiments can be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems including second or higher order harmonic microscopy, sum/difference frequency fluorescence microscopy (one-photon or multi-photon fluorescence), and Raman microscopy (CARS, SRS), and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art can be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, micro-processor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced above can be incorporated herein by reference in their entireties.

What is claimed is:

1. An apparatus for coupling to a probe, the probe having a proximal end and a distal end and a long axis therebetween, and providing image information regarding at least one structure, comprising:

a light-providing arrangement comprising a light source provided at the distal end of the probe which is configured to forward predetermined patterns of light radiation to the at least one structure and to forward multiple radiations at different respective switchable wavelengths to at least one portion of the at least one structure;

a detector arrangement which is configured to detect at least one return radiation from at least one portion of the at least one structure based on the predetermined patterns, and provide data for the at least one portion based on the at least one return radiation, the detector arrangement being disposed proximal to and separated from the light source at the distal end of the probe;

a computer arrangement comprising a processor which is configured to generate the image information using random or pseudorandom patterns to reconstruct the image information, wherein the image information comprises image data for the at least one portion as a function of the data;

a structural connection configuration comprising a cap which is structured and configured to be attached to the probe, and connected to the detector arrangement; and a tension sensor configured to detect an external force applied to the cap, wherein the detector arrangement is stopped if the external force is sufficient to at least one of break or damage the cap.

2. The apparatus of claim 1, wherein the light-providing arrangement includes a source arrangement.

3. The apparatus of claim 1, wherein the detector arrangement and the computer arrangement are part of an electronics arrangement comprising a wireless transmitter which is configured to transmit the image information wirelessly.

4. The apparatus of claim 3, wherein the electronics arrangement is configured to transmit the image information wirelessly in real time.

5. The apparatus of claim 3, wherein the apparatus further comprises:

a portable power arrangement comprising a battery disposed adjacent to the probe, wherein at least a portion of the battery and at least a portion of the detector arrangement are intersected by a plane that is perpendicular to the long axis, the battery being configured to provide power to at least one component of the electronics arrangement.

6. The apparatus of claim 5, further comprising an inductive arrangement which is configured to recharge the portable power arrangement.

7. The apparatus of claim 1, wherein the cap includes an inner tube surface comprising a polymeric material to frictionally engage the probe.

8. The apparatus of claim 7, wherein the structural connection configuration is structured to be connected to the probe at or near a distal end thereof.

9. The apparatus of claim 1, further comprising a first fluid transmitting arrangement coupled to a second fluid transmitting arrangement of the probe.

10. The apparatus of claim 1, wherein the light-providing arrangement is configured to forward multiple radiations at different respective switchable wavelengths to at least one portion of the at least one structure, wherein the multiple radiations are provided as multiple bands of radiation to provide differential contrast for tissue imaging, and wherein the light-providing arrangement includes a plurality of individual lights distributed around a perimeter of the probe, wherein at least two of the plurality of individual lights emit different wavelengths of light from one another.

11. The apparatus of claim 1, wherein the probe comprises an endoscope.

12. The apparatus of claim 3, wherein the image information is regarding at least one portion of the at least one structure that is different from further information regarding the at least one structure obtained separately by the probe.

13. The apparatus of claim 12, wherein the electronics arrangement is configured to obtain the image information from a first direction, and the probe is configured to obtain the further information from a second direction opposite to the first direction.

14. The apparatus of claim 12, wherein the electronics arrangement is configured to obtain the image information from a first direction, and the probe is configured to obtain the further information from a second direction perpendicular to the first direction.

* * * * *